(12) United States Patent
Unger

(10) Patent No.: US 9,642,344 B2
(45) Date of Patent: May 9, 2017

(54) SYSTEM AND METHOD FOR BREEDING AND HARVESTING INSECTS

(71) Applicant: Katharina Unger, Graz (AT)

(72) Inventor: Katharina Unger, Graz (AT)

(73) Assignee: LIVIN FARMS LTD., Twickenham (GB)

( * ) Notice: Subject to any disclaimer, the term of this patent is extended or adjusted under 35 U.S.C. 154(b) by 0 days.

(21) Appl. No.: 15/339,900

(22) Filed: Oct. 31, 2016

(65) Prior Publication Data
US 2017/0042131 A1 Feb. 16, 2017

Related U.S. Application Data

(63) Continuation-in-part of application No. PCT/EP2015/065274, filed on Jul. 5, 2015.
(Continued)

(51) Int. Cl.
*A01K 67/033* (2006.01)
*A01K 67/00* (2006.01)

(52) U.S. Cl.
CPC .................. *A01K 67/033* (2013.01)

(58) Field of Classification Search
CPC .............................. A01K 67/033; A01K 29/00
(Continued)

(56) References Cited

U.S. PATENT DOCUMENTS 2,670,562 A * 3/1954 Gould .................... A01K 97/04
119/6.5

4,334,498 A * 6/1982 Bedding .............. A01K 67/033
119/6.7
(Continued)

FOREIGN PATENT DOCUMENTS

CN 103598148 A 2/2014
FR 3013561 A1 5/2015
(Continued)

OTHER PUBLICATIONS

Cickova, Helena et al., "The use of fly larvae for organic waste treatment", Waste Management, No. 35, pp. 68-80, 2015, Elsevier Ltd. 2014.
(Continued)

*Primary Examiner* — Yvonne Abbott-Lewis
(74) *Attorney, Agent, or Firm* — Millman IP Inc.

(57) ABSTRACT

In an aspect, a system for breeding and harvesting insects is provided and includes an egg-producing chamber structure configured to receive insect pupae for pupation and to permit emerged adult insects to mate and oviposit insect eggs, at least one oviposition region in the egg-producing chamber structure configured to receive the insect eggs and apertured to permit at least one of the insect eggs and neonates of the insect eggs to pass therethrough, at least one larvae-growth chamber in communication with the at least one oviposition region so as to be configured to receive the at least one of the insect eggs and neonates of the insect eggs, wherein the larvae-growth chamber is further configured to permit the at least one of the insect eggs and neonates of the insect eggs to transition into larvae and to hold feed material for the larvae, a harvesting receptacle positioned to hold larvae, and an inclined surface positioned to receive larvae from the at least one larvae-growth chamber, and to provide a passageway for the larvae to travel to the harvesting receptacle.

20 Claims, 42 Drawing Sheets

Related U.S. Application Data

(60) Provisional application No. 62/249,187, filed on Oct. 31, 2015, provisional application No. 62/021,111, filed on Jul. 5, 2014.

(58) Field of Classification Search
USPC .................................. 119/6.6, 6.5, 6.7, 322
See application file for complete search history.

(56) References Cited

U.S. PATENT DOCUMENTS

| | | | | |
|---|---|---|---|---|
| 4,368,690 A | * | 1/1983 | Tenzer | A01K 67/033 |
| | | | | 119/496 |
| 4,411,220 A | * | 10/1983 | Voegele | A01K 67/033 |
| | | | | 119/6.6 |
| 4,417,545 A | * | 11/1983 | Finney | A01K 67/033 |
| | | | | 119/6.6 |
| 4,765,274 A | * | 8/1988 | Pizzol | A01K 67/033 |
| | | | | 119/6.6 |
| 4,765,275 A | * | 8/1988 | Yukawa | A01K 67/033 |
| | | | | 119/6.5 |
| 5,042,427 A | * | 8/1991 | Bedding | A01N 63/00 |
| | | | | 119/6.7 |
| 5,351,643 A | * | 10/1994 | Hughes | A01K 67/033 |
| | | | | 119/6.5 |
| 5,819,685 A | * | 10/1998 | Kappelt | A01K 67/033 |
| | | | | 119/322 |
| 6,244,213 B1 | * | 6/2001 | Tedders | A01K 67/033 |
| | | | | 119/6.6 |
| 6,780,637 B2 | | 8/2004 | Olivier | |
| 6,863,022 B2 | * | 3/2005 | Fleischmann | A61K 35/64 |
| | | | | 119/6.5 |
| 8,733,284 B2 | | 5/2014 | Courtright | |
| 9,462,795 B2 | * | 10/2016 | Chin | A01K 67/033 |
| 2003/0143728 A1 | | 7/2003 | Olivier | |
| 2014/0020630 A1 | * | 1/2014 | Courtright | A01K 29/00 |
| | | | | 119/6.6 |
| 2015/0122182 A1 | | 5/2015 | Aldana et al. | |

FOREIGN PATENT DOCUMENTS

| | | |
|---|---|---|
| WO | 2012/115959 A2 | 8/2012 |
| WO | 2013/166590 A1 | 11/2013 |

OTHER PUBLICATIONS

PCT/EP2015/065274, International Search Report & Written Opinion, Nov. 9, 2015, European Patent Office.

* cited by examiner

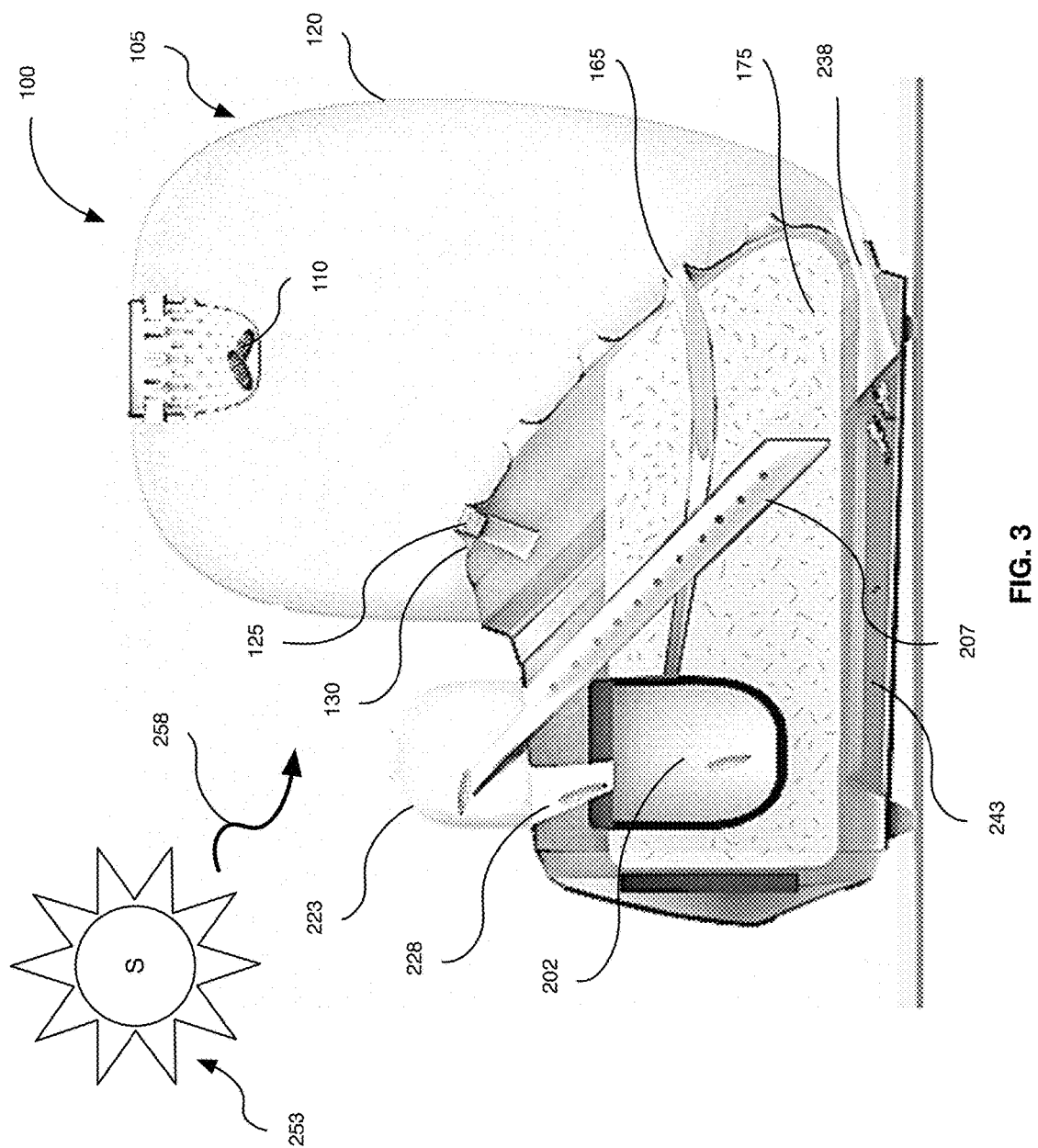

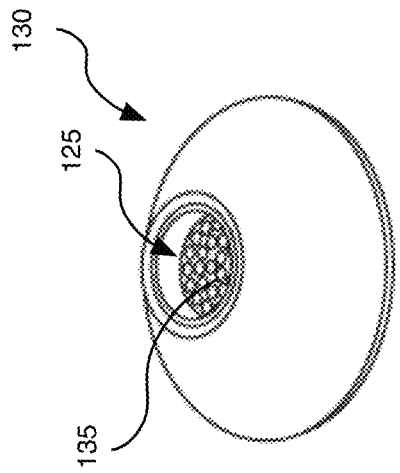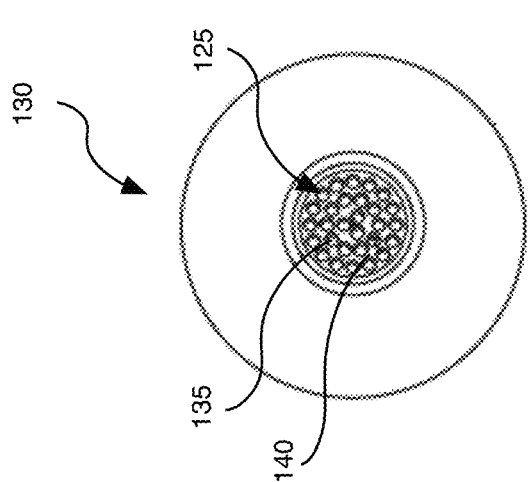
FIG. 4A
FIG. 4B
FIG. 4C

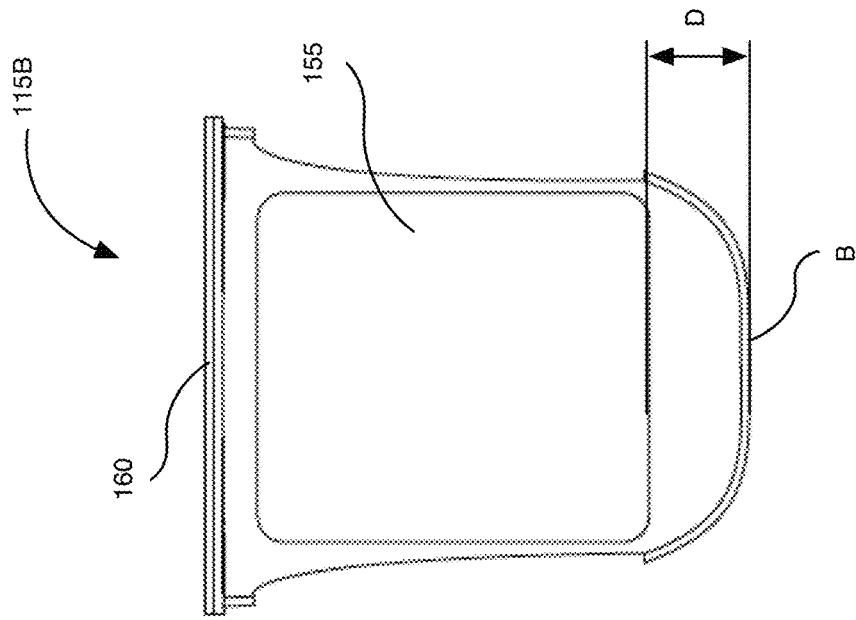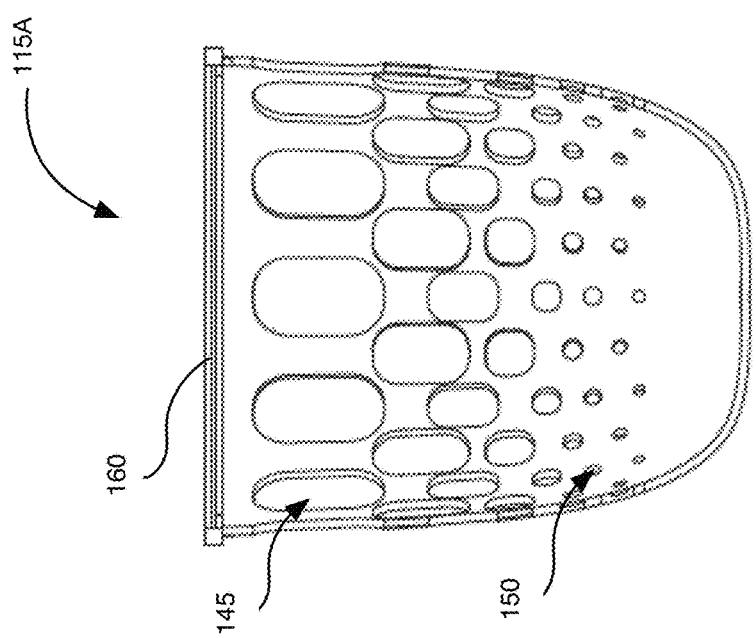

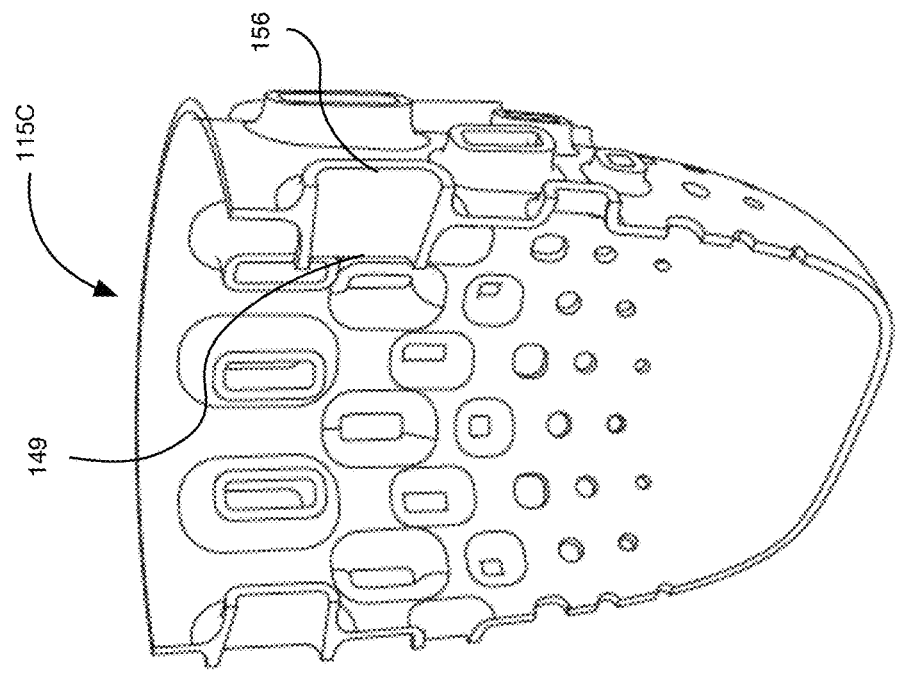
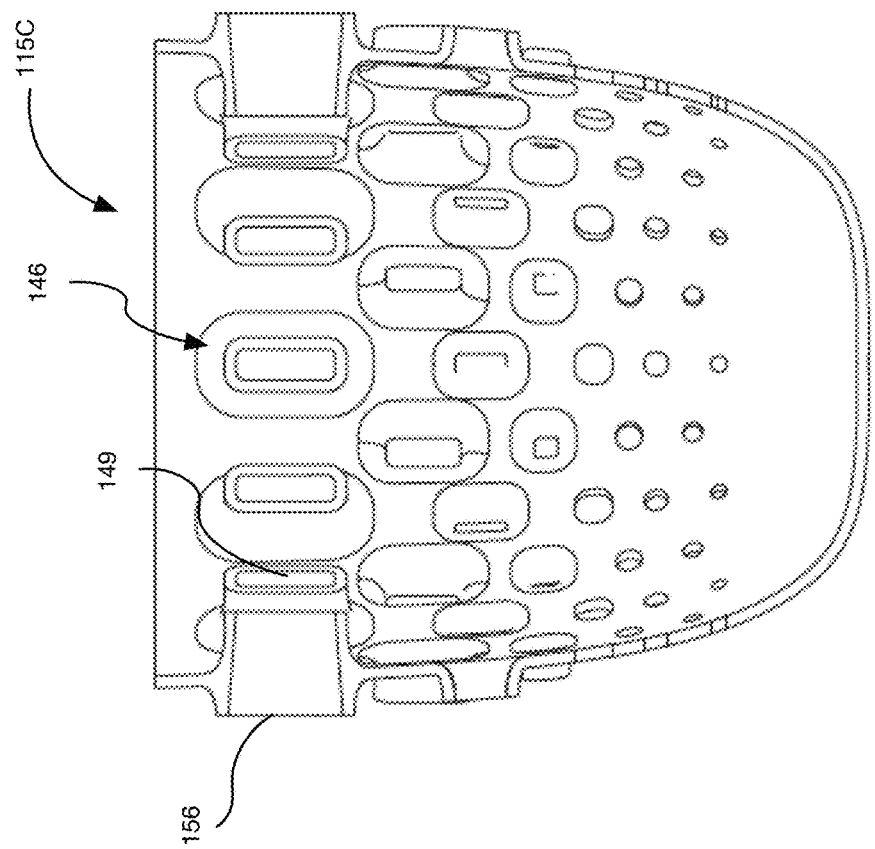

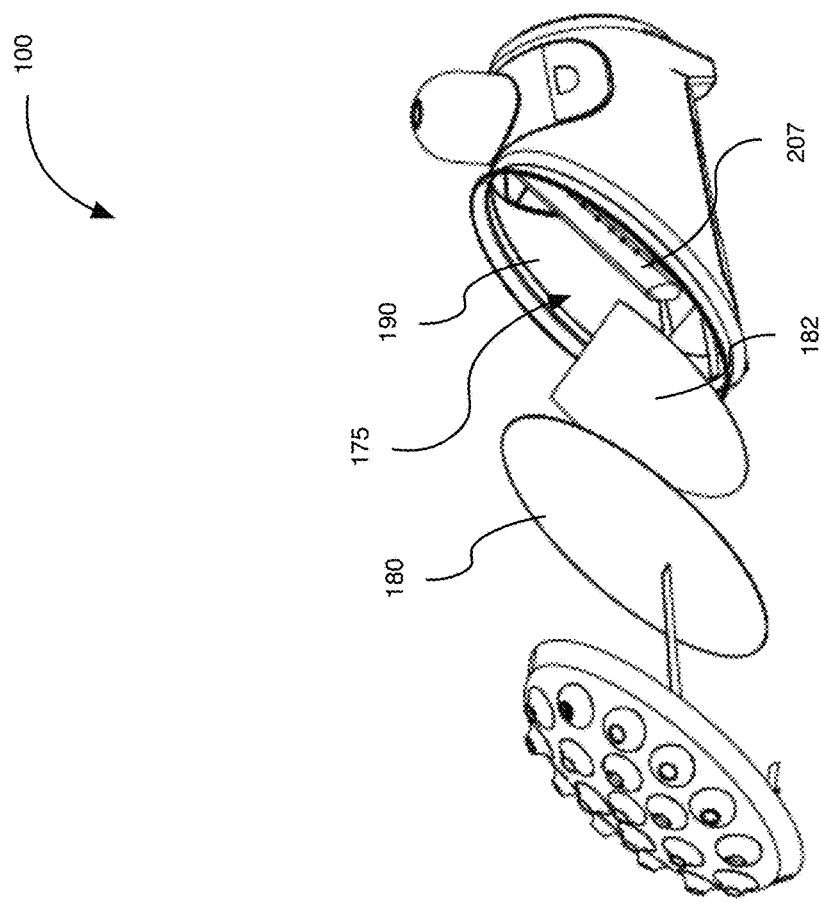
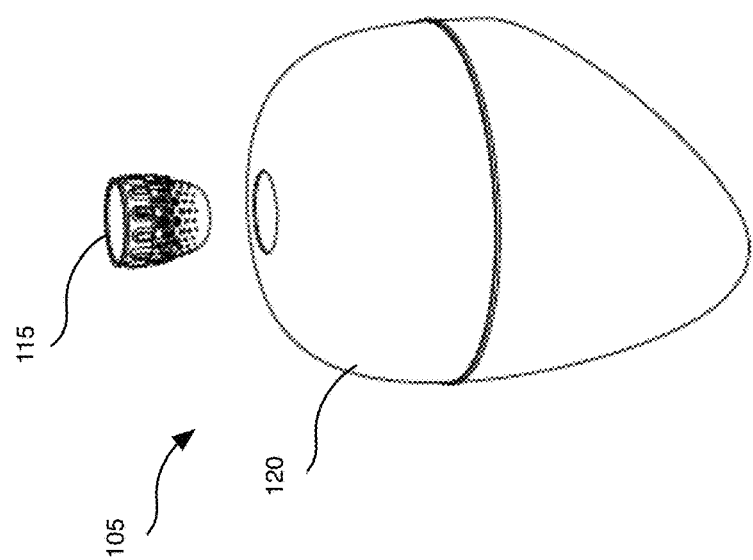
FIG. 7

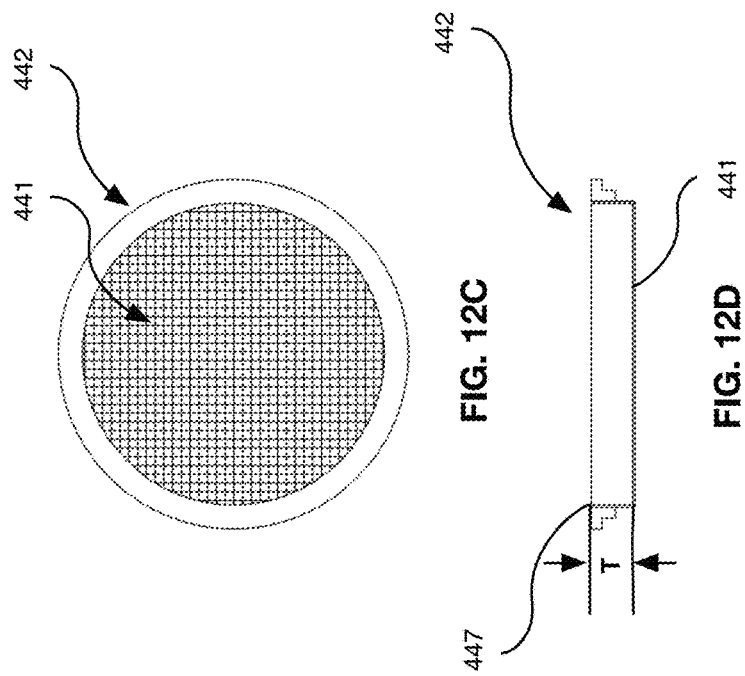
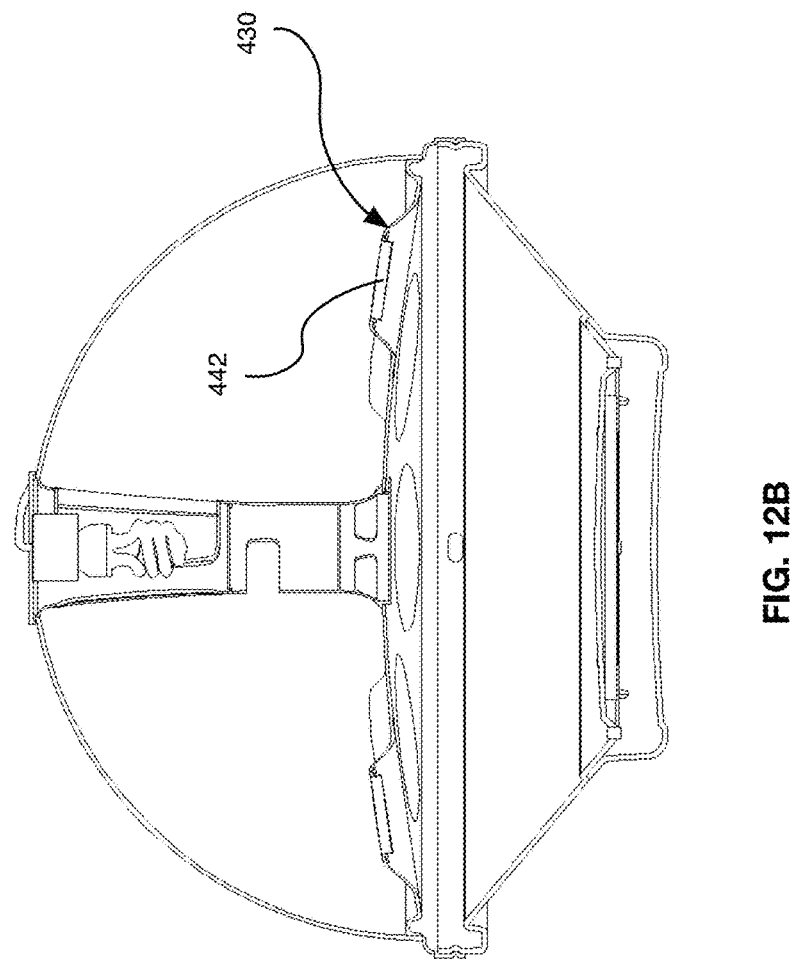

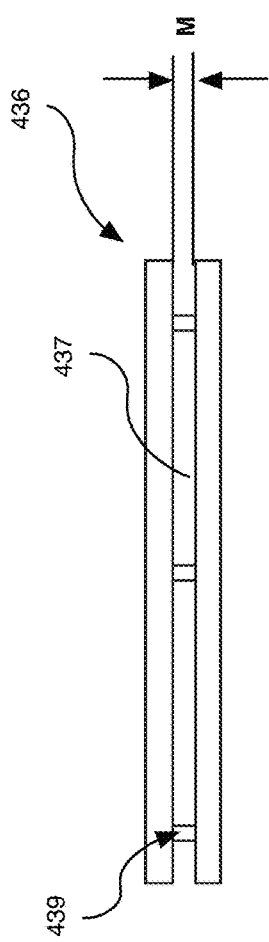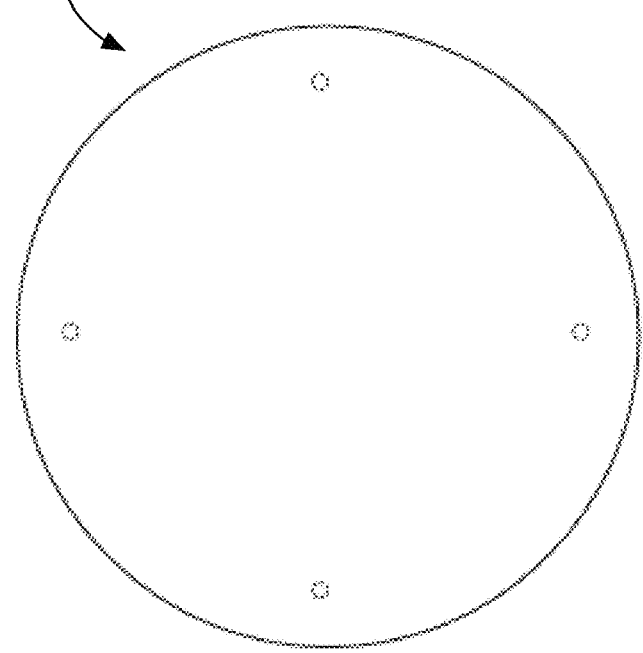
FIG. 12E
FIG. 12F

SYSTEM AND METHOD FOR BREEDING AND HARVESTING INSECTS

CROSS-REFERENCE TO RELATED APPLICATIONS

This application claims the benefit of priority to U.S. Provisional Patent Application No. 62/249,187 filed Oct. 31, 2015, and to PCT Patent Application No. PCT/EP2015/065274 filed Jul. 5, 2015, which claims the benefit of priority to U.S. Provisional Patent Application No. 62/021,111 filed Jul. 5, 2014, the contents of all of which are incorporated herein in their entirety.

FIELD

The specification relates generally to the breeding and harvesting of insects and more particularly to systems and methods for breeding and harvesting insects.

BACKGROUND OF THE DISCLOSURE

Insects are typically raised as a feed for animals such as pets. They have also been raised as a feed for livestock such as fish, poultry and pigs. More recently, "Entomophagy", the human consumption of insects, has become more popular in the Western world. With increased demand for insects for such purposes, there is a need to develop processes and systems to breed and harvest insects.

SUMMARY OF THE DISCLOSURE

Disclosed is a system for producing insects for uses including, but not limited to, human and animal consumption. The system allows the breeding and harvesting of the flour beetle (lat. *Tenebrio Molitor*) and their lifestages.

However, the process or certain parts of the process are not limited to the species and may be applied to other species. The system assists the full lifecycle of the beetles, eggs, larvae and pupae and attempts to automate it on a household scale, with alternative embodiments to upscale for larger production.

One of the main challenges currently in breeding *Tenebrio Molitor* is the following: the larvae ("mealworms") live within their food, their frass and carcasses and other detritus. Once a person desires to harvest the mealworms for themselves or for their pet, the larvae have to be separated from the other lifestages, and from the frass, dirt and carcasses and other detritus. A proposed method includes sieving with different sized sieves, and may additionally or alternatively include vibration, heat and light (in various embodiments), and mechanical agitation combined with sieve structures in order to automate the separation process.

According to some embodiments, there is a system for breeding and harvesting insects. The system includes, but is not necessarily limited to: an egg-producing chamber structure configured to receive insect pupae for pupation and to permit emerged adult insects to mate and oviposit insect eggs, at least one oviposition region in the egg-producing chamber structure configured to receive the insect eggs and apertured to permit at least one of the insect eggs and neonates of the insect eggs to pass therethrough, a larvae-growth chamber in communication with the at least one oviposition region so as to be configured to receive the at least one of the insect eggs and neonates of the insect eggs from the at least one oviposition region, wherein the larvae-growth chamber is further configured to permit the at least one of the insect eggs and neonates of the insect eggs to transition into larvae and to hold feed material for the larvae, a harvesting receptacle in communication with the larvae-growth chamber and at least one inclined surface configured to provide at least a partial passageway for the larvae to travel from the larvae-growth chamber to the harvesting receptacle. at least one oviposition region is provided in at least one nozzle structure; the at least one oviposition region is provided in at least one nozzle structure; the inclined surface comprises a migration ramp connecting the larvae-growth chamber to the harvesting receptacle; the inclined surface comprises an inclined wall portion of the larvae-growth chamber; the inclined wall portion is the peripheral wall of the larvae-growth chamber and provides the at least partial passageway about the entire periphery of the larvae-growth chamber. further comprising an access sleeve coupled to the chamber structure and configured to provide access to a component interior of the egg-producing chamber structure, wherein the access sleeve comprises a material that has a texture sufficient to allow at least one of debris and dead insects within the egg-producing chamber structure to adhere to the access sleeve, wherein the access sleeve is removably coupled to the egg-producing chamber structure.

According to some embodiments, there is a method for breeding and harvesting insects. The method includes, but is not necessarily limited to: providing an egg-producing chamber structure configured to receive insect pupae for pupation and to permit emerged adult insects to mate and oviposit insect eggs, exposing the emerged adult insects to light including at least one wavelength of light conducive to mating between the emerged adult insects, receiving the insect eggs in at least one oviposition region of the egg-producing chamber structure, providing a larvae-growth chamber in communication with the at least one oviposition region so as to be configured to receive at least one of the insect eggs and neonates of the insect eggs from the at least one oviposition region, wherein the larvae-growth chamber is configured to permit the at least one of the insect eggs and neonates of the insect eggs to transition into larvae and is configured to hold feed material for the larvae, and providing at least one inclined surface configured to permit the larvae to travel at least partly from the larvae-growth chamber to a harvesting receptacle.

According to some embodiments, there is a system for breeding and harvesting insects. The system includes, but is not necessarily limited to: an egg-producing chamber structure configured to receive insect pupae for pupation and to permit emerged adult insects to mate and oviposit insect eggs, at least one oviposition region in the egg-producing chamber structure configured to receive the insect eggs and apertured to permit at least one of the insect eggs and neonates of the insect eggs to pass therethrough, a larvae-growth chamber in communication with the at least one oviposition region so as to be configured to receive the at least one of the insect eggs and the neonates of the insect eggs from the at least one oviposition region, wherein the larvae-growth chamber is further configured to permit the at least one of the insect eggs and the neonates to transition into larvae and to hold feed material for the larvae, and a harvesting receptacle in communication with the larvae-growth chamber. The larvae-growth chamber includes at least one inclined wall portion configured to provide at least a partial passageway for the larvae to travel from the larvae-growth chamber to the harvesting receptacle.

According to some embodiments, there is a method for breeding and harvesting insects. The method includes, but is not necessarily limited to: providing an egg-producing chamber structure configured to receive insect pupae for pupation and to permit emerged adult insects to mate and oviposit insect eggs, exposing the emerged adult insects to light including at least one wavelength of light conducive to mating between the emerged adult insects, receiving the insect eggs in at least one oviposition region of the egg-producing chamber structure, and providing a larvae-growth chamber in communication with the at least one oviposition region so as to be configured to receive at least one of the insect eggs and the neonates of the insect eggs from the at least one oviposition region, wherein the larvae-growth chamber is configured to permit the at least one of the insect eggs and neonates of the insect eggs to transition into larvae and is configured to hold feed material for the larvae, and wherein the larvae-growth chamber includes at least one inclined wall portion configured to provide at least a partial passageway for the larvae to travel from the larvae-growth chamber to a harvesting receptacle.

According to some embodiments, there is a system for breeding and harvesting insects. The system includes, but is not necessarily limited to: an egg-producing chamber structure configured to receive insect pupae for pupation and to permit emerged adult insects to mate and oviposit insect eggs, at least one oviposition region in the egg-producing chamber structure configured to receive the insect eggs and apertured to permit at least one of the insect eggs and neonates of the insect eggs to pass therethrough, a larvae-growth chamber in communication with the at least one oviposition region so as to be configured to receive the at least one of the insect eggs and neonates of the insect eggs from the at least one oviposition region, wherein the larvae-growth chamber is further configured to permit the at least one of the insect eggs and neonates of the insect eggs to transition into larvae and to hold feed material for the larvae, and a harvesting receptacle in communication with the larvae-growth chamber. The larvae-growth chamber includes an inclined wall configured to provide at least a partial passageway for the larvae to travel from the larvae-growth chamber to the harvesting receptacle, and the inclined wall provides the at least partial passageway about the entire periphery of the larvae-growth chamber.

According to some embodiments, there is a system for breeding and harvesting insects. The system includes, but is not necessarily limited to: an egg-producing chamber structure configured to receive insect pupae for pupation and to permit emerged adult insects to mate and oviposit insect eggs, the egg-producing chamber structure including a pupation chamber having at least one aperture configured to allow the emerged adult insects to exit the pupation chamber, at least one oviposition region in the egg-producing chamber structure configured to receive the insect eggs and apertured to permit at least one of the insect eggs and neonates of the insect eggs to pass therethrough, a larvae-growth chamber in communication with the at least one oviposition region so as to be configured to receive the at least one of the insect eggs and neonates of the insect eggs from the at least one oviposition region, wherein the larvae-growth chamber is further configured to permit the at least one of the insect eggs and neonates of the insect eggs to transition into larvae and to hold feed material for the larvae, a harvesting receptacle in communication with the larvae-growth chamber and a light source interior to the pupation chamber configured to expose the emerged adult insects to light including at least one wavelength of light conducive to mating between the emerged adult insects. The larvae-growth chamber includes at least one inclined wall portion configured to provide at least a partial passageway for the larvae to travel from the larvae-growth chamber to the harvesting receptacle.

According to some embodiments, there is a system for breeding and harvesting insects. The system includes, but is not necessarily limited to: an egg-producing chamber structure configured to receive insect pupae for pupation and to permit emerged adult insects to mate and oviposit insect eggs, at least one oviposition region in the egg-producing chamber structure configured to receive the insect eggs and apertured to permit at least one of the insect eggs and neonates of the insect eggs to pass therethrough, a larvae-growth chamber in communication with the at least one oviposition region so as to be configured to receive the at least one of the insect eggs and neonates of the insect eggs from the at least one oviposition region. The larvae-growth chamber is further configured to permit the at least one of the insect eggs and neonates of the insect eggs to transition into larvae and to hold feed material for the larvae and a harvesting receptacle in communication with the larvae-growth chamber. The larvae-growth chamber includes at least one inclined wall portion configured to provide at least a partial passageway for the larvae to travel from the larvae-growth chamber to the harvesting receptacle. The egg-producing chamber structure includes at least one one-way exit structure configured to permit adult insects which emerge in the larvae-growth chamber to exit the larvae-growth chamber into the egg-producing chamber structure and to inhibit the adult insects which emerge in the larvae-growth chamber from re-entering the larvae-growth chamber through the at least one one-way exit structure. at least one of the at least one one-way exit structure is a one-way exit nozzle structure.

According to some embodiments, there is a system for breeding and harvesting insects. The system includes, but is not necessarily limited to: an egg-producing chamber structure configured to receive insect pupae for pupation and to permit emerged adult insects to mate and oviposit insect eggs, at least one oviposition region in the egg-producing chamber structure configured to receive the insect eggs and apertured to permit at least one of the insect eggs and neonates of the insect eggs to pass therethrough, a larvae-growth chamber in communication with the at least one oviposition region so as to be configured to receive the at least one of the insect eggs and neonates of the insect eggs from the at least one oviposition region, wherein the larvae-growth chamber is further configured to permit the at least one of the insect eggs and neonates of the insect eggs to transition into larvae and to hold feed material for the larvae, a harvesting receptacle in communication with the larvae-growth chamber. The larvae-growth chamber includes at least one inclined wall portion configured to provide at least a partial passageway for the larvae to travel from the larvae-growth chamber to the harvesting receptacle via a larvae exit aperture. The larvae-growth chamber includes a larvae exit plug sized to engage the larvae exit aperture and to prevent the larvae from exiting the larvae-growth chamber via the larvae exit aperture.

According to some embodiments, there is a system for breeding and harvesting insects. The system includes, but is not necessarily limited to: an egg-producing chamber structure configured to receive insect pupae for pupation and to permit emerged adult insects to mate and oviposit insect eggs, the egg-producing chamber structure including a pupation chamber having at least one aperture configured to allow the emerged adult insects to exit the pupation chamber, at least one oviposition region in the egg-producing chamber structure configured to receive the insect eggs and apertured to permit at least one of the insect eggs and neonates of the insect eggs to pass therethrough, a larvae-growth chamber in communication with the at least one oviposition region so as to be configured to receive the at least one of the insect eggs and neonates of the insect eggs from the at least one oviposition region, wherein the larvae-growth chamber is further configured to permit the at least one of the insect eggs and neonates of the insect eggs to transition into larvae and to hold feed material for the larvae and a harvesting receptacle in communication with the larvae-growth chamber. The larvae-growth chamber includes at least one inclined wall portion configured to provide at least a partial passageway for the larvae to travel from the larvae-growth chamber to the harvesting receptacle. The pupation chamber includes a nutrient compartment configured to hold at least one of a hydrating fluid, a pad and a cloth impregnated with the hydrating fluid to hydrate the adult emerged insects.

According to some embodiments, there is a system for breeding and harvesting insects. The system includes, but is not necessarily limited to: an egg-producing chamber structure configured to receive insect pupae for pupation and to permit emerged adult insects to mate and oviposit insect eggs, at least one oviposition region in the egg-producing chamber structure configured to receive the insect eggs and apertured to permit at least one of the insect eggs and neonates of the insect eggs to pass therethrough, a larvae-growth chamber in communication with the at least one oviposition region so as to be configured to receive the at least one of the insect eggs and neonates of the insect eggs from the at least one oviposition region, wherein the larvae-growth chamber is further configured to permit the at least one of the insect eggs and neonates of the insect eggs to transition into larvae and to hold feed material for the larvae, a harvesting receptacle in communication with the larvae-growth chamber, a waste receptacle in communication with the larvae-growth chamber via at least one waste aperture, and a filter device included in the at least one waste aperture and configured to filter excess fluids in waste material passing through the at least one waste aperture while preventing at least one of the larvae from travelling from the larvae-growth chamber to the waste receptacle through the at least one waste aperture. The larvae-growth chamber includes at least one inclined wall portion configured to provide at least a partial passageway for the larvae to travel from the larvae-growth chamber to the harvesting receptacle.

According to some embodiments, there is a system for breeding and harvesting insects. The system includes, but is not necessarily limited to: an egg-producing chamber structure configured to receive insect pupae for pupation and to permit emerged adult insects to mate and oviposit insect eggs, at least one oviposition region in the egg-producing chamber structure configured to receive the insect eggs and apertured to permit at least one of the insect eggs and neonates of the insect eggs to pass therethrough, a larvae-growth chamber in communication with the at least one oviposition region so as to be configured to receive the at least one of the insect eggs and neonates of the insect eggs from the at least one oviposition region, wherein the larvae-growth chamber is further configured to permit the at least one of the insect eggs and neonates of the insect eggs to transition into larvae and to hold feed material for the larvae, at least one inclined surface configured to provide at least a partial passageway for the larvae to travel from the larvae-growth chamber to a harvesting receptacle in communication with the larvae-growth chamber.

According to some embodiments, there is a system for breeding and harvesting insects. The system includes, but is not necessarily limited to: At least one egg-producing chamber structure configured to receive insect pupae for pupation and to permit emerged adult insects to mate and oviposit insect eggs; at least one oviposition region in the egg-producing chamber structure configured to receive the insect eggs and apertured to permit at least one of the insect eggs and neonates of the insect eggs to pass therethrough; at least one larvae-growth chamber in communication with the at least one oviposition region so as to be configured to receive the at least one of the insect eggs and neonates of the insect eggs, wherein the larvae-growth chamber is further configured to permit the at least one of the insect eggs and neonates of the insect eggs to transition into larvae and to hold feed material for the larvae; a harvesting receptacle positioned to hold larvae; at least one inclined surface positioned to receive larvae from the larvae-growth chamber, and a passageway for the larvae to travel to the harvesting receptacle.

According to some embodiments, there is a system for breeding and harvesting insects. The system includes, but is not necessarily limited to: an egg-producing chamber structure configured to receive insect pupae for pupation and to permit emerged adult insects to mate and oviposit insect eggs; at least one oviposition region in the egg-producing chamber structure configured to receive the insect eggs and apertured to permit at least one of the insect eggs and neonates of the insect eggs to pass therethrough; at least one larvae-growth chamber in communication with the at least one oviposition region so as to be configured to receive the at least one of the insect eggs and neonates of the insect eggs from the at least one oviposition region, wherein the larvae-growth chamber is further configured to permit the at least one of the insect eggs and neonates of the insect eggs to transition into larvae and to hold feed material for the larvae; and a harvesting receptacle positioned to hold larvae; and a larvae reception surface positioned to receive larvae from the larvae-growth chamber and provide passageway for the larvae to travel to the harvesting receptacle;
at least one larvae motivation element selected from the group of larvae motivation elements consisting of: a heat element, a vibration element and a light element, wherein the at least one larvae motivation element is positioned and activated to act on larvae to urge the larvae to leave a larvae reception surface via the passageway.

According to some embodiments, there is a system for breeding and harvesting insects. The system includes, but is not necessarily limited to: an egg-producing chamber structure configured to receive insect pupae for pupation and to permit emerged adult insects to mate and oviposit insect eggs, the egg-producing chamber structure including a pupation chamber having at least one aperture configured to allow the emerged adult insects to exit the pupation chamber; at least one oviposition region in the egg-producing chamber structure configured to receive the insect eggs and apertured to permit at least one of the insect eggs and neonates of the insect eggs to pass therethrough; a larvae-growth chamber in communication with the at least one oviposition region so as to be configured to receive the at least one of the insect eggs and neonates of the insect eggs from the at least one oviposition region, wherein the larvae-growth chamber is further configured to permit the at least one of the insect eggs and neonates of the insect eggs to transition into larvae and to hold feed material for the larvae; a harvesting receptacle positioned to hold larvae; and a light source interior to the pupation chamber configured to expose the emerged adult insects with light including at least one wavelength of light conducive to mating between the emerged adult insects; at least one receptacle surface configured to receive larvae from larvae-growth chambers and to provide a passageway for the larvae to travel to the harvesting receptacle; a microclimate control system, which includes: a heat source, a light source, a fan, a temperature and humidity sensor which monitors the temperature and humidity in the at least one larvae-growth chamber, and a control sub-system programmed to control a microclimate in the at least one larvae-growth chamber, using the heat source, the light source, the sensor, and the fan.

It will be noted that the term "growth chamber tray" may be used as an example of a "larvae-growth chamber". The term "harvest tray" may be used as an example of a "harvest receptacle". The term "oviposition inlay" may be used as an example of an "egg-producing chamber structure", the area except the pupation area in the oviposition inlay corresponding to an "oviposition region". The term "pupation area" may be used as an example of a "pupation chamber". The term "harvest plate" may be used as an example of a "harvest receptacle surface" and may include an "inclined surface/wall".

In another aspect, a system is provided for breeding and harvesting insects, including an egg-producing chamber structure configured to receive insect pupae for pupation and to permit emerged adult insects to mate and oviposit insect eggs, at least one oviposition region in the egg-producing chamber structure configured to receive the insect eggs and apertured to permit at least one of the insect eggs and neonates of the insect eggs to pass therethrough, at least one larvae-growth chamber in communication with the at least one oviposition region so as to be configured to receive the at least one of the insect eggs and neonates of the insect eggs, wherein the larvae-growth chamber is further configured to permit the at least one of the insect eggs and neonates of the insect eggs to transition into larvae and to hold feed material for the larvae, a separation area positioned to hold larvae, and detritus from the at least one larvae growth chamber, a harvesting receptacle positioned to hold larvae, a passageway for the larvae to travel from the separation area to the harvesting receptacle, at least one larvae motivation element selected from the group of larvae motivation elements consisting of: a heat element, a vibration element and a light element, and mechanical agitator, wherein the at least one larvae motivation element is positioned and activated to act on larvae to urge the larvae to leave the separation area and enter the passageway.

BRIEF DESCRIPTIONS OF THE DRAWINGS

For a better understanding of the various embodiments described herein and to show more clearly how they may be carried into effect, reference will now be made, by way of example only, to the accompanying drawings in which:

FIG. 3 depicts a side elevation view of a cross-section of the system for breeding and harvesting insects in FIG. 1 A, showing a light source configured to provide light including a wavelength of light conducive to mating between adult insects, according to non-limiting embodiments;

FIGS. 4A to 4C depict a top view, perspective view and side view of a nozzle structure including an oviposition region, according to non-limiting embodiments;

FIGS. 6A to 6C depict side cross-section views of pupation chambers, according to non-limiting embodiments;

FIG. 6D depicts a perspective cross-section view of the pupation chamber shown in FIG. 6C, according to non-limiting embodiments;

FIG. 7 depicts an exploded view of the system for breeding and harvesting insects in FIG. 1A, according to non-limiting embodiments;

FIG. 12B depicts a side, cross-section view of the system for breeding and harvesting insects in FIG. 10 showing at least one oviposition region including a mesh structure, according to a second set of non-limiting embodiments;

FIG. 12C depicts a top plan view of an oviposition region of 12B including the mesh structure, according to a second set of non-limiting embodiments;

FIG. 12D depicts a side, cross-section view of the oviposition region shown in FIG. 12C, according to a second set of non-limiting embodiments;

FIG. 12E depicts a top elevation view of an pair of oviposition plates, according to non-limiting embodiments;

FIG. 12F depicts a side elevation view of the pair of oviposition plates shown in FIG. 12 E, according to non-limiting embodiments;

DETAILED DESCRIPTION

Figure 1A:
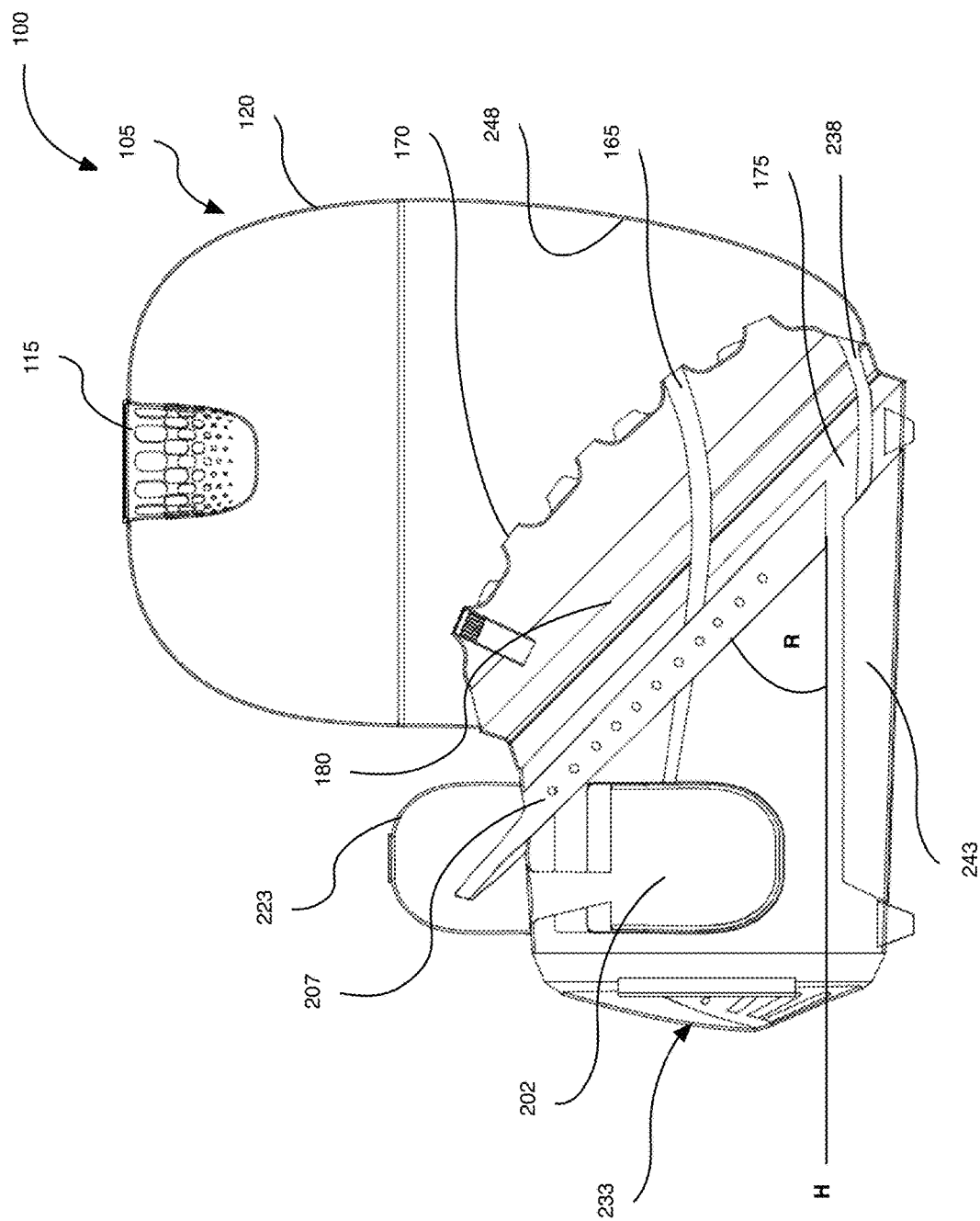
FIG. 1A depicts a side elevation view of a cross-section of a system for breeding and harvesting insects, according to non-limiting embodiments.
Figure 1B:
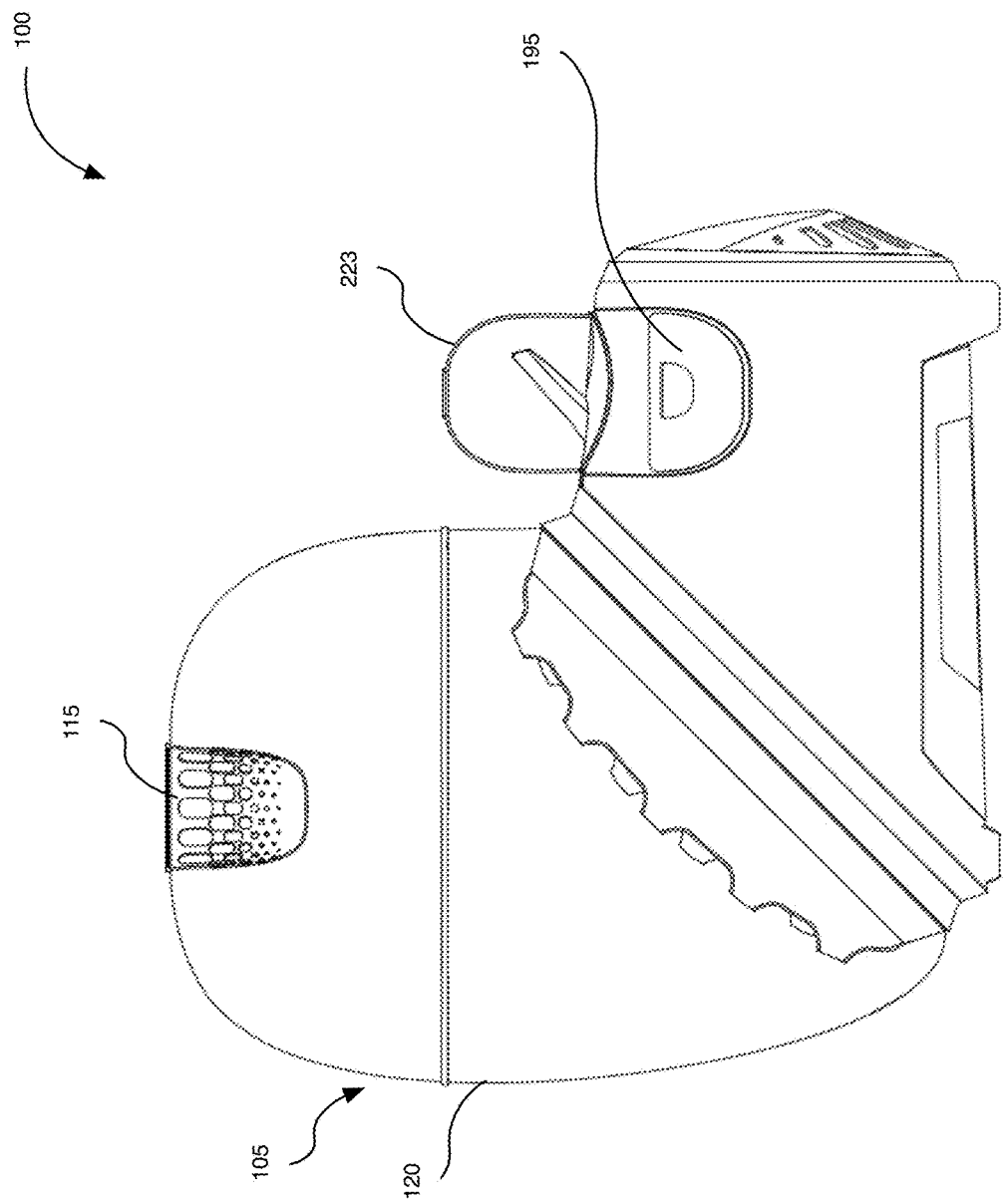
FIG. 1B depicts a side elevation view of the system for breeding and harvesting insects in FIG. 1A, according to non-limiting embodiments.

Described herein are systems and methods for breeding insects for, but not limited to, human as well as animal consumption. The systems and methods allow for the breeding and harvesting of the black soldier fly, also known as *Hermetia illucens*, and their larvae; the systems and methods also allow for breeding and harvesting flour beetle (*Tenebrio molitor*) and its eggs, larvae and pupae. However, the systems and methods are not limited to this insect species and, according to some embodiments, may be applied to other insect species.

The described systems and methods facilitates the full lifecycle of the insects and their larvae, and attempts to automate the lifecycle on a household scale, with some embodiments capable of being scaled up for larger production.

It is understood that for the purpose of this disclosure, language of "at least one of X, Y, and Z" and "one or more of X, Y and Z" can be construed as X only, Y only, Z only, or any combination of two or more items X, Y, and Z (e.g., XYZ, XYY, YZ, ZZ).

It is also understood that the terms "couple", "coupled", "connect", "connected" are not limited to direct mating between the described components, but also contemplate the use of intermediate components to achieve the connection or coupling.

The device may be made from any suitable materials, including synthetic materials, ceramic materials, metal materials, composite materials, or any suitable combination thereof.

FIGS. 1A to 8 depict an example system 100 for breeding and harvesting insects. The system 100 is at least partially enclosed and can be used to breed and harvest black soldier flies and their larvae. In some embodiments, the system 100 is used for breeding and harvesting other insect species.

The system 100 includes an egg-producing chamber structure 105 that is configured to receive insect pupae, such pupae 110 (FIG. 3), for pupation and to permit emerged adult insects to mate and oviposit insect eggs. The egg-producing chamber structure 105 may be any suitable shape and size. The egg-producing chamber structure 105 can include one or more chambers. In some embodiments, multiple insect lifecycle stages are at least started in the same chamber. In some embodiments, one or more of insect lifecycle stages are performed in separate chambers. For example, system 100 includes a pupation chamber 115 and a mating and oviposition chamber 120. The pupae 110 and prepupae (also referred to herein as "premature prepupae") are placed into the pupation chamber 115 in order to emerge as adult insects. The insect lifecycle can be started and restarted in the pupation chamber 115. The emerged adult insects can then move into the mating and oviposition chamber 120 to mate and oviposit insect eggs. Particular features of the pupation chamber 115 and the mating and oviposition chamber 120 are described further below.

The egg-producing chamber structure 105 includes at least one egg-laying or oviposition region 125 (FIG. 2A) that is configured to receive the insect eggs and is apertured to permit at least one of the insect eggs and neonates of the insect eggs to pass therethrough. For example, in some embodiments, the at least one oviposition region 125 is included in at least one nozzle structure 130 (FIG. 2A) in the egg-producing chamber structure 105. However, any suitable location for the oviposition region 125 in the egg-producing chamber structure 105 is contemplated. The oviposition region 125 can take any suitable configuration that is apertured to permit at least one of the insect eggs and the neonates of the insect eggs to pass through. For example, the oviposition region 125 can include at least one egg-receiving aperture 135 (FIGS. 4A to 4C) sized to allow at least one of the insect eggs and the neonates of the insect eggs to pass through. For example, the oviposition region 125 can be formed as a perforated solid structure, shown in FIGS. 4A to 4C (as a membrane 140 interior of the nozzle structure 130). As another example, the oviposition region 125 can include at least one mesh structure. An example mesh structure is shown in FIGS. 12B to 12D and is described further below. In some embodiments, the oviposition region 125 is removable from the egg-producing chamber structure 105 to, for example, clean the oviposition region 125.

FIGS. 6A to 6D show three examples of the pupation chamber 115: a pupation chamber 115A, a pupation chamber 115B and a pupation chamber 115C. The pupation chamber 115 can include at least one aperture configured to allow the emerged adult insects to exit the pupation chamber 115. In FIG. 6A, the pupation chamber 115A includes a plurality of holes, including exit holes 145, that are sized for an emerged adult insect to pass through. The pupation chamber 115A also includes aerating holes 150 that are sized (i.e., small enough) to keep the prepupae and pupae in the pupation chamber 115A while allowing at least some airflow into the pupation chamber 115. The exit holes 145 are located above the aerating holes 150 such that, in the case of flying insects, the adult emerged insects can fly out of the pupation chamber 115A. The exit holes 145 and the aeration holes 150 may be shaped in any suitable manner. For example, the exit holes 145 and the aeration holes 150 can be rounded-rectangular, round, elliptical, squared, an organic, free-form shape and any combination of suitable shapes. In the pupation chamber 115B (FIG. 6B), the plurality of holes is replaced by at least one larger exit hole 155 that is positioned at a distance, D, away from the bottom surface, B, of the pupation chamber 115B to help prevent the pupae and prepupae from escaping from the pupation chamber 115B while permitting the emerged adult insects to leave the pupation chamber 115B (e.g., by flying out of the pupation chamber 115B). The distance, D, can be determined based on a desired number of pupae and/or prepupae the pupation chamber 115B will hold. In some embodiments, the desired number of pupae and/or prepupae the pupation chamber 115B will hold is approximately 10 percent of the larvae harvested, which may be about 50 to 100 g per week. Some freshly emerged adult insects may not immediately remove their pupal cases or have difficulty removing their pupal cases. The pupation chamber 115C includes at least one tapered exit hole 146 configured to engage with at least one of the emerged adult insects to assist in the removal of the pupal case as the emerged adult insect(s) exit the pupation chamber 115. For example, the exit holes 146 are tapered such that the inlet 149 has a smaller cross-sectional area than the outlet 156 (i.e., tapered towards the inlet 149), with the inlet 149 being sized to engage with and assist in the removal the pupal case. In some embodiments, the exit holes 146 are tapered such that the outlet 156 is sized to engage with and assist in the removal the pupal case and has a smaller cross-section than the inlet 149 (i.e., tapered towards the outlet 156). Removal of the pupal cases before the emerged adult insects enter the mating and oviposition chamber 120 may help reduce the amount of dirt and debris in the mating and oviposition chamber 120.

The pupation chamber 115 may have a cover or top, such as cover 160 (FIGS. 6A, 6B). The cover 160 can be a mesh structure, a plastic structure or any other suitable covering for the pupation chamber 115. The pupation chamber 115 may be any suitable shape and manufactured from any suitable material or combination of materials. As soon as the prepupae and/or the pupae emerge as adult insects, they seek their way out of the pupation chamber 115 into the mating and oviposition chamber 120.

The adult emerged insects, such as black soldier flies, will spend their adult lifecycle (fly stadium) in the mating and oviposition chamber 120. The mating and oviposition chamber 120 is in communication with the pupation chamber 115 such that the emerged adult insects can exit the pupation chamber and reach the mating and oviposition chamber 120. In the example system 100, the emerged adult insects are able to exit the pupation chamber 115, through the exit holes 145, for example, directly into the mating and oviposition chamber 120. However, in some embodiments, there is at least one intermediary structure between the pupation chamber 115 and the mating and oviposition chamber 120 which is configured for the emerged adult insects to travel through to reach the mating and oviposition chamber 120.

Figure 5:
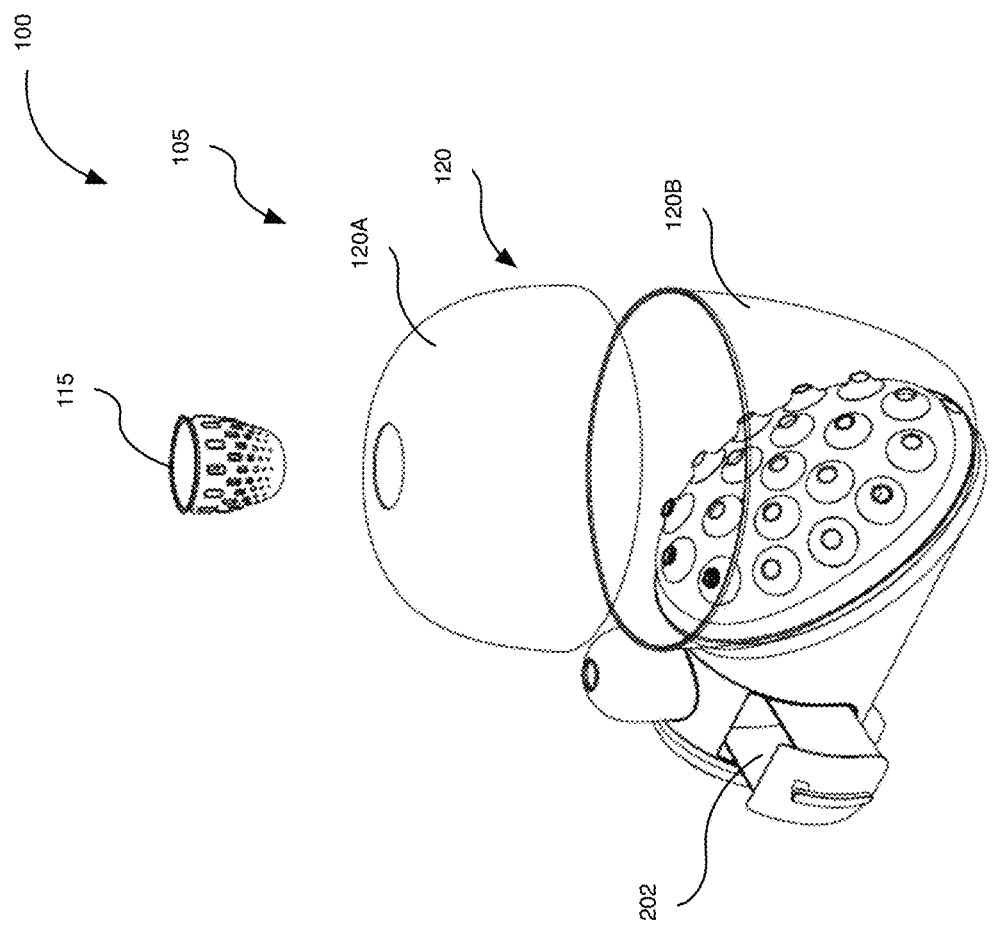
FIG. 5 depicts a partially exploded, perspective view of the system for breeding and harvesting insects in FIG. 1A, according to non-limiting embodiments.

The mating and oviposition chamber 120 take a variety of shapes and can be manufactured from a variety of materials. For example, the mating and oviposition chamber 120 can be generally hemispheric in shape or egg-shaped. For easier access to the interior of the mating and oviposition chamber 120 (e.g., for cleaning or other maintenance), the mating and oviposition chamber 120 may be separable into two or more sections, as shown in FIG. 5 (sections 120A, 120B). The mating and oviposition chamber 120 may be manufactured from any suitable material, such as glass, plastic or plexiglass. The mating and oviposition chamber 120 may be fully or partially transparent, or fully opaque. In some embodiments, a coating or a film (such as an ultraviolet filter film) may be applied to the mating and oviposition chamber 120. The mating and oviposition chamber 120 may be manufactured from a solid material, which may help contain odours from the larvae colony in the larvae-growth chamber 175 (described below) within the system 100. In some embodiments, seals are provided between one or more of the pupation chamber 115, the mating and oviposition chamber 120 and the larvae-growth chamber 175 to help contain odours from the larvae colony.

Some insects visually inspect other adult insects to identify adult male insects and adult female insects for the purposes of mating. In order to aid in mating between the emerged adult insects, in some embodiments, the system 100 includes a light source 253 configured to expose the emerged adult insects with light including the at least one wavelength of light 258 conducive to mating between the emerged adult insects (FIG. 3). According to some studies, wavelengths of light in the visible spectrum, such as in the range of 450 to 700 nm, may be conducive to mating activity (see "An Artificial Light Source Influences Mating and Oviposition of Black Soldier Flies, *Hermetia Illucens*", Zhang et al., Journal of Insect Science: Vol. 10, Article 202). In the Applicant's own testing, wavelengths of light within the ultraviolet spectrum, such as wavelengths of light between 290 and 320 nm in the ultraviolet-B spectrum ("UVB"), have also been found to be conducive to mating between the emerged adult insects.

In some embodiments, the light source 253 is ambient to the egg-producing chamber structure 105 and at least the mating and the oviposition chamber 120 is configured to transmit light including the at least one wavelength of light 258 into the mating and oviposition chamber 120. For example, the light source 253 can be the Sun, S, that transmits light including the wavelength of light 258, such as the full spectrum of sunlight, and the mating and oviposition chamber 120 can be manufactured from a material that permits light including the at least the wavelength of light 258 from the Sun, S, to be transmitted into the mating and oviposition chamber 120, such as glass, an ultra-violet light transmissive plexiglass or a netting material (FIG. 3). The mating and oviposition chamber 120 may also include one or more apertures to permit light including the at least the wavelength of light 258 from the Sun, S, to be transmitted into the mating and oviposition chamber 120. In some embodiments, the light sources 253 is an artificial light source, such as a lamp, configured to provide artificial light including the wavelength of light 258. In some embodiments, the artificial light source is located interior of the egg-producing chamber structure 105. At least one example embodiment that includes an artificial light source located interior of the egg-producing chamber structure 105 is described further below.

As described above, the mating and oviposition chamber 120 can include nozzle structures 130 having the oviposition region 125. Although the example system 100 is shown with three such nozzle structures 130, some embodiments include one or two nozzle structures 130 and some other embodiments include three or more nozzle structures. The egg-receiving apertures 135 can be a variety of suitable sizes and shapes. For example, in some embodiments, the egg-receiving apertures 135 are circular in shape and have diameters ranging from approximately two millimeters to four millimeters. In some embodiments, the egg-receiving apertures 135 are elliptical, square, organic, free-formed in shape or any combination thereof. The nozzle structures 130 can be arranged in any suitable manner in the mating and oviposition chamber 120.

Figure 2A:
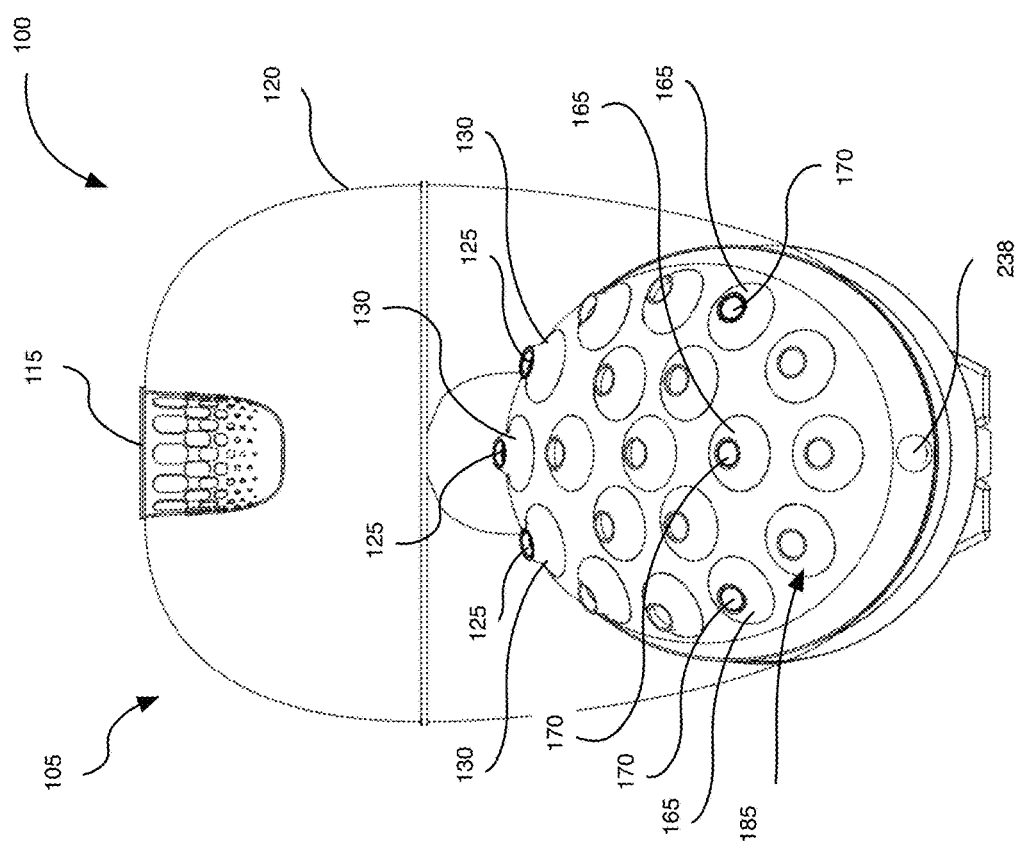
FIG. 2A depicts a front elevation view of the system for breeding and harvesting insects in FIG. 1A, according to non-limiting embodiments.
Figure 2B:
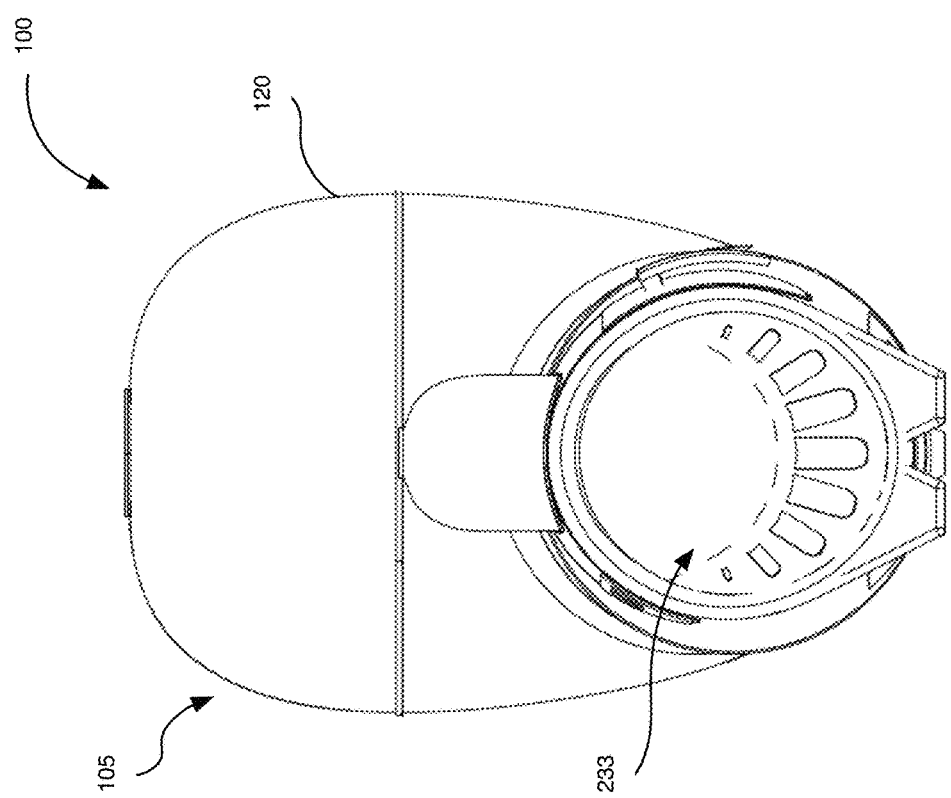
FIG. 2B depicts a rear elevation view of the system for breeding and harvesting insects in FIG. 1A, according to non-limiting embodiments.

The emerged adult insects may not feed on solid substances. For example, adult black soldier flies nurture themselves with a hydrating fluid, such as water or a mixture of sugar and water. The system 100 can include at least one structure configured to provide a hydrating fluid to the emerged adult insects, such as hydrating nozzles 165 (FIG. 2A). The hydrating nozzles 165 can be connected to a hydrating fluid source (not shown) and configured to provide the hydrating fluid to the emerged adult insects in a number of ways. For example, the hydrating nozzles 165 may provide small ponds of hydrating fluid for the adult emerged insects to drink from. In another embodiment, the hydrating nozzles 165 may be jet nozzles configured to provide the emerged adult insects with nebulized water.

Additional nozzles, such as general nozzles 185 can also be included. The general nozzles 185 can provide additional vents for airflow between the mating and oviposition chamber 120 and the larvae-growth chamber 175 to help stimulate oviposition (described further below).

The nozzles structures 135, hydrating nozzles 165 and general nozzles 185 can take any suitable shape. As shown in FIG. 2A, the nozzles structures 135, hydrating nozzles 165 and general nozzles 185 have outlets that are round or circular in shape. However, in some embodiments, the nozzles structures 135, hydrating nozzles 165 and general nozzles 185 have outlets that are elliptical, square, organic, free-formed in shape, or any combination thereof.

The insect eggs and neonates of the insect eggs pass through the oviposition region 125 into a larvae-growth chamber 175 (FIGS. 1A, 3 and 7). The larvae-growth chamber 175 is in communication with the oviposition region 125 so as to be configured to receive the insect eggs and/or the neonates of the insect eggs from the oviposition region 125. For example, the insect eggs and/or neonates of the insect eggs may pass through the egg-receiving apertures 135 into the larvae-growth chamber 175 by gravity (i.e., fall through the receiving apertures 135 into the larvae-growth chamber 175) or push themselves through the egg-receiving apertures 135 to get to the larvae-growth chamber 175, enticed by the smell of the feed material in the larvae-growth chamber 175. The insect eggs may be laid in clusters and stick to the oviposition region 125. In these cases, the insect eggs may hatch in the oviposition region 125 and fall into the larvae-growth chamber 175.

The larvae-growth chamber 175 is configured to permit the insect eggs and/or the neonates of the insect eggs to transition into larvae. For example, the larvae-growth chamber 175 may be around in shape or have at least rounded corners in order for the larvae to grow efficiently. Larvae tend to squeeze into edges and small slots that can reduce the efficiency and activity of the whole colony due to, for example, hot spots. Rounded corners and/or shapes may yield at least three results. Firstly, the rounded corners and/or shapes may permit the larvae to permanently and freely move through the feed material provided for the larvae. Secondly, as the larvae move through the feed material, the larvae aerate the feed material and provide pockets of oxygen for use by the larvae. The aeration can help prevent the larvae from running out of oxygen. Thirdly, rounded corners and/or shapes may lead to improved feed material intake of the larvae, which leads to quicker growth of the larvae and therefore better harvest conditions and quicker digestion of organic waste which the larvae can feed on. The third result may lead to more feed material being processed, reduced odour and a greater number of larvae to harvest.

The larvae can be sensitive to light and prefer darkness. As a result, in some embodiments, the walls of the larvae-growth chamber 135, such as walls 190, can be opaque, semi-opaque or partly opaque. Surface treatments or films may be applied to the walls 190 to achieve the desired light transmissibility.

The larvae-growth chamber 175 is also configured to hold feed material for the larvae. For example, organic waste material to feed the larvae can be deposited into the larvae-growth chamber 175 through the feeding door 195 (FIG. 1B) of the larvae-growth chamber 175. The feed material may also be pre-processed feed or germ plasma. As another example, the larvae-growth chamber 175 may be separable from the egg-producing chamber structure 105 to allow for feed material to be directly deposited into the larvae-growth chamber 175.

The system 100 can also include a nozzle membrane 170 (FIG. 1A) that separates the volumes of the mating and oviposition chamber 120 from the larvae-growth chamber 175. The nozzle membrane 170 may be configured to allow at least air from the larvae-growth chamber 175 to flow through to the mating and oviposition chamber 120, which can stimulate oviposition (egg-laying). For example, the nozzle membrane 170 may have at least one aperture configured to permit airflow therethrough. In some embodiments, the nozzle membrane 170 may be included in at least one of the general nozzles 185. In some embodiments, airflow through the egg-receiving apertures 135 of the oviposition region 125 from the larvae-growth chamber 175 into the mating and oviposition chamber 120 may be sufficient to stimulate oviposition and the nozzle membrane 170 can be omitted. Hence, in some embodiments, the oviposition region 125 may perform multiple functions, including providing a site for oviposition, providing a mechanism to transport the insect eggs and/or neonates of the insect eggs to the larvae-growth chamber 175 without direct human intervention, and to permit airflow from the larvae-growth chamber 175 to the egg-producing chamber structure 105 (e.g., to the mating and oviposition chamber 120) to help stimulate oviposition.

An interior membrane 180 (FIGS. 1A, 7) between the nozzle membrane 170 and the larvae-growth chamber 175 may be provided to prevent larvae from crawling out of the larvae-growth chamber 175 through the nozzle structures 130, hydrating nozzles 165 or the general nozzles 185. The interior membrane 180 may be a mesh structure or perforated solid structure with suitably sized apertures to allow air to flow from the larvae-growth chamber 175 through the nozzle structures 130, hydrating nozzles 165 and/or the general nozzles 185 without allowing the larvae to pass through. An additional, secondary membrane 182 (FIG. 7) can be included to prevent larvae from crawling through to the mating and oviposition chamber 120 through any of the nozzle structures 135, hydrating nozzles 165 and general nozzles 185. The secondary membrane 182 is configured to allow the insect eggs and/or neonates of the insect eggs to fall into the larvae-growth chamber 175 through the oviposition region 125. For example, in some embodiments, the secondary membrane 182 is sized to leave at least a portion of the larvae-growth chamber 175 in communication with the oviposition region 125.

Figure 14:
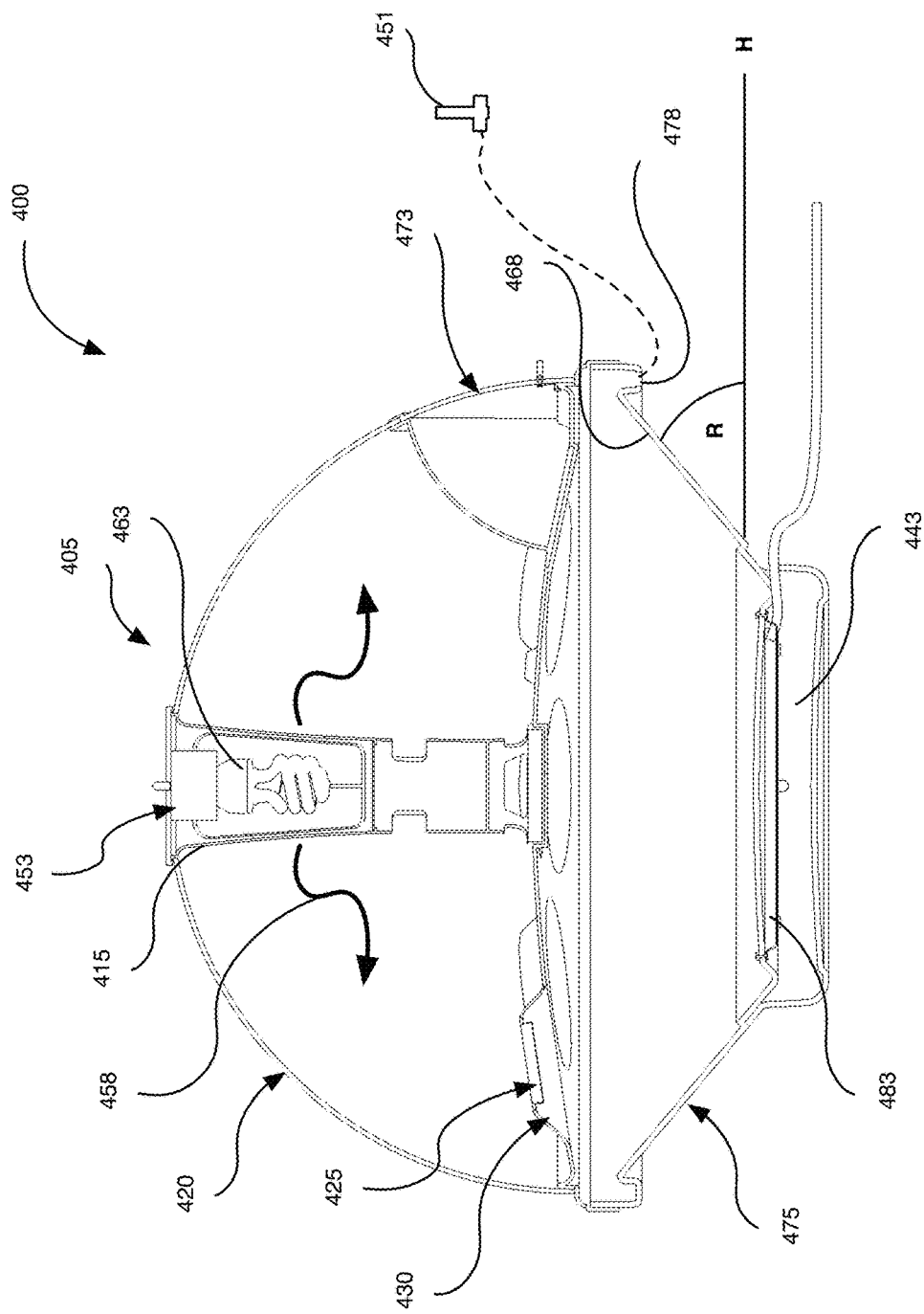
FIG. 14 depicts a side, cross-section view of the system for breeding and harvesting insects in FIG. 10, according to a second set of non-limiting embodiments.
Figure 15A:
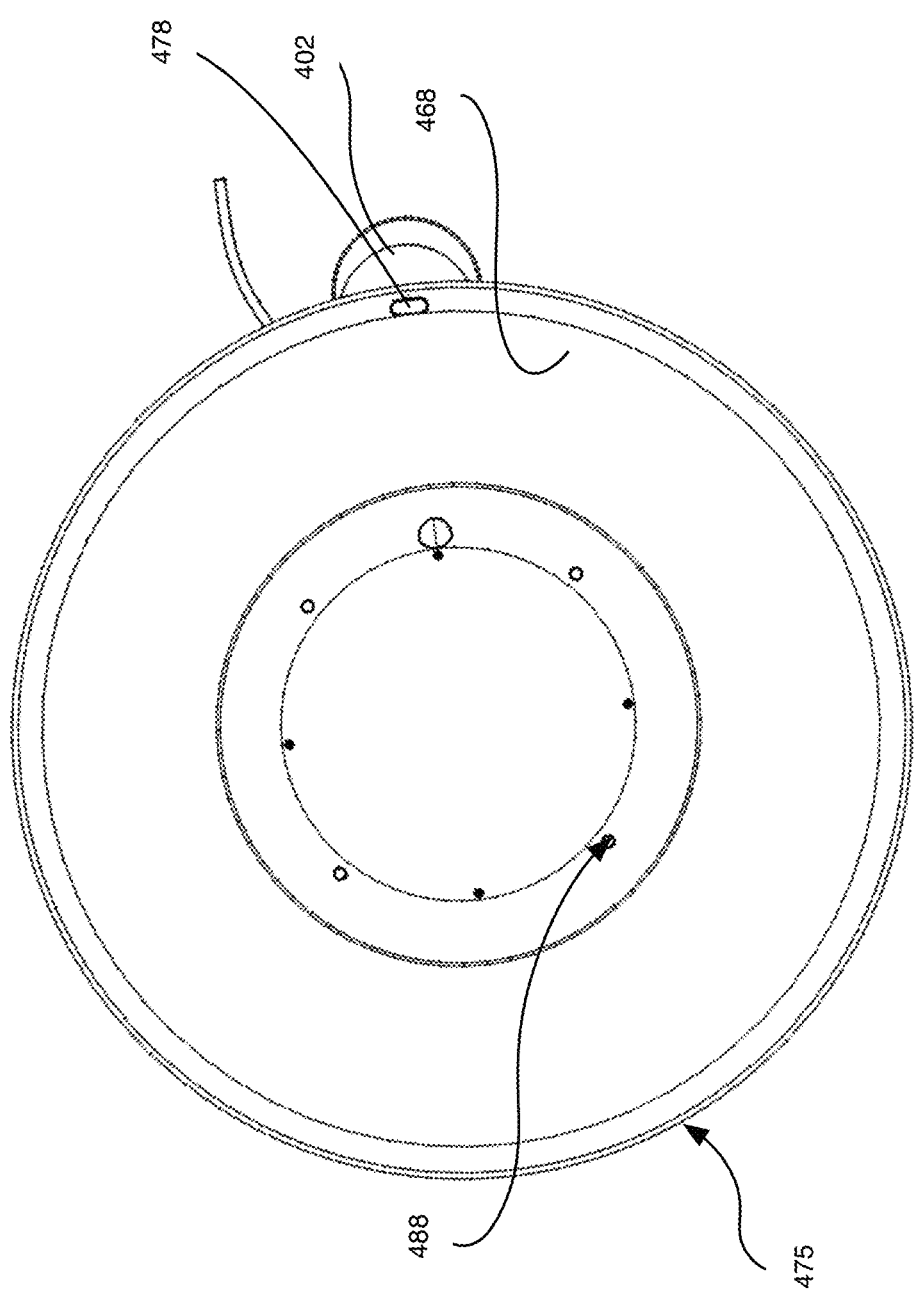
FIG. 15A depicts a top plan view of a larvae-growth chamber, according to a second set of non-limiting embodiments.
Figure 15C:
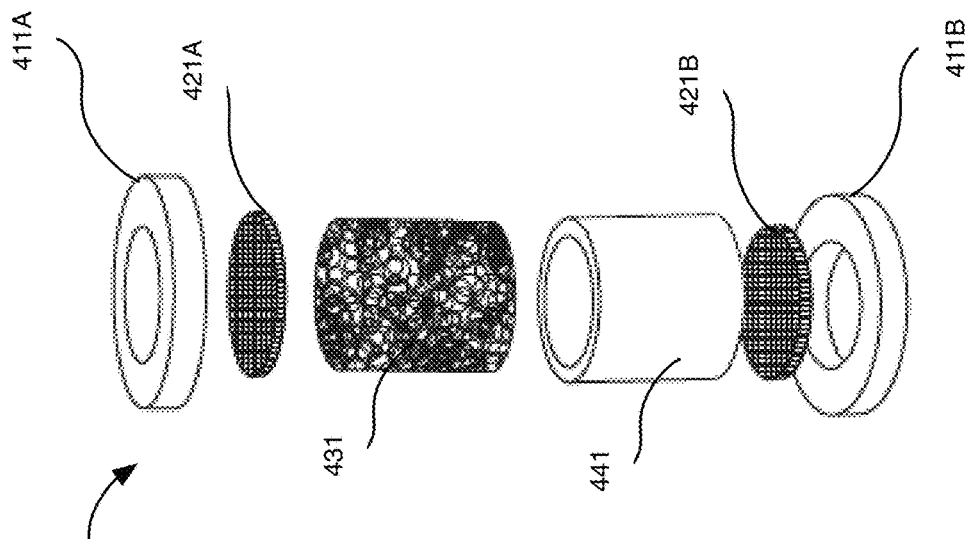
FIG. 15C depicts an exploded view of the filter cylinder shown in FIG. 15B, according to non-limiting embodiments.
Figure 15B:
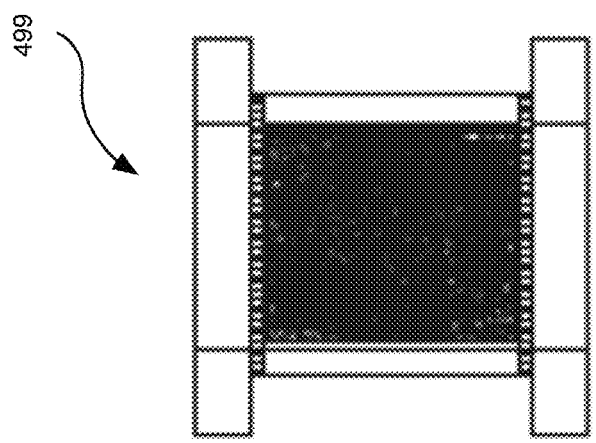
FIG. 15B depicts a filter cylinder for filtering waste fluids from the larvae-growth chamber to the waste receptacle, according to non-limiting embodiments.
Figure 16A:
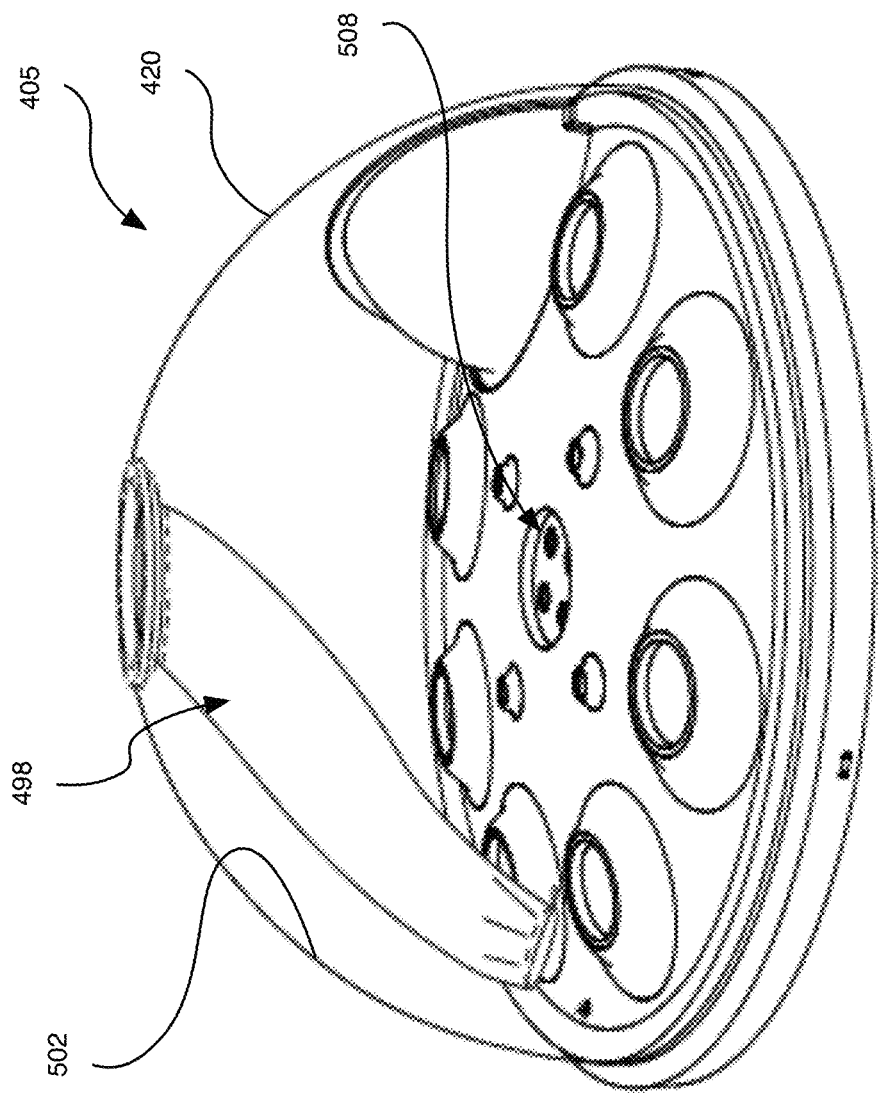
FIG. 16A depicts a perspective view of the mating and oviposition chamber shown in FIG. 10 including a cleaning sleeve, according to a second set of non-limiting embodiments.
Figure 16B:
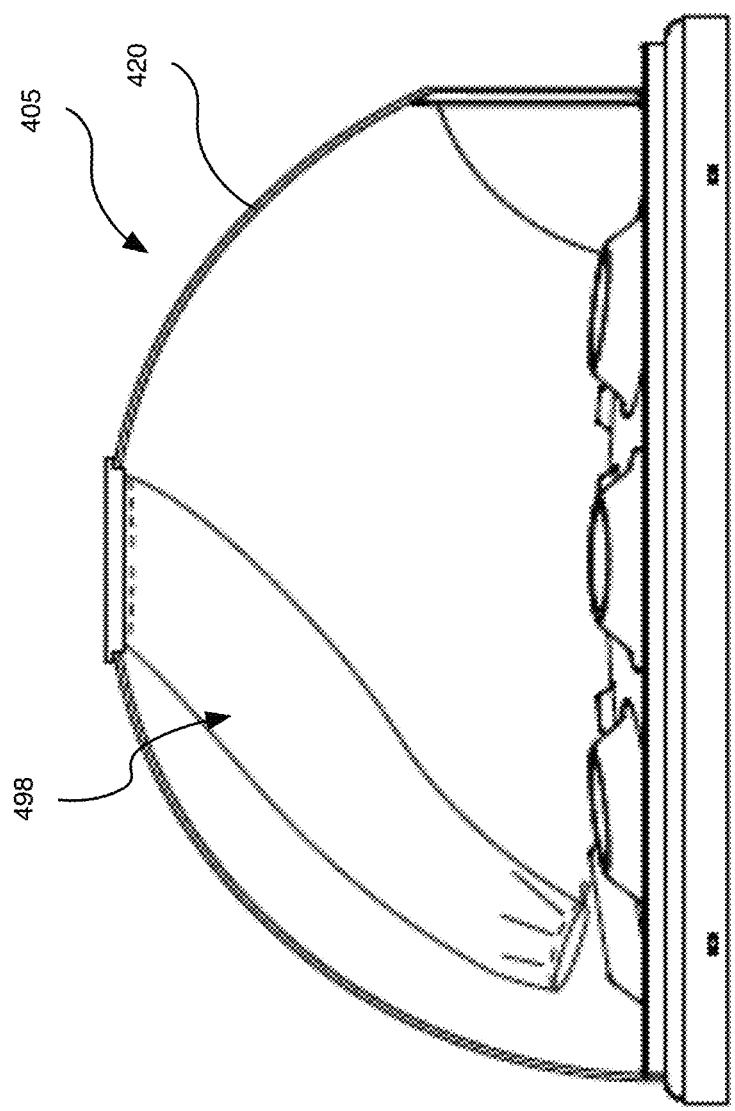
FIG. 16B depicts a side, cross-section view of the mating and oviposition chamber including the cleaning sleeve of FIG. 16A.
Figure 16C:
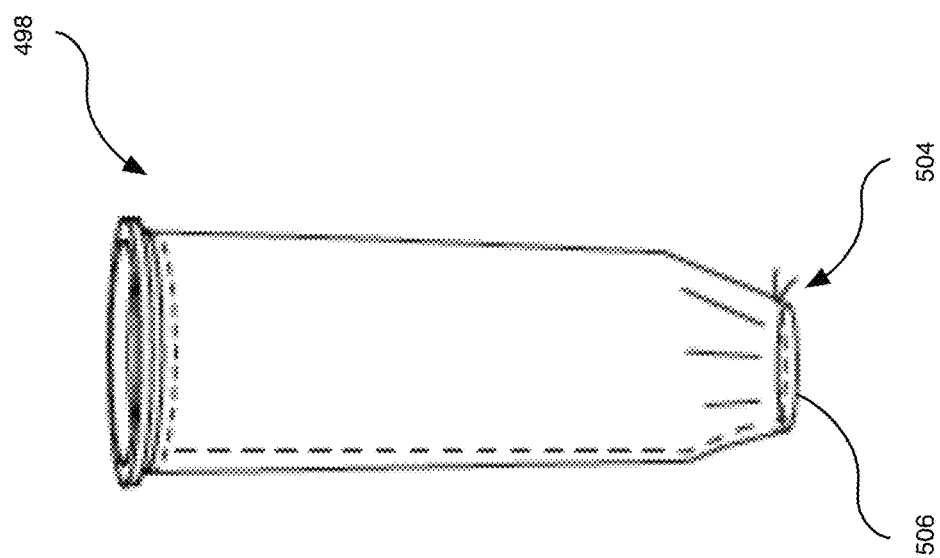
FIG. 16C depicts the cleaning sleeve shown in FIGS. 16A and 16B in isolation.

The system 100 also includes a harvesting receptacle 202 (FIG. 5) for harvesting the larvae. In the system 100, the harvesting receptacle 202 is a drawer or container that is nested or integral with the larvae-chamber 175. In some embodiments, the harvesting receptacle is a separate container that is exterior to the larvae-chamber 175 and the chamber structure 120. The harvesting receptacle 202 is in communication with the larvae-growth chamber 175 in that mature larvae are able to travel from the larvae-growth chamber 175 to the harvesting receptacle 202. In particular, the system 100 includes at least one inclined surface configured to provide at least a partial passageway for the larvae to travel from the larvae-growth chamber 175 to the harvesting receptacle 202. For example, the system 100 includes a migration ramp 207 (FIGS. 1A, 7) having an inclined surface 213 (FIG. 8) that connects the larvae-growth chamber 175 to the harvesting receptacle 202. When the larvae mature (e.g., into prepupae), they usually enter a wandering stage in which they seek drier and darker locations than the feeding site to continue to the next stage of the lifecycle, pupation. Depending on the humidity within the larvae-growth chamber 175, the larvae will be able to climb inclined surfaces of various degrees to a horizontal datum, H (FIG. 14). Generally, the greater the humidity within the larvae-growth chamber 175, the steeper the angle of incline, R, the larvae will be able to climb up. For example, if the feed medium is dry, the larvae may find it difficult to climb up a surface having an incline greater than 45 degrees. If the feed medium is moist and the interior conditions of the larvae-growth chamber 175 are humid, the larvae may be able to climb up an angle of incline that is almost 90 degrees. The inclined surface 213 provides at least a partial passageway for the larvae to crawl out of the moist environment of the larvae-growth chamber 175 to the comparatively drier environment of the harvesting receptacle 202. As a result of this migration to the harvesting receptacle 202, for at least some of the mature larvae, the need to physically remove the mature larvae from the larvae-growth chamber 175 in order to harvest the mature larvae is reduced. Furthermore, providing a desirable passageway for the larvae to exit the larvae-growth chamber 175 may help reduce instances of the larvae pupating within the larvae-growth chamber 175.

It is understood that the harvesting receptacle 202 does not need to be a container specifically configured for harvesting the larvae from the larvae-chamber 175, but can be any container or component that is capable of receiving the larvae from the larvae-growth chamber 175. As a result, the harvesting receptacle 202 may be provided separately from other components of the system 100.

Figure 8:
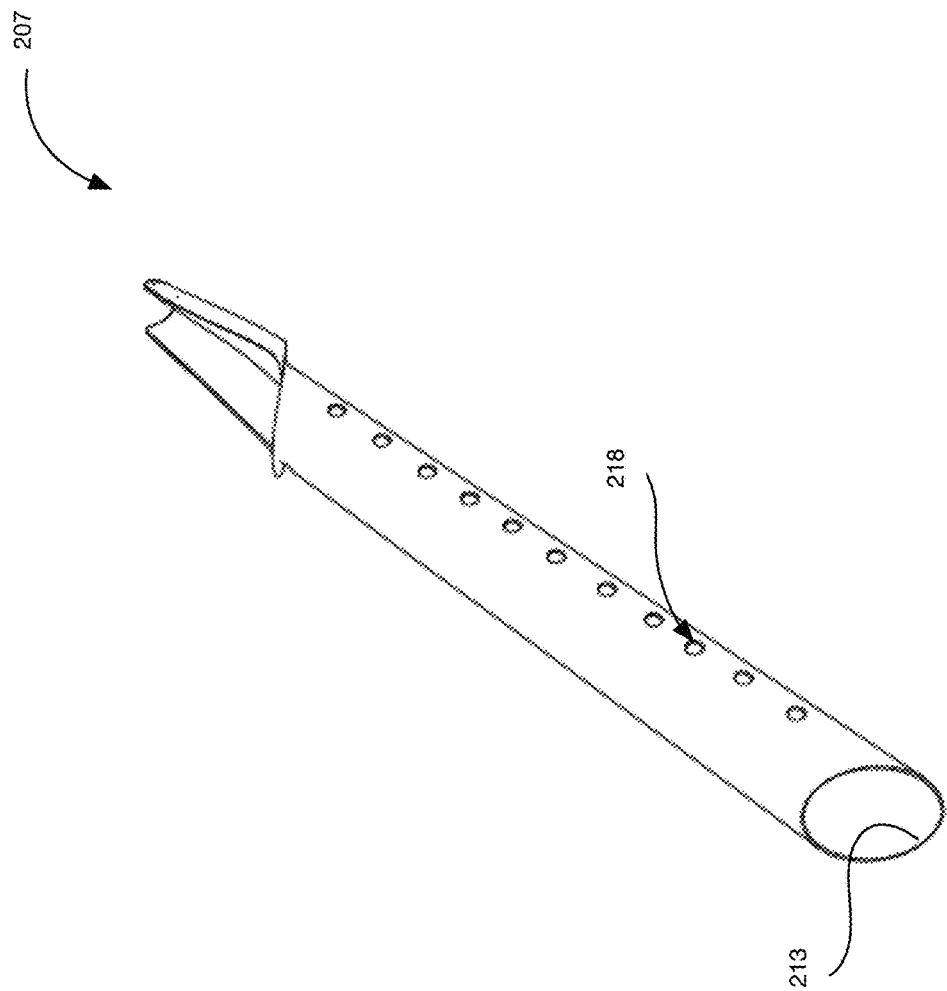
FIG. 8 depicts a perspective view of a migration ramp, according to non-limiting embodiments.

In some embodiments, the inclined surface 213 is inclined at an angle, R, generally between 25 and 90 degrees from a horizontal datum (shown as H in FIG. 1A). In some embodiments, the angle R is between 25 and 45 degrees. The migration ramp 207 may be curved. The migration ramp 207 may have a surface treatment applied to the inclined surface 213 to help the larvae climb up the migration ramp 207. The migration ramp 207 may be an open shape or a closed shape. For example, the migration ramp 207 could be a tube that is closed at both ends having suitably sized apertures about the circumference of the tube to allow the larvae to climb into the migration ramp 207 and travel to the harvesting receptacle 202. As another example, the migration ramp 207 could be configured as shown in FIG. 8 as an open tubular structure with access apertures 218 to allow the larvae multiple points of access into the migration ramp 213. In some embodiments, the migration ramp 207 is formed from more than one section, such a tube divided into two halves. In some embodiments, the system 100 includes more than migration ramp 207.

It is understood that the inclined surface 213 does not have to provide a complete or direct path or passageway to the harvesting receptacle 202. For example, the larvae may travel over the inclined surface 213 in combination with other surfaces that are not inclined to reach the harvesting receptacle 202. As a result, the inclined surface 213 would provide at least a partial passageway for the larvae to travel from the larvae-growth chamber to the harvesting receptacle.

After climbing up the migration ramp 207, the mature larvae can fall through a harvest opening 228 into the harvesting receptacle 202 where a user of the system 100 may harvest the mature larvae (FIG. 3). In some embodiments, the harvesting receptacle 202 is insulated to pre-cool the mature larvae. The insects will usually be consumed as larvae or prepupae. In some embodiments, the harvesting receptacle 202 may have a temperature control system, such as a cooling system (not shown), that operates to maintain the interior environment of the harvesting receptacle 202 at a desired temperature to prevent the larvae from pupating into adult insects and/or kill the larvae (e.g., by freezing the larvae). In some embodiments, the cooling system is activated intermittently. The user may not want to freeze or cool the larvae, but would like to use the harvested larvae to restart the insect lifecycle. In some embodiments, the cooling system is not active all the time, but activated only at times and for durations sufficient to kill the larvae in the harvesting receptacle 202 or to put the larvae into a dormant state.

The system 100 may include a device or devices to manage the interior environment of one or more of the egg-producing chamber structure 105, the larvae-growth chamber 175 and the harvesting receptacle 202. For example, the system 100 can include a ventilation unit 233 that regulates micro-climate conditions of one or more of the egg-producing chamber structure 105, the larvae-growth chamber 175 and the harvesting receptacle 202. The ventilation unit 233 may regulate one or more temperature and humidity, and may be adjusted through regulators installed interior of the system 100.

A protective cap 223 (FIG. 3) prevents mature larvae from escaping. In some embodiments, the protective cap 223 is transparent and provides a way for a user of the system 100 to observe at least part of the lifecycle of the insects.

The emerged adult insects will likely die in the mating and oviposition chamber 120. The system 100 can include a dead insect trap 238 which dead insects can fall into and through to a waste receptacle 243. At least one interior wall 248 of the mating and oviposition chamber 120 can be shaped to aid in guiding dead insects to the dead insect trap 238. For example, the interior wall 248 (FIG. 1A) is curved towards the dead insect trap 238. The dead insect trap 238 can be any suitable shape. For example, the inlet of the dead insect trap 238 has a circular shape. However, the inlet of the dead insect trap 238 can have a slot, square or other suitable shape. In some embodiments, system 100 includes a vacuum device (not shown) operatively connected to the dead insect trap 238 to draw dead insects into the dead insect trap 238 and into the waste receptacle 243.

The waste receptacle 243 is also configured to receive feces from the larvae in the larvae-growth chamber 175 as well as the dead insects. For example, the waste receptacle 243 can be in communication with both the larvae-growth chamber 175 via a set of apertures in the larvae-growth chamber (not shown) and the dead insect trap 238. The larvae feces, diluted with water, may be used as a fertilizer for plants.

Figure 9:
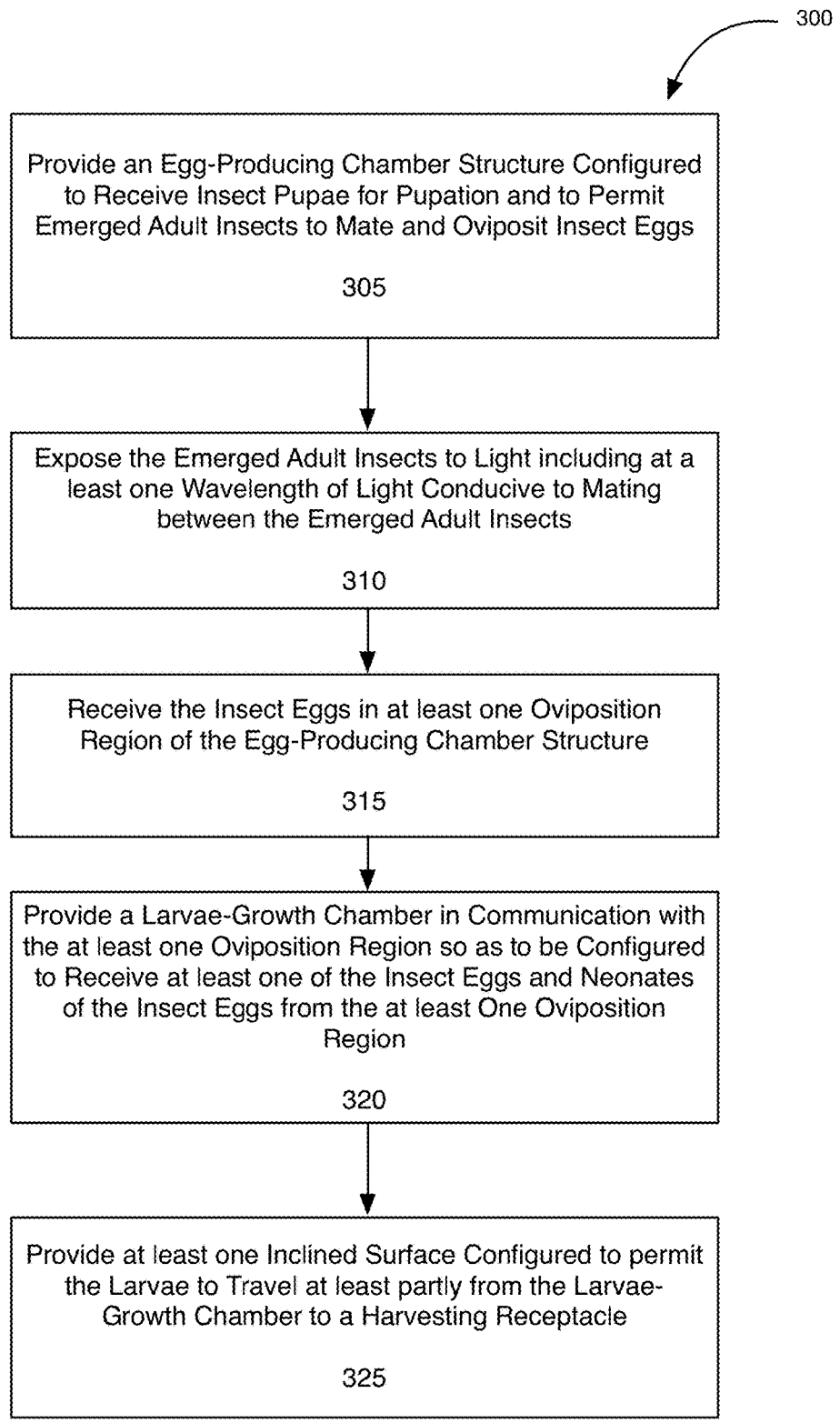
FIG. 9 depicts a flowchart of a method for breeding and harvesting insects, according to non-limiting embodiments.

FIG. 9 depicts a flowchart of an example method 300 for breeding and harvesting insects. In order to assist with in the explanation of the method 300, it will be assumed that the method 300 is performed using the system 100. However, it is to be understood that the system 100 and/or the method 300 can be varied, and need not work exactly as discussed herein in conjunction with each other, and that such variations are within the scope of the described systems and methods. It is also understood that the method 300 need not be performed in the exact sequence as shown unless otherwise indicated; and likewise various blocks may be performed in parallel rather than in sequence; hence the elements of the method 300 are referred to as "blocks" rather than "steps". It is also understood that the method 300 can be implemented on variations of the system 100 as well.

At block 305, an egg-producing chamber structure, such as the egg-producing chamber structure 105, that is configured to receive insect pupae for pupation and to permit the emerged adult insects to mate and oviposit insect eggs is provided. As in the egg-producing chamber structure 105, the provided egg-producing chamber structure can include one or more chambers. In some embodiments, multiple insect lifecycle stages are at least started in the same chamber. In some embodiments, one or more of insect lifecycle stages are performed in separate chambers. Hydration structures configured to provide a hydrating fluid to the emerged adult insects could also be provided in the chamber structure, such as the hydration nozzles 165 of the egg-producing chamber structure 105.

At block 310, the emerged adult insects are exposed to light including at least one wavelength of light that is conducive to mating between the emerged adult insects, such as light including the wavelength of light 258. In some embodiments, exposing the emerged adult insects to light including the at least one wavelength of light conducive to mating includes exposing the emerged adult insects to ambient light (e.g., to light that is ambient to the egg-producing chamber structure). In some other embodiments, exposing the emerged adult insects to light including the at least one wavelength of light conducive to mating includes exposing the emerged adult insects to artificial light. For example, a lamp configured to provide light including the wavelength of light 258 may be used to perform block 310.

At block 315, the insect eggs and/or the neonates of the insect eggs are received in at least one oviposition region of the chamber structure, such as the oviposition region 125 of the chamber structure 105.

At block 320, a larvae-growth chamber, such as the larvae-growth chamber 175, that is in communication with the at least one oviposition region so as to be configured to receive at least one of the insect eggs and neonates of the insect eggs from the at least one oviposition region, such as the oviposition region 125, is provided. The provided larvae-growth chamber is configured to permit the insect eggs (and neonates of the insect eggs) to transition into larvae and to hold feed material for the larvae. For example, as described above, the larvae-growth chamber 175 may be round in shape in order for the larvae to grow efficiently and the walls of the larvae-growth chamber 175, such as walls 190, can be opaque, semi-opaque or partly opaque. The larvae-growth chamber 175 may also include the feeding door 195 that can be opened to deposit the feed material into the larvae-growth chamber 175.

At block 325, at least one inclined surface, such as the inclined surface 213 of the migration ramp 207, is provided to permit the larvae to travel at least partly from the larvae-growth chamber to a harvesting receptacle, such as the harvesting receptacle 202.

FIGS. 10 to 16, which show another embodiment of a system for breeding and harvesting insects, an example system 400. The example system 400 is at least partially enclosed and can be used to breed and harvest black soldier flies and their larvae. In some embodiments, the system 400 is used for breeding and harvesting other insect species. The system 400 shares some features with system 100 and like features have like numbers beginning with a "4" rather than a "1" or a "2". Although the system 400 shares some features with the system 100, the system 400 does include at least one alternative or additional feature. These differences will be discussed further below.

Figure 11:
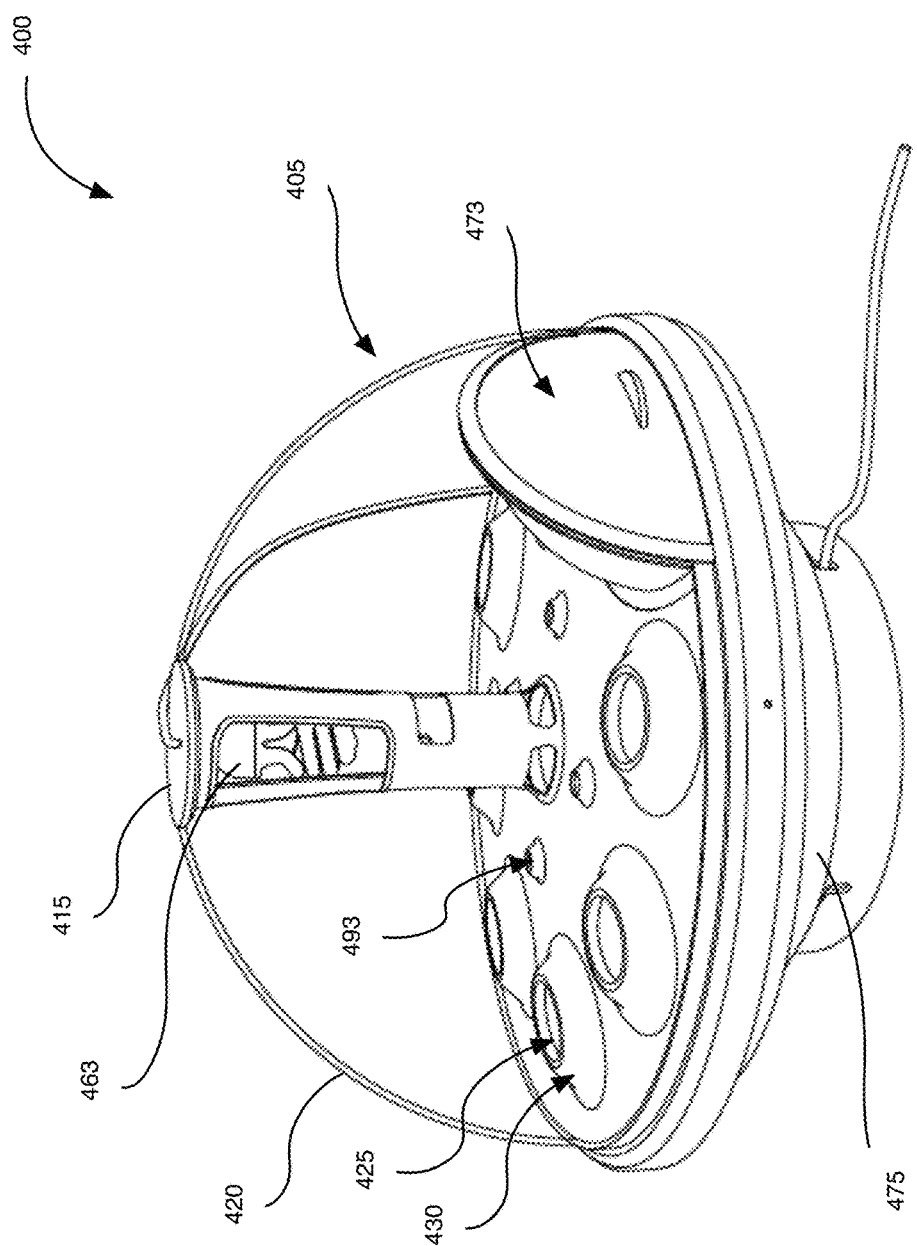
FIG. 11 depicts a perspective view of the system for breeding and harvesting insects in FIG. 10, with a partial cutaway of the chamber structure, according to a second set of non-limiting embodiments.

The system 400 includes an egg-producing chamber structure 405 configured to receive insect pupae for pupation and to permit emerged adult insects to mate and oviposit eggs. The egg-producing chamber structure 405 may be any suitable shape and size. The egg-producing chamber structure 405 can include one or more chambers. Similarly to the system 100, the egg-producing chamber structure 405 can include more than one chamber structure, such as a pupation chamber 415 and a mating and oviposition chamber 420 (FIG. 11). In some embodiments, multiple insect lifecycle stages are at least started in the same chamber. In some embodiments, one or more insect lifecycle stages are performed in separate chambers. Particular features of the pupation chamber 415 and the mating and oviposition chamber 420 are described further below.

The egg-producing chamber structure 405 includes at least one egg-laying or oviposition region 425 (FIG. 12A) that is configured to receive the insect eggs and to allow at least one of the insect eggs and neonates of the insect eggs to pass therethrough. For example, in some embodiments, the at least one oviposition region 425 is included in at least one nozzle structure 430 (FIG. 12B) in the egg-producing chamber structure 405. However, any suitable location for the oviposition region 425 in the egg-producing chamber structure 420 is contemplated.

Figure 12A:
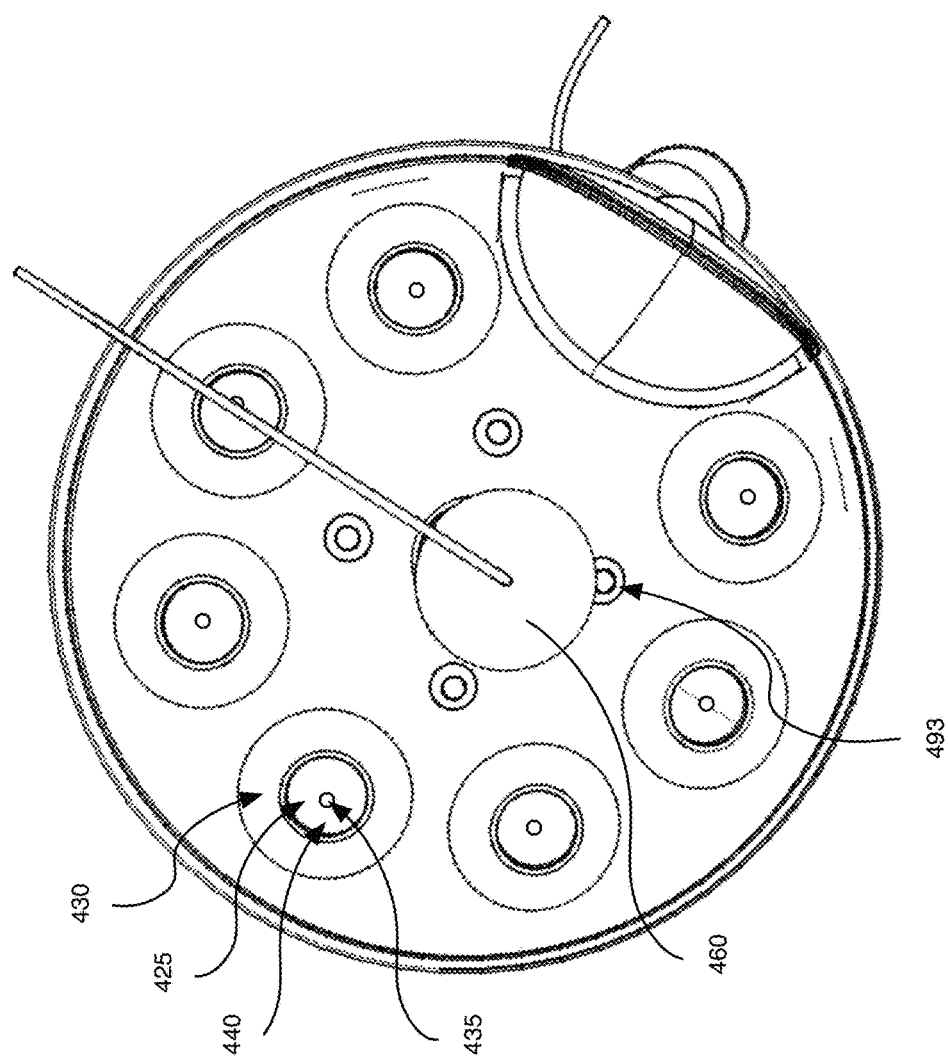
FIG. 12A depicts a top plan view of the system for breeding and harvesting insects in FIG. 10, with a portion of the mating and oviposition chamber removed, according to a second set of non-limiting embodiments.

The oviposition region 425 can take any suitable configuration that allows at least one of the insect eggs and the neonates of the insect eggs to pass through. For example, the oviposition region 425 can include at least one egg-receiving aperture 435 (FIG. 12) sized to allow at least one of the insect eggs and the neonates of the insect eggs to pass through. The oviposition region 425 can include at least one of a mesh structure and a perforated solid structure. For example, the oviposition region 425 can be formed as a perforated solid structure, shown in FIG. 12A as a membrane 440 interior of the nozzle structure 430. FIGS. 12B to 12D depict an example mesh structure 441 (FIG. 12C) in an oviposition cup 442 interior of the nozzle structure 430 (FIGS. 12C, 12D). The mesh structure 441 can be formed from a 2 millimeters diameter aluminum mesh. In some embodiments, the depth, T, of the mesh structure 441 from a top surface 447 of the oviposition cup 442 can be 10 millimeters. In some embodiments, the depth, T, is 50 millimeters. In some embodiments, the oviposition region 425 can include a combination of perforated solid structures and mesh structures. In some embodiments, the oviposition region 425 includes at least one pair of oviposition plates 436 (FIG. 12E) in which the at least one egg-receiving aperture is at least one oviposition slot 437 formed between the pair of oviposition plates 436. The pair of oviposition plates 436 are connected to each other in spaced-apart relation by spacers 439. In some embodiments, the distance, M, between the pair of oviposition plates 436 is approximately 2 mm.

In some embodiments, the oviposition region 425 is removable from the egg-producing chamber structure 405 to, for example, clean or replace the oviposition region 425.

As in the system 100, the egg-receiving apertures 435 can have a variety of suitable sizes and shapes. For example, in some embodiments, the egg-receiving apertures 435 are circular in shape and have diameters ranging from approximately two millimeters to four millimeters. In some embodiments, the egg-receiving apertures 435 are elliptical, squared, organic, free-formed in shape or any combination thereof. The nozzle structures 430 can be arranged in any suitable manner in the mating and oviposition chamber 420.

FIGS. 13A to 13D show an example pupation chamber 415. Similarly to the pupation chamber 115B, the pupation chamber 415 can include at least one aperture configured to allow the emerged adult insects to exit the pupation chamber 415, such as the exit holes 455. The exit holes 455 are also positioned at a distance, D, away from the bottom surface, B, a compartment of the pupation chamber 415 that is configured to hold or retain the pupae and prepupae and help prevent the pupae and prepupae from escaping from the pupation chamber 415, while permitting the emerged adult insects to leave the pupation chamber 415 (e.g., by flying out of the pupation chamber 415). The distance, D, can be determined based on a desired number of pupae and/or prepupae the pupation chamber 415 is to hold. In order to perform maintenance and/or to deposit the prepupae and/or pupae into the pupation chamber 415, the pupation chamber 415 may be removably attached to the remainder of the egg-producing chamber structure 405 (e.g., to the mating and oviposition chamber 420). The pupation chamber 415 may have a cover or top, such as cover 460. The cover 460 can be a mesh structure, a plastic structure or any other suitable covering for the pupation chamber 415.

Figure 13B:
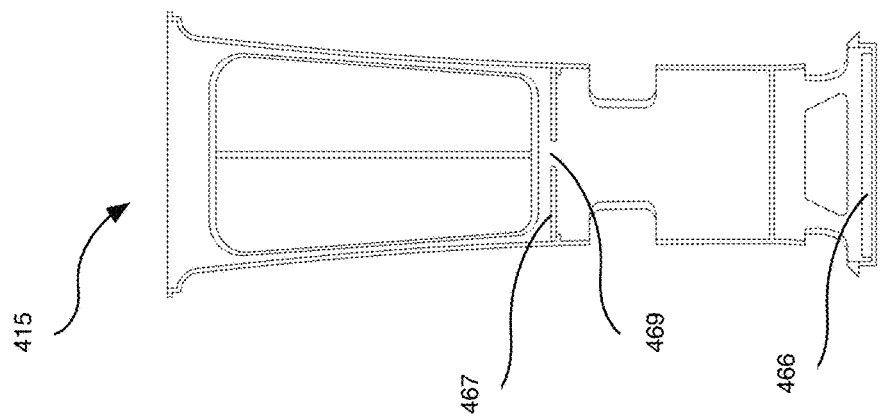
FIG. 13B depicts a cross-section view of the pupation chamber shown in FIG. 13A, according to a second set of non-limiting embodiments.
Figure 13A:
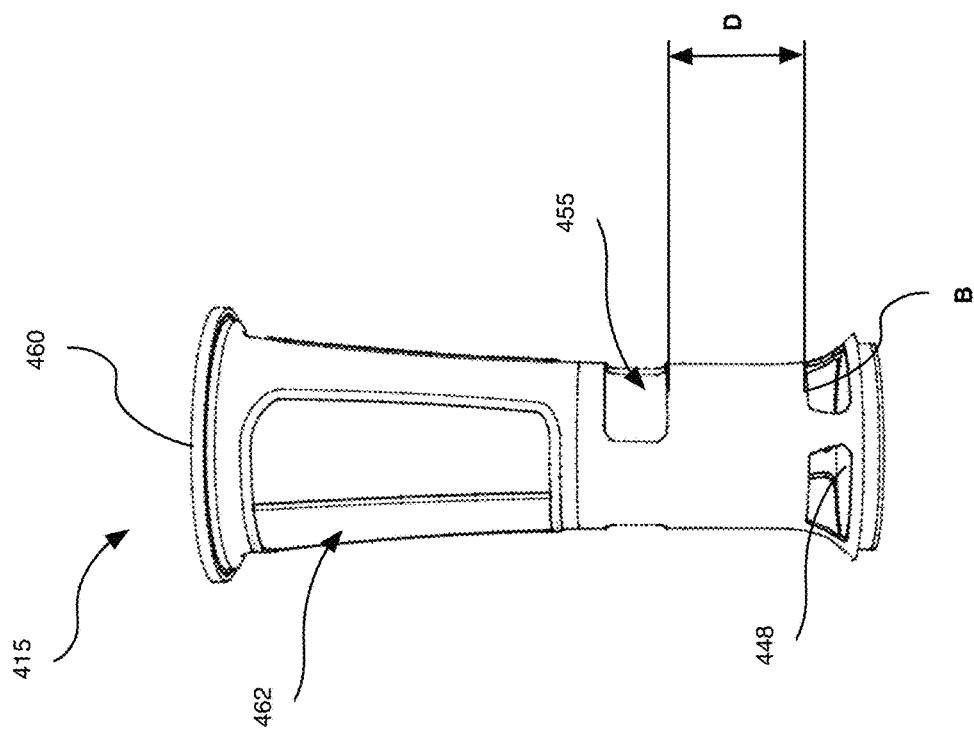
FIG. 13A depicts a perspective view of a pupation chamber, according to a second set of non-limiting embodiments.
Figure 13C:
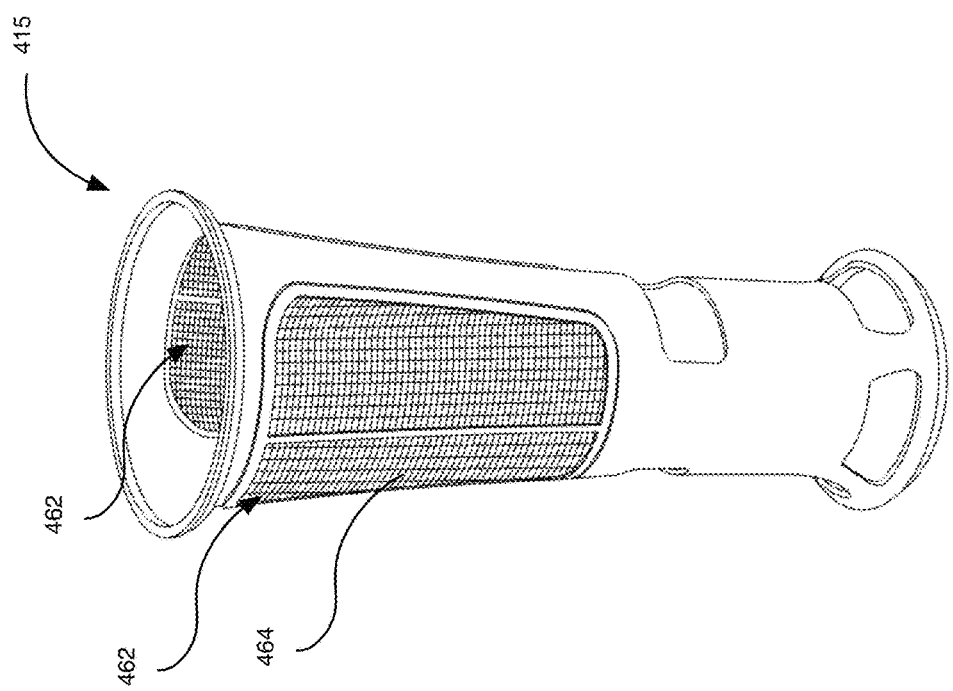
FIG. 13C depicts a perspective view of a pupation chamber, according to a second set of non-limiting embodiments.
Figure 13D:
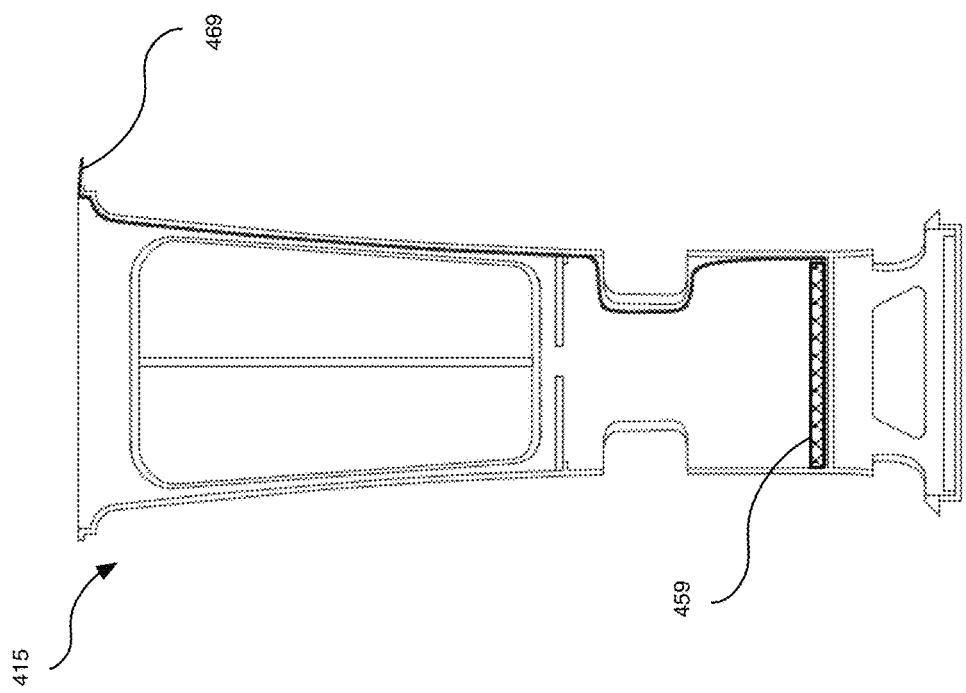
FIG. 13D depicts a cross-section of the pupation chamber shown in FIG. 13A including a pupation heat mat, according to non-limiting embodiments.

In some embodiments, it might be desirable to expose the pupae and pre-pupae in the pupation chamber to heat. As shown in FIG. 13D, the pupation chamber 415 can include a pupation heat mat 459 interior of the pupation chamber 415. A cable 469 to provide electrical power to the heat mat 459 may be run, for example, upwards towards the cover 460 (not shown in FIG. 13D) or downwards underneath the mating and oviposition chamber 420.

The egg-producing chamber structure 405 can include a compartment configured to hold a hydrating fluid for the emerged adult insects. For example, the pupation chamber 415 can include a nutrient compartment 448 configured to hold a hydrating fluid and/or a pad 466 (FIG. 13B) or cloth impregnated with the hydrating fluid. The pad 466 may be made from food grade cotton or synthetic materials. The pad 466 may be disposable.

The pupation chamber 415 may be any suitable shape and manufactured from any suitable material or combination of materials. As soon as the prepupae and/or the pupae emerge as adult insects, they seek their way out of the pupation chamber 415, into the mating and oviposition chamber 420.

The adult emerged insects, such as black soldier flies, will likely spend their adult lifecycle (fly stadium) in the mating and oviposition chamber 420. The mating and oviposition chamber 420 is in communication with the pupation chamber 415 such that the emerged adult insects can exit the pupation chamber 415 and reach the mating and oviposition chamber 420. In the example system 400, the emerged adult insects are able to exit the pupation chamber 415, through the exit holes 455, for example, directly into the mating and oviposition chamber 420. However, in some embodiments, there is at least one intermediary structure between the pupation chamber 415 and the mating and oviposition chamber 420 configured for the emerged adult insects to travel through to reach the mating and oviposition chamber 420.

Figure 10:
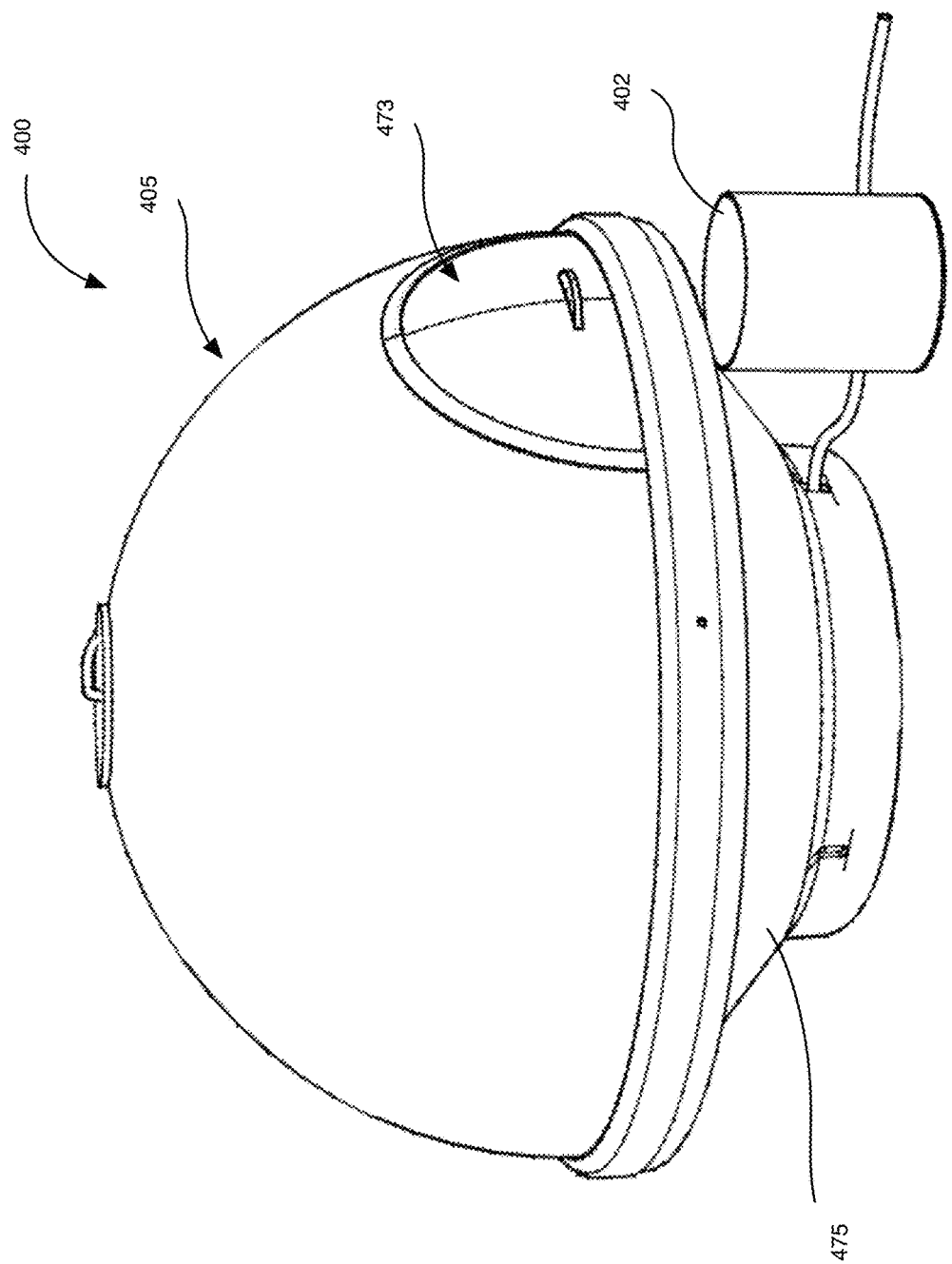
FIG. 10 depicts a perspective view of a system for breeding and harvesting insects, according to a second set of non-limiting embodiments.

The mating and oviposition chamber 420 can take a variety of shapes and can be formed from a variety of materials. As shown in FIGS. 10 and 11, the mating and oviposition chamber 420 can be generally hemispheric in shape, which may make the interior space of the mating and oviposition chamber 420 appear larger for the adult insects, such as flies. For easier access to the interior of the mating and oviposition chamber 420 (e.g., for cleaning or other maintenance), the mating and oviposition chamber 420 may be separable into two or more sections and/or removably attached to the remainder of the egg-producing chamber structure 405 and/or the system 400. The mating and oviposition chamber 420 may be manufactured from any suitable material, such as glass, plastic or plexiglass. The mating and oviposition chamber 420 may be fully or partially transparent, or fully opaque. In some embodiments, a coating or film (such as an ultraviolet filter film) may be applied to at least one portion of the mating and oviposition chamber 420. The mating and oviposition chamber 420 may be manufactured from a solid material, which may help contain odours from the larvae colony in the larvae-growth chamber 475 (described below) within the system 400. In some embodiments, seals are provided between one or more of the pupation chamber 415, the mating and oviposition chamber 120 and the larvae-growth chamber 475 to help contain odours from the larvae colony.

Similarly to the system 100, in order to aid in mating between the emerged adult insects, in some embodiments, the system 400 includes a light source 453 (FIG. 14) configured to expose the emerged adult insects to light including at least one wavelength of light 458 conducive to mating between the emerged adult insects. In some embodiments, the light source 453 is ambient to the egg-producing chamber structure 405 and at least the mating and oviposition chamber 420 is configured to transmit light of the at least one wavelength of light 458 into the mating and oviposition chamber 420. For example, as in the system 100, the light source 453 can be the Sun that transmits light including the wavelength of light 458, such as the full spectrum of sunlight, and the mating and oviposition chamber 420 can be manufactured from a material that permits the light including the at least the wavelength of light 458 from the Sun, S, to be transmitted into the mating and oviposition chamber 420, such as glass, an ultra-violet light transmissive plexiglass or a netting material. The mating and oviposition chamber 420 may also include one or more apertures to permit light including the at least the wavelength of light 458 from the Sun, S, to be transmitted into the mating and oviposition chamber 420. In some embodiments, the light source 453 is an artificial light source, such as a lamp 463, configured to provide artificial light including the wavelength of light 458. The lamp 463 can include a bulb configured to provide ultraviolet light, such as a light bulb that provides light of a wavelength in the ultraviolet B spectrum. For example, a light bulb typically used to provide ideal conditions for reptiles without an undesirable amount of heat can be used (e.g., ExoTerra™ E27, 230 Volt, 25 Watt bulb). As stated above, in some embodiments, it might be desirable to expose the pupae and pre-pupae in the pupation chamber to heat. In some embodiments, the light source 453 can be used to provide at least some heat in the pupation chamber 415, by for example, selecting a light bulb that emits at least some heat. In some embodiments, the artificial light source is located interior of the chamber structure 405. For example, the artificial light source 453 can be located interior of the pupation chamber 415 (as shown in FIGS. 11 and 14). The pupation chamber 415 can be configured to house the light source 453 and to allow light including the wavelength of light 458 to be transmitted into the mating and oviposition chamber 420 (FIGS. 11 and 14). For example, the pupation chamber 415 can include one or more openings 462 (FIG. 13A) for light including the wavelength of light 458 to be transmitted through. The openings 462 can have a light transmissible covering, such a mesh screen 464 (FIG. 13C) or glass. The pupation chamber 415 can include a shield 467 (FIG. 13B) configured to prevent the pupae from being exposed to an undesirable amount of light (e.g., an amount of light that would inhibit transformation into adult insects or that would be harmful to the pupae). The shield 467 can be removable from the pupation chamber 415. For example, the shield 467 can include a finger hole 469 to grasp the shield for placement into or removal from the pupation chamber 415. The shield 467 may also include a grasping member (not shown), such as a knob, to grasp the shield for placement into or removal from the pupation chamber 415. In some embodiments, the light source 453 is held in place in the pupation chamber 415 by the cover 460.

As it will be apparent, the pupation chamber 415 can be configured to perform multiple functions. In some embodiments, the pupation chamber 415 can provide a location for the source of hydrating fluid for the adult emerged insects, a site for pupation and a housing for the light source 453. Configuring the pupation chamber 415 to perform multiple functions can result in a more efficient use of the interior space of the mating and oviposition chamber 420, giving the adult emerged insects more space to travel about the interior of the mating and oviposition chamber 420 and to mate.

Similarly to the system 100, the insect eggs and/or neonates of the insect eggs pass through the oviposition region 425 into a larvae-growth chamber 475 (FIG. 14). The larvae-growth chamber 475 is in communication with the oviposition region 425 so as to be configured to receive the insect eggs and/or the neonates of the insect eggs from the oviposition region 425. For example, the insect eggs and/or neonates of the insect eggs may pass through the egg-receiving apertures 435 (FIG. 12A) into the larvae-growth chamber 475 by gravity (i.e., fall through the egg-receiving apertures 435 into the larvae-growth chamber 475) or push themselves through the egg-receiving apertures 435 to get to the larvae-growth chamber 475, enticed by the smell of the feed material in the larvae-growth chamber 175. Similarly to the system 100, airflow through the egg-receiving apertures 435 of the oviposition region 425 from the larvae-growth chamber 475 into the mating and oviposition chamber 420 may be sufficient to stimulate oviposition. Hence, in some embodiments, the oviposition region 425 performs multiple functions, including providing a site for oviposition, providing a mechanism to transport the insect eggs and/or neonates of the insect eggs to the larvae-growth chamber 475 without direct human intervention, and to permit airflow from the larvae-growth chamber 475 to the egg-producing chamber structure 405 (e.g., to the mating and oviposition chamber 420) to help stimulate oviposition.

The larvae-growth chamber 475 is configured to permit the insect eggs and/or the neonates of the insect eggs to transition into larvae. For example, the larvae-growth chamber 475 may be round in shape in order for the larvae to grow efficiently. The larvae can be sensitive to light and prefer darkness. As a result, in some embodiments, the walls of the larvae-growth chamber 475, such as walls 468 (FIG. 14), can be opaque, semi-opaque or partly opaque. Surface treatments or films may be applied to the walls 468 to achieve the desired light transmissibility.

Similarly to the system 100, the larvae-growth chamber 475 is configured to hold feed material for the larvae. For example, in the system 400, the larvae can be fed organic waste material, such as food scraps, through a feed hatch 473 (FIG. 14), which is connected to the larvae-growth chamber 475. The feed material may also be pre-processed feed or germ plasma. As another example, the larvae-growth chamber 475 may be separable from the chamber structure 420 to allow feed material to be directly deposited into the larvae-growth chamber 475.

Figure 18:
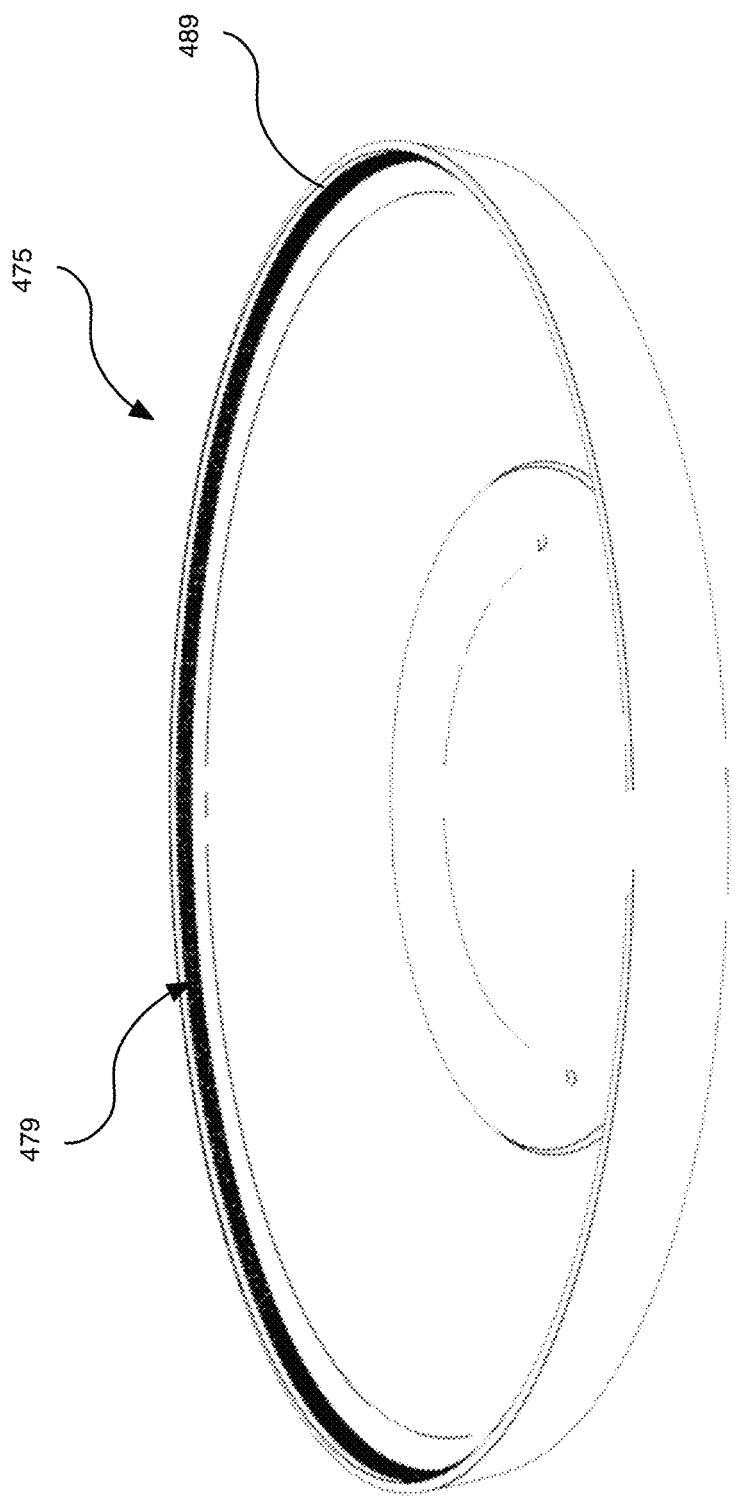
FIG. 18 depicts a larvae-growth chamber including a hooked substrate, according to non-limiting embodiments.
Figure 19:
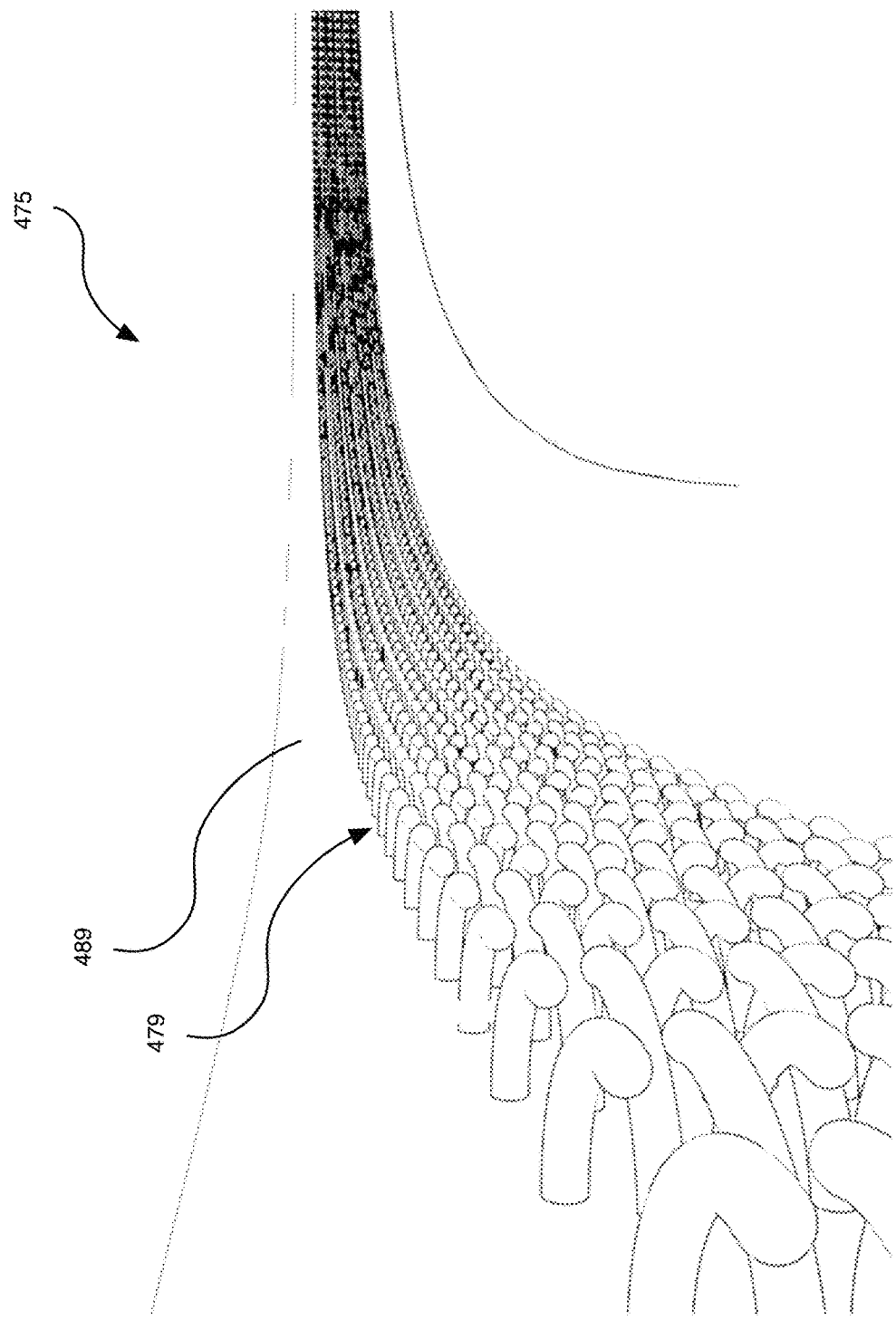
FIG. 19 depicts an enlarged view of the hooked substrate shown in FIG. 18.

The larvae-growth chamber 475 can have additional structures to prevent larvae escape through the feed hatch 473 or elsewhere from the larvae-growth chamber 475. These additional structures can include small three-dimensional structures, such as a hooked substrate 479 (from a hook-and-loop substrate) (FIGS. 18, 19) that provides a barrier for crawling larvae. The "hooked" surface of the hooked substrate 479 provides small surfaces that are difficult for larvae to crawl over. As shown in FIGS. 18 and 19, the hooked substrate 479 can be connected to an interior peripheral surface 489 of the larvae-growth chamber 475. The hooked substrate 479 can be separately formed and then connected to the interior peripheral surface 489. The hooked substrate 479 can be moulded onto to be integral with the interior peripheral surface 489. The hooked substrate 479 can cover only a portion or discrete portions of an interior surface of the larvae-growth chamber 475, such as the interior peripheral surface 489.

The system 400 also includes a harvesting receptacle 402 (FIG. 10). In the system 400, the harvesting receptacle 402 is a separate container that is exterior to the larvae-chamber 475 and the chamber structure 420. However, in some embodiments, the harvesting receptacle 402 is a structure that is nested or integral with the larvae-chamber 475. In some embodiments, the harvesting receptacle 402 is insulated to pre-cool the mature larvae. The insects will usually be consumed as larvae or prepupae. In some embodiments, the harvesting receptacle 402 may have a temperature control system, such as a cooling system (not shown), that operates to maintain the interior environment of the harvesting receptacle 402 at a desired temperature to prevent the larvae from pupating into adult insects and/or kill the larvae (e.g., by freezing the larvae). In some embodiments, the cooling system is activated intermittently. In some cases, the user may not want to freeze or cool the larvae, but would like to use the harvested larvae to restart the insect lifecycle. In some embodiments, the cooling system is not active all the time, but activated only at times and for durations sufficient to kill the larvae in the harvesting receptacle 402 or to put the larvae into a dormant state.

The harvesting receptacle 402 is in communication with the larvae-growth chamber 475 in that mature larvae are able to travel from the larvae-growth chamber 475 to the harvesting receptacle 402. In contrast to the system 100, the larvae-growth chamber 475 of the system 400 includes at least one inclined wall portion, such as peripheral wall 468, that is configured to provide at least a partial passageway for the larvae to travel from the larvae-growth chamber 475 to the harvesting receptacle 402. The mature larvae can climb up the inclined wall portion to at least one larvae exit aperture, such as a larvae exit aperture 478 (FIGS. 14, 15), sized to allow the mature larvae to pass through the harvesting receptacle 402 positioned below the larvae exit aperture 478. The system 400 avoids having to manufacture a separate component to accomplish this function, reducing manufacturing and assembly complexity. In some embodiments, the inclined wall portion is the entire peripheral wall or set of peripheral walls, such as the peripheral wall 468, and the inclined peripheral wall provides the at least partial passageway about the entire periphery of the larvae-growth chamber 475. As a result, the larvae would be able to travel to the harvesting receptacle 402 about 360 degrees of the peripheral wall rather than be required to find discrete portions of the peripheral wall 468, for example, to travel to the larvae exit aperture 478 and, eventually, to the harvesting receptacle 402.

Although the at least one inclined wall portion is shown as the entire peripheral wall of the larvae-growth chamber 475, peripheral wall 468, in some embodiments the entire peripheral wall is not inclined and can instead be one or more distinct sections of the wall 468 that are inclined while the remainder of the wall 468 is not inclined (i.e., either 90 degrees from a horizontal datum or zero degrees from a horizontal datum). Furthermore, the larvae-growth chamber 475 can include more than one larvae exit aperture 478.

In some embodiments, the at least one inclined wall portion is inclined at an angle, R, generally between 25 and 90 degrees from a horizontal datum (shown as H in FIG. 14). In some embodiments, the angle R is between 25 and 45 degrees.

Similarly to the inclined surface 213, the inclined wall portion of the larvae-growth chamber 475 does not have to provide a complete or direct path or passageway to the harvesting receptacle 402. For example, the larvae may travel over the inclined wall portion in combination with other surfaces or components that are not inclined to reach the harvesting receptacle 402. As a result, the inclined wall portion would provide at least a partial passageway for the larvae to travel from the larvae-growth chamber to the harvesting receptacle 402.

It is understood that the harvesting receptacle 402 does not need to be a container specifically configured for harvesting the larvae from the larvae-growth chamber 475, but can be any container or component that is capable of receiving the larvae from the larvae-growth chamber 475. For example, a user may place one or both hands underneath the larvae exit aperture 478 to catch the larvae as they exit the larvae-growth chamber 475. As a result, the harvesting receptacle 402 may be provided separately from other components of the system 400.

The user may want to delay harvesting the larvae from the larvae-growth chamber 475. In some embodiments, the larvae-growth chamber includes a larvae exit plug 451 (FIG. 14) that is sized to engage the larvae exit aperture 478 and to prevent the larvae from exiting the larvae-growth chamber 475 via the larvae exit aperture 478.

The system 400 may include a device or devices configured to manage the interior environment of one or more of the egg-producing chamber structure 405, the larvae-growth chamber 475 and the harvesting receptacle 402. For example, the system 400 can include a heating mat 483 (FIG. 14) that heats the surrounding air to provide an air temperature that is conducive to larvae growth. For example, in some embodiments, the heating mat 483 provides an air temperature generally between 27 and 30 degrees Celsius. As the heated air moves between the larvae-growth chamber 475 and the egg-producing chamber structure 405, the temperature of the heated air in the mating and oviposition chamber 420 may reach a temperature that is conducive to mating between the adult emerged insects, such as generally between 25 to 29 degrees Celsius. The heating mat 483 can be waterproof or otherwise impermeable to fluids. The device or devices included to manage the interior conditions are not limited to a heating mat. For example, a ventilation unit and/or a humidifier can also be included.

Waste material, such as larvae feces and other fluids, can travel from the larvae-growth chamber 475 to a waste receptacle 443 that is in communication with the larvae-growth chamber 475 (FIG. 14). For example, the waste material can pass through at least one waste aperture 488 (FIG. 15A) (also referred to as "waste apertures 488") in the larvae-growth chamber 475 into the waste receptacle 443. Similarly to the waste receptacle 243, waste material in the waste receptacle 443 can be diluted with water and used as a fertilizer for plants. In some embodiments, the waste receptacle 443 is removably attached to the larvae-growth chamber 405.

In some embodiments, at least one filter device 499 (FIGS. 15B, 15C) is included in at least one of the waste apertures 488 to filter excess fluids in the waste material passing through the waste apertures 488 from the larvae-growth chamber 475 into the waste receptacle 443 and control the amount of fluid in the waste receptacle 443 while preventing the larvae from escaping through the waste apertures 488. The filter device 499 includes end rings 411A, 411B, fine filter mesh structures 421A, 421B, filter material 431 and filter holder 441. The fine filter mesh structures 421A, 421B can be manufactured from any suitable material, such as stainless steel, and are of a fine mesh sufficient to prevent at least one larvae from escaping through the waste apertures 488 from the larvae-growth chamber 475. The filter material 431 can be made from filter pads used for aquarium applications, such the Aqua One™ Carbo Pad. However, any suitable material for filtering the desired amount of fluid flowing from the larvae-growth chamber 475 into the waste receptacle 443 is contemplated.

Instead of exiting the larvae-growth chamber 475 through the larvae exit aperture 478, in some cases the larvae will pupate into adult insects in the larvae-growth chamber 475. The adult insects they may exit the larvae-growth chamber 475 through at least one one-way exit structure, shown as example one-way exit nozzle structures 493 in FIG. 12A, which are configured to permit at least one adult insect that emerged in the larvae-growth chamber 475 to exit the larvae-growth chamber 475 into the egg-producing chamber structure 405, such as into the mating and oviposition chamber 420, and to inhibit the at least one adult insect which emerged in the larvae-growth chamber from re-entering the larvae-growth chamber 475 through the at least one one-way nozzle structure. Although the one-way nozzles 493 are shown, it is understood that any other suitable structures that permit the adult emerged insects to travel into the egg-producing chamber structure 405 from the larvae-growth chamber 475, but inhibits re-entry of those adult emerged insects into the larvae-growth chamber 475 are also contemplated. For example, apertures suitably sized to permit the adult emerged insects to travel from the larvae-growth chamber 475 into the egg-producing chamber structure 405 but hinder re-entry of the emerged adult insects into the larvae-growth chamber 475 may be included.

Similarly to the system 100, the emerged adult insects will likely die in the mating and oviposition chamber 420. To assist with the removal of the dead insects and other debris, the system 400 can include an access sleeve 498 (FIGS. 16A to 16C) that is configured to provide access to a component interior of the egg-producing chamber structure 405. For example, the access sleeve 498 may permit access to the oviposition region 425 for removal and/or cleaning of the oviposition region 425. As another example, the access sleeve 498 can assist in cleaning an interior surface of the egg-producing chamber structure 405, such as an interior surface 502. The access sleeve 498 can be removably attached to the interior of the egg-producing chamber structure 405, such as to the mating and oviposition chamber 420. The access sleeve 498 is configured to be manipulated by a user's hand, arm or other implement to contact various surfaces of the system 400. The access sleeve 498 may include a closure, such as a drawstring closure 504, at an end 506. When the end 506 is open (the closure, as the drawstring closure 504, is not actuated), a user is able to slip their arm through the sleeve and hold a cleaning item, such as a sponge, in their hand or pick up dead insects with their fingers through the open end 506 of the access sleeve 498. The dead insects can be disposed of through the holes 508 in the mating and oviposition chamber 420 (FIG. 16A) and/or through the feed hatch 473 into the larvae-growth chamber 475. The dead insects may also be removed from the mating and oviposition chamber 420 and disposed of externally of the system 400. Some users prefer not to touch the dead insects directly. In such cases, the end 506 can be closed (the closure, as the drawstring closure 504, is actuated), and the user is able to slip their arm into the access sleeve 498 and grasp the dead insects through the material of the access sleeve 498. It is understood that the closure need not be a drawstring, but can include a variety of closure mechanisms such as buttons, hook-and-loop closures and clips to close the end 506.

The access sleeve 498 may be manufactured from a variety of materials. For example, the access sleeve 498 may be manufactured from cotton or a net of woven material, such as nylon. In some embodiments, at least a portion of the access sleeve 498 is manufactured from a material that has a texture sufficient to allow debris and/or dead insects to adhere to the access sleeve 498. The pupation chamber 415 may be removed from the egg-producing chamber structure 405 in order to attach and use the access sleeve 498 to the remainder of the egg-producing chamber 405 (e.g., the mating and oviposition chamber 420). Insects that are removed from the egg-producing chamber structure 405 may be deposited into the larvae-growth chamber 475 to feed the maturing larvae or disposed of in another manner.

Figure 17:
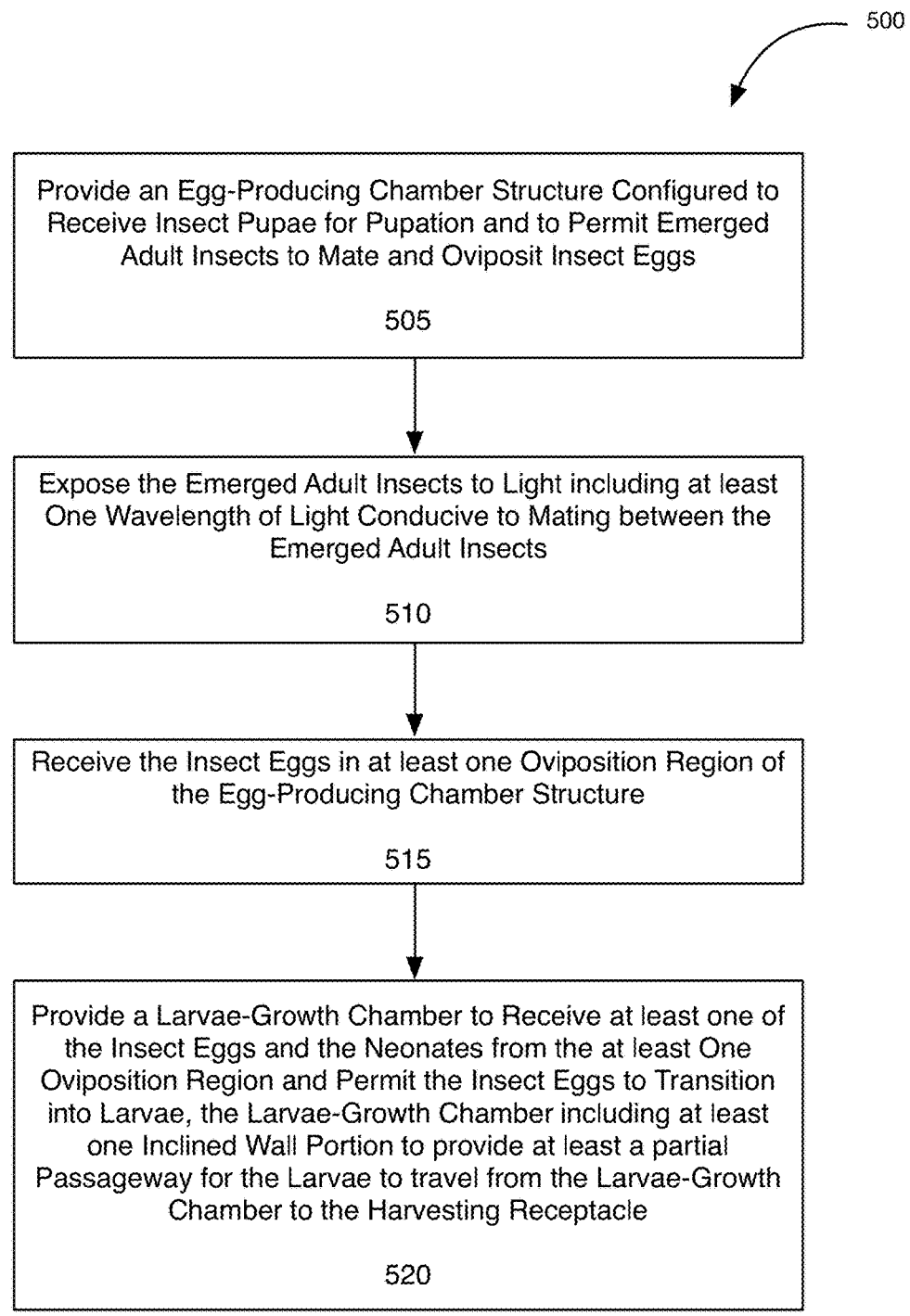
FIG. 17 depicts a flowchart of a method for breeding and harvesting insects, according to a second set of non-limiting embodiments.

FIG. 17 depicts a flowchart of an example method 500 for breeding and harvesting insects. In order to assist with in the explanation of the method 500, it will be assumed that the method 500 is performed using the system 400. However, it is to be understood that the system 400 and/or the method 500 can be varied, and need not work exactly as discussed herein in conjunction with each other, and that such variations are within the scope of the described systems and methods. It is also understood that the method 500 need not be performed in the exact sequence as shown unless otherwise indicated; and likewise various blocks may be performed in parallel rather than in sequence; hence the elements of the method 500 are referred to as "blocks" rather than "steps". It is also understood that the method 500 can be implemented on variations of the system 100 as well.

At block 505, an egg-producing chamber structure, such as the egg-producing chamber structure 405, that is configured to receive insect pupae for pupation and to permit the emerged adult insects to mate and oviposit insect eggs is provided. As in the egg-producing chamber structure 405, the provided egg-producing chamber structure can include one or more chambers. In some embodiments, multiple insect lifecycle stages are at least started in the same chamber. In some embodiments, one or more of insect lifecycle stages are performed in separate chambers. Structures configured to provide a hydrating fluid for the emerged adult insects can be provided, such as the nutrient compartment 448.

At block 510, the emerged adult insects are exposed to light including at least one wavelength of light that is conducive to mating between the emerged adult insects, such as the wavelength of light 458. In some embodiments, exposing the emerged adult insects to light including the at least one wavelength of light conducive to mating includes exposing the emerged adult insects to ambient light (e.g., to light that is ambient to the chamber structure). In some other embodiments, exposing the emerged adult insects to light including the at least one wavelength of light conducive to mating includes exposing the emerged adult insects to artificial light. For example, the lamp 463 may be used to perform block 510.

At block 515, the insect eggs are received in at least one oviposition region of the egg-producing chamber structure, such as the oviposition region 425 of the egg-producing chamber structure 405.

At block 520, a larvae-growth chamber that is in communication with the at least one oviposition region 425 so as to be configured to receive at least one of the insect eggs and the neonates of the insect eggs from the at least one oviposition region 425, such as the larvae-growth chamber 475, is provided. The provided larvae-growth chamber is configured to permit the insect eggs and/or the neonates of the insect eggs to transition into larvae and to hold feed material for the larvae. For example, as described above, the larvae-growth chamber 475 may be round in shape in order for the larvae to grow efficiently and the walls of the larvae-growth chamber 475, such as walls 468, can be opaque, semi-opaque or partly opaque. The larvae-growth chamber 475 may also include the feed hatch 473 that can be opened to deposit the feed material into the larvae-growth chamber 475. As stated above, the larvae-growth chamber 475 may be separable from the egg-producing chamber structure 405 such that the feed material can be directly deposited into the larvae-growth chamber 475.

The provided larvae-growth chamber will also include at least one inclined wall portion, such as the peripheral wall 468, that is configured to provide at least a partial passageway for the larvae to travel from the larvae-growth chamber to a harvesting receptacle, such as the harvesting receptacle 402.

Figure 20:
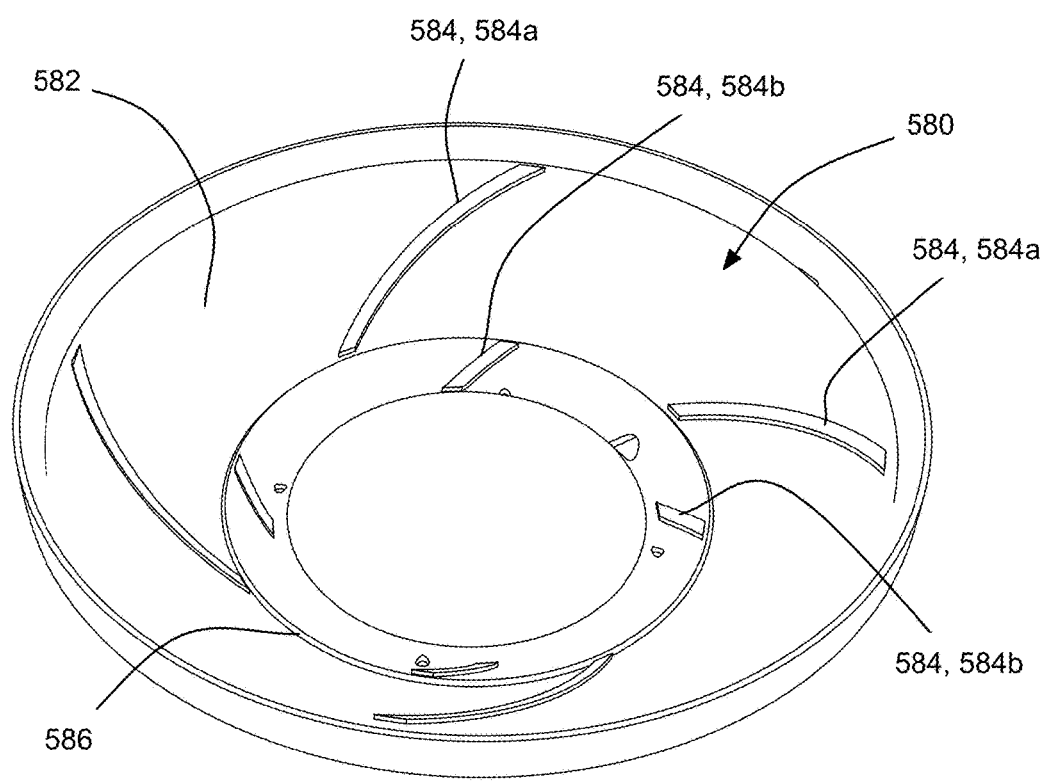
FIG. 20 is a perspective view of an alternative harvest structure.

Reference is made to FIG. 20 which shows an alternative harvest structure 580. The harvest structure 580 includes an inclined wall 582 that includes at least one helical projection 584. The helical projections 584 assist the larvae (not shown) in climbing the inclined wall 582. In the example shown, the helical projections 584 may be divided into upper and lower helical projections 584a and 584b respectively, with a circumferential ledge 586 between them.

Figure 21A:
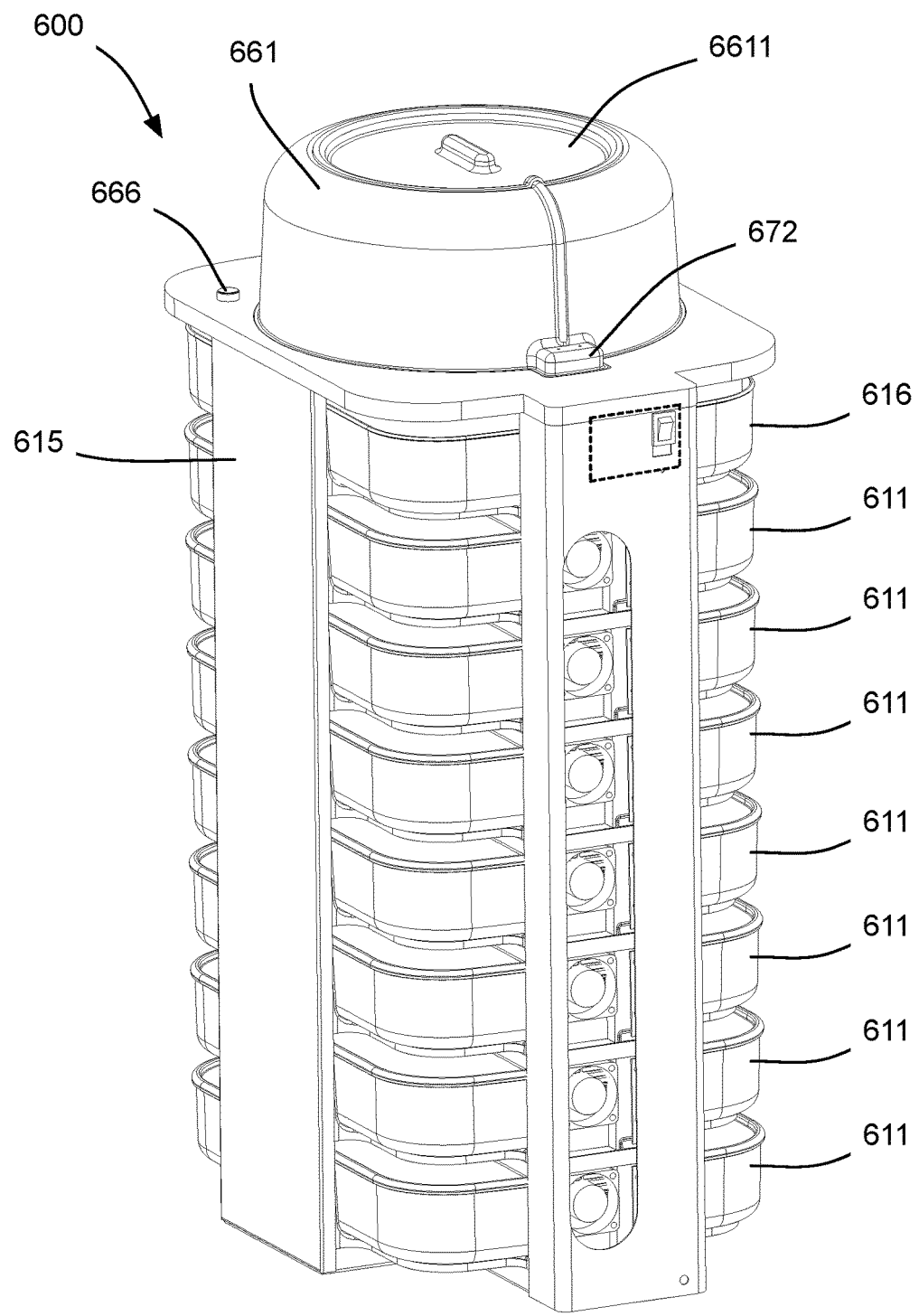
FIG. 21A is a perspective view of an alternative embodiment of the system.
Figure 21B:
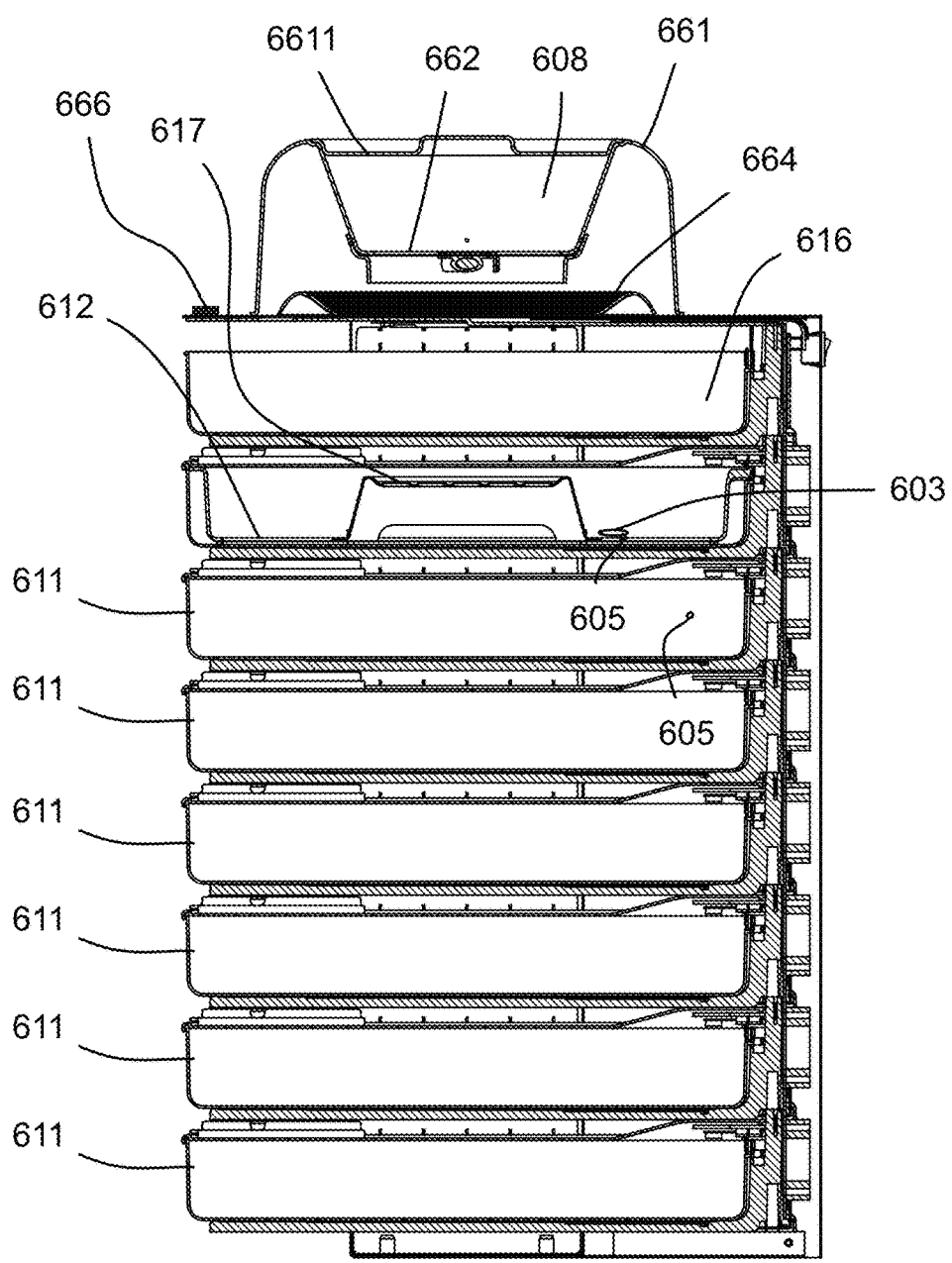
FIG. 21B is a sectional elevation view of the system shown in FIG. 21A.

Referring to FIG. 21A and FIG. 21B, a system in accordance with an alternative embodiment of the present disclosure is shown at (600), and includes at least one larvae-growth chamber (611). In the embodiment shown in FIGS. 21A and 21B, there are seven larvae-growth chambers (611), however, other numbers of larvae-growth chambers (611) are possible.

The walls of the larvae-growth chambers (611) may be very smooth and glossy in order to prevent worms from crawling out on the walls of the chambers (611). The chambers (611) can be made out of plastic materials or any other material such as metal that has a smooth surface finish. Food grade ABS may be used as it is light-weight and easy to clean. The system (600) further includes at least one harvest receptacle (616).

Figure 22:
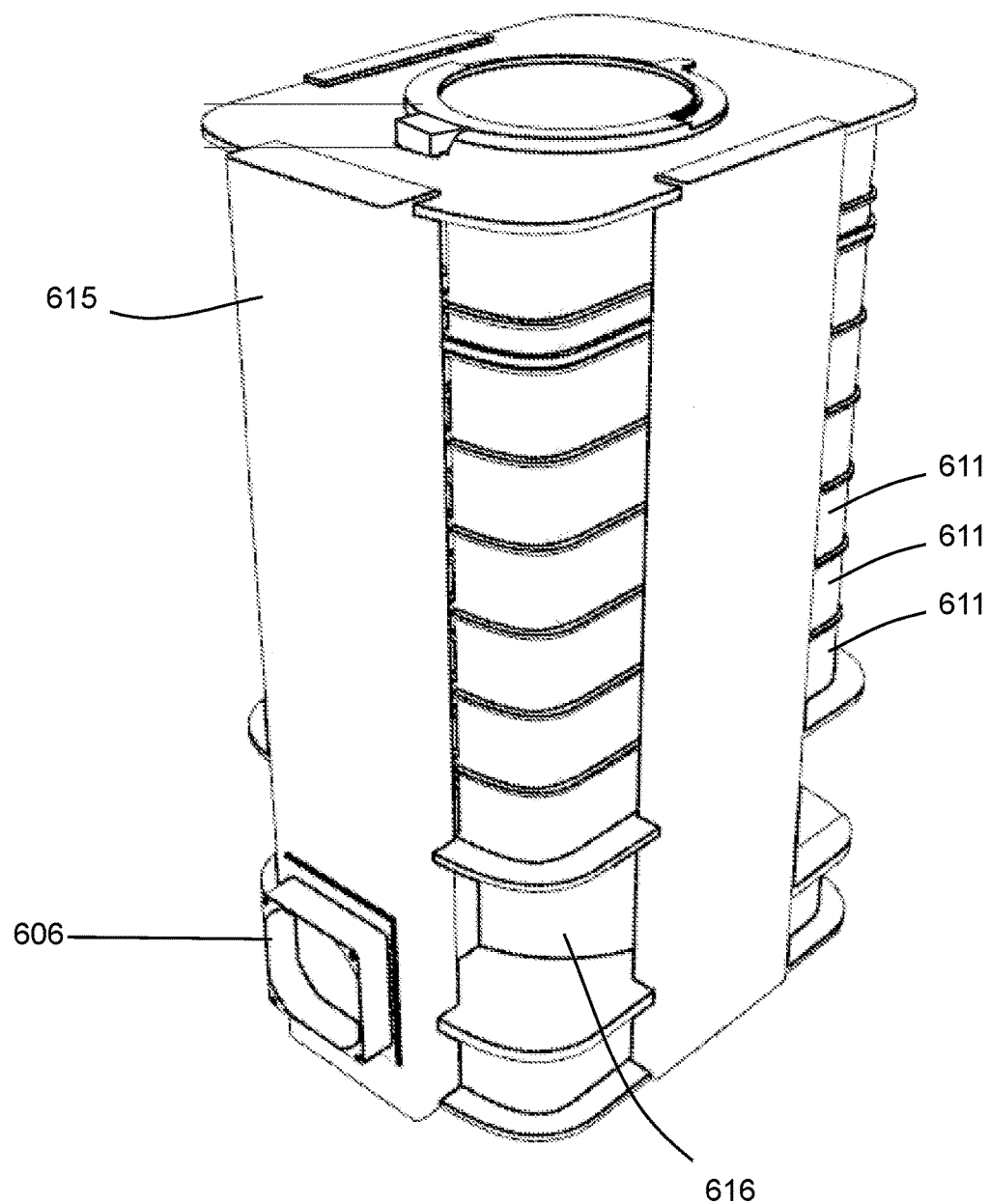
FIG. 22 is a perspective view of a variant of the system shown in FIG. 21A.
Figure 23:
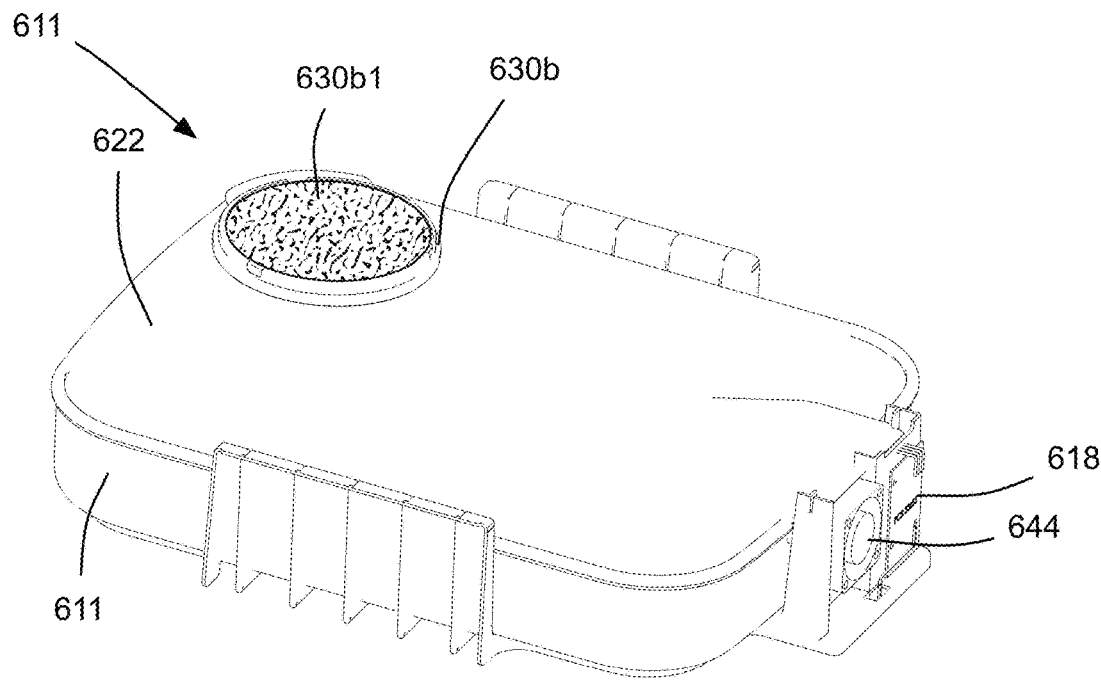
FIG. 23 is a perspective view of a larvae-growth chamber that is part of the system shown in FIG. 21A in a shelf.
Figure 24:
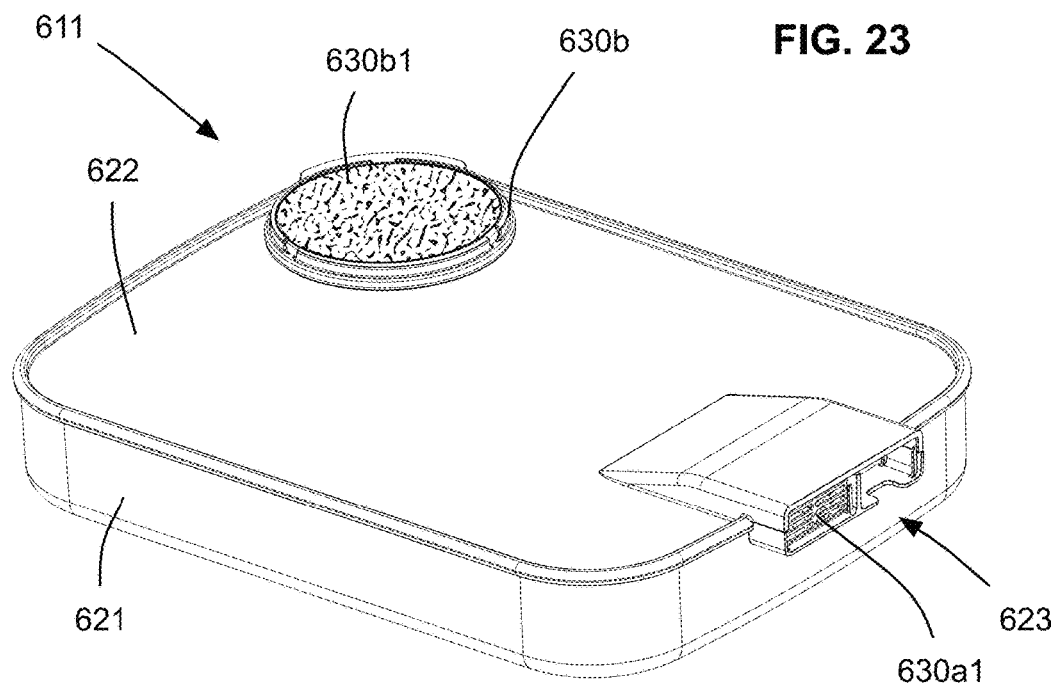
FIG. 24 is a perspective view of a larvae-growth chamber that is part of the system shown in FIG. 21A.
Figure 25:
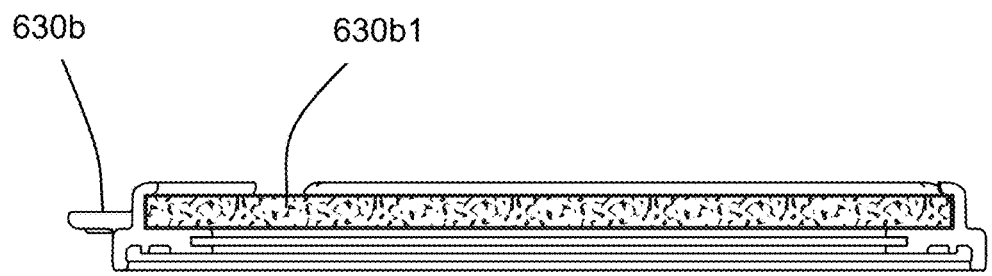
FIG. 25 is a sectional side view of a removable carbon filter which can be slid into a cover of the larvae-growth chamber.
Figure 26:
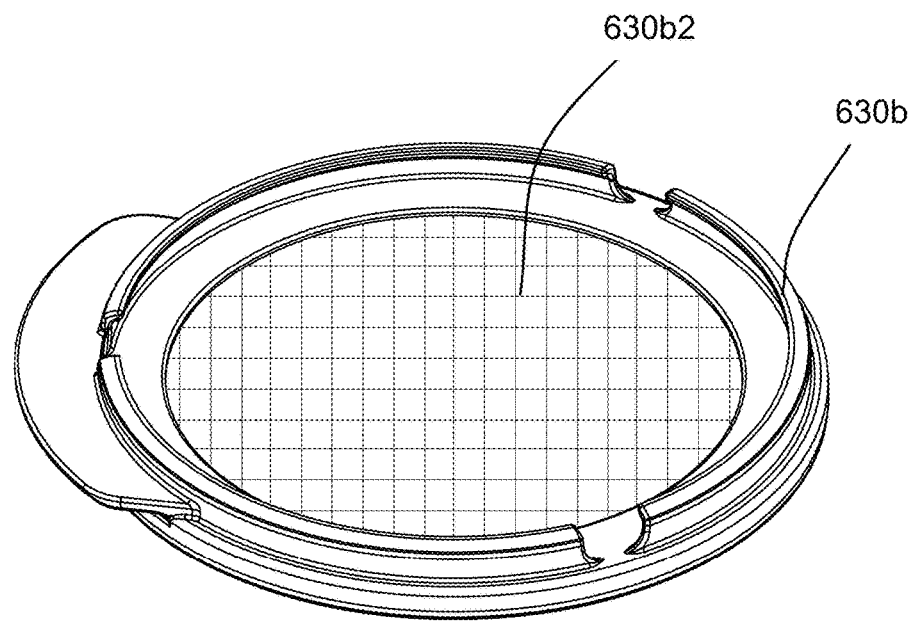
FIG. 26 is a perspective view of the cover shown in FIG. 25.

In some embodiments of the system (600) there is a cooling element (e.g. a Peltier element) in communication with the harvest receptacle. An example is shown at 606 in an alternative embodiment illustrated in FIG. 22. This cooling element 601 allows the harvest area to be cooled down to 15° C.-8° C. in order to chill the harvested larvae (shown at (601)) and prevent from any further development into another lifestage.

In some embodiments the system (600) is structurally supported by a frame (615).

The system (600) may further include an oviposition inlay (612) with two oviposition regions (612a), which is, in some embodiments, in communication with the larvae-growth chamber tray(s) and is removable from the system (600). The larvae-growth chamber tray (611) and the oviposition inlay (612) are typically pulled out from the frame (615) by a few centimeters in order to allow feeding of the insects inside. They can also be fully removed for cleaning and/or disassembly of the system 600. The oviposition inlay (612) can be in communication with each of the larvae-growth chamber trays (611) and features a mesh bottom and contains a pupation area (617) (also referred to as a pupae area (617)) in communication with the oviposition regions (612a). In the pupation area (617), pupae (602) may be placed manually. There, the adults (603) hatch out of the pupae and seek their way into the oviposition regions (612a). The surface of the pupation area (617) can be perforated, may include a mesh or may be shaped in any suitable way. The surface of the pupation area (617) may have a three-dimensional structured surface (i.e. with textures, bumps and depressions), which provide grab points for the an adult (603) in the event that it is born on its back. In embodiments in which apertures are provided in the pupation area (617) it is possible that the apertures can be sized to permit eggs to fall through in the event that an adult lays eggs in that area (617).

In the present example embodiment the oviposition regions 612a each have a mesh bottom. The mesh can be made of stainless steel or any other material. The mesh typically has a hole size of about 2-3 mm. The oviposition regions (612a) of the oviposition inlay 612 give the adults (603) a surface to live on and permit eggs (shown at (605)) that the adults (603) lay to fall through so that the eggs (605) are protected from being cannibalized. The surface of the oviposition region 612a may have holes as shown in the figures, but additionally or alternatively, the oviposition regions 612a may have a three dimensional structured surface with textures, bumps and depressions, which may promote egg-laying in the adults (603).

In some embodiments the hole size of the oviposition inlay (612) might vary. The pupation area (617) may look similar to a tower that is designed so that adults can slide down from the pupae area (617), however the surfaces leading from the pupae area (617) down to the oviposition regions (612a) are slanted and of glossy surface so that the adults (603) cannot go back up again. This is to prevent the adults (603) from eating the pupae (602). Once in the oviposition regions (612a), the adults (603) may be fed any suitable food, such as kitchen vegetable scraps and oats, or on dedicated feed provided by a commercial seller. The adults (603) will start to mate and lay eggs (605) through the mesh bottom. The eggs (605) fall through to the larvae growth chamber tray (611) where they grow into larvae. In some embodiments there is a surface below the oviposition inlay which additionally stimulates the adults to oviposit their eggs (605). This can, for example, be a structure made out of cardboard, wood or other organic materials.

Each of the larvae-growth chamber trays (611) has a bottom (621) to hold the larvae (601) and their feed or substrate with removable lid (622) sitting on top of the bottom (621). This lid (622) is removed for cleaning or disassembly of the tray (611). Each of these removable lids has another removable round lid (630b) and a sensor aperture (623) that is configured to permit the mounting of a humidity and temperature sensor for the measurement of humidity and temperature in each larvae-growth chamber tray. The sensor aperture (623) is covered by a carbon filter (630a1) in order to prevent odors from escaping from the system (600).

The round lid 630b is a cover for an aperture on the larvae-growth chamber tray lid (622) and is fully removable from the lid (622). The round lid 630b has a screen insert (630b2) and a removable carbon filter (630b1) which sits on top of the screen insert.

The carbon filters (630b1) and (630a1) substantially prevents odors from escaping from the system and small pest insects to enter the system. When the carbon filter is removed, the screen insert (630b2) allows small particles such as waste, dirt and manure of the larvae (601) to leave the system when the user removes the growth chamber from the system (600) and shakes the larvae-growth chamber with closed lid. The round lid can also be fully removed, for example in order to pour out the larvae (601) contained by the larvae-growth chamber.

The round lid (630b) allows air to move into the larvae-growth chamber 611 through the carbon filter.

Figure 30:
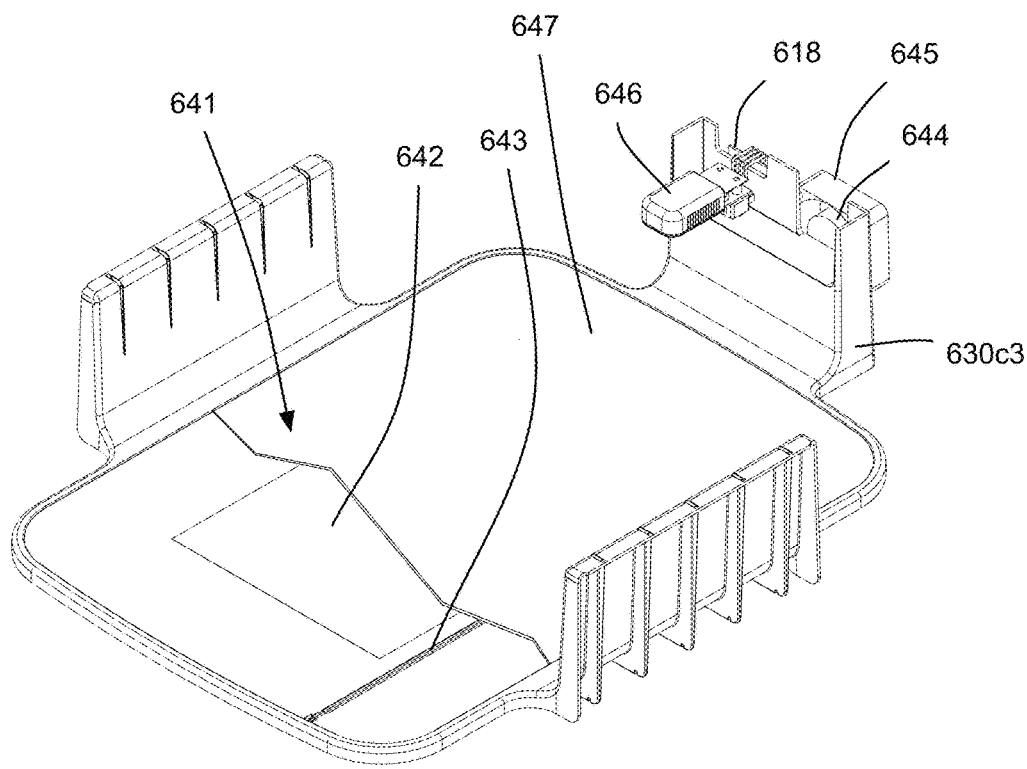
FIG. 30 is a perspective view of a shelf structure that is usable to hold a larvae-growth chamber that is part of the system shown in FIG. 21A.

FIG. 30 illustrates a shelf module that is designed to contain the electronics of the system (600) as well as to provide structural support to hold the larvae-growth chamber trays. It contains a heat source (642) (which may be, for example, a heat 'sticker' or a plate heater) with an integrated thermistor, an LED (643), a humidity and temperature sensor (646), a fan (645), a PCB board (618) that connects the electronics to the PCB motherboard (that is itself mounted within the frame 415 but which is not specifically shown) and a microswitch (unnumbered, but which is positioned below the sensor 646). The heat source (642), the LED (643) and corresponding cables are covered by an aluminum plate (647) in order to protect the electronics while still transmitting heat to the larvae-growth chamber tray sitting on top of it. All electronics are controlled by the PCB motherboard and connected to it by PCB connector boards in each shelf module. The sensor (646) and microswitch are attached to the shelf module (630c3) and inserts automatically into the growth chamber tray through its aperture (623) where it measures humidity and temperature.

The heat source, the light source, the fan, the temperature and humidity sensor which monitors the temperature and humidity in the larvae-growth chamber, and the PBC board connected to the microswitch and the PCB mother board programmed to control the microclimate in the larvae-growth chamber, together constitute a microclimate control system. It will be understood that the control system may have fewer or more elements depending on the level of control that is desired for the particular application.

Figure 31:
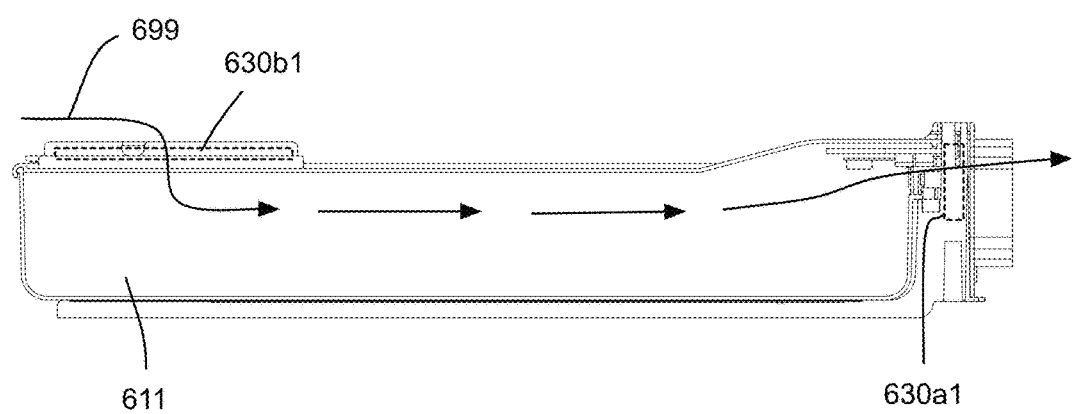
FIG. 31 is a perspective view of a larvae-growth chamber that is part of the system shown in FIG. 21A.

Ideal growing temperatures are between 25-31° C. with a relative air humidity of 55-75%. In order to keep an ideal environment for the mealworms inside the system (600), each growing tray is monitored for its temperature and humidity. A central control board (676) logs the data and operates the fans accordingly. The fans (644) are equipped with a filter pad (630a1) in order to prevent odors to escape from the system (600). If humidity levels exceed 75% humidity, the fan is activated and pulls air (shown at (699) in FIG. 31) from the outside through the round lid (630b), throughout the growth chamber tray (611) and through the carbon filter (630a1) to the outside again.

If the thermistor in the bottom (642 (integrated in heat sticker) measures a temperature below 27° C., the heat source is activated and heats up to 29° C., heating the larvae (601) to an optimum temperature of 28° C. through the bottom of the larvae-growth chamber tray. Once the user places the oviposition layer into the larvae-growth chamber tray, a part of the oviposition layer pushes the microswitch in the corresponding shelf module (630c3). The system then recognizes that the age of the larvae (601) is 0, as new eggs (605) are being laid into the larvae-growth chamber tray once the oviposition layer is inserted, therefore the age of the larvae (601) is 0 days. Harvest age is 98 days in a current embodiment.

Figure 32:
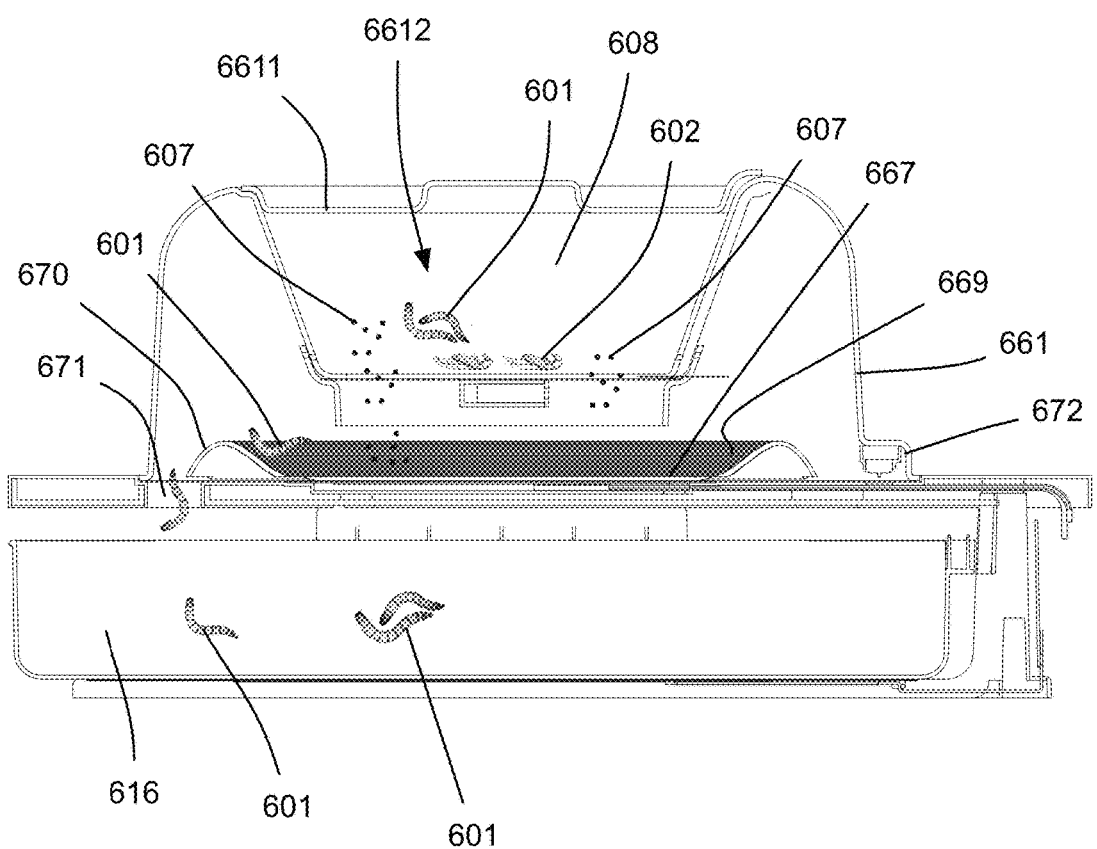
FIG. 32 is a sectional side view of a portion of the harvesting structure that is shown in FIG. 29.

A harvest button (666) can be located on the side structure or somewhere else on the system (600) and activates the harvest mechanism. FIG. 32 illustrates the harvest mechanism area. This harvest mechanism can also be described as a separation mechanism. Once the insects are ready for harvest after a certain amount of time (in current embodiment 98 days or more; larvae (601) are 5-6 mm length by then and 0.1 g per larvae (601) of weight), the respective larvae-growth chamber tray is emptied manually into the harvest area in order to separate the live, healthy larvae (601) from the rest. The harvest mix contains the harvest-aged larvae, some percentage of which might have already entered the next lifestage (pupae). The harvest mix also, however, contains carcasses and other detritus. This harvest mechanism is fully removable from the rest of the system (600), and connects to the rest of the system (600) by a magnetic connector (672) that connects it to power when attached.

The harvest mechanism includes a harvest cap (661) with a harvest lid (6611) that prevents larvae (601) or dirt to escape the system (600) when the harvest mechanism is switched on.

The harvest cap and lid cover the harvest process and avoid that larvae, dirt or other material leave the system (600). In an alternative variation of the system (600) an additional surface may be added on the inside as a crevice for the worms to preferably harvest in this area.

Figure 33:
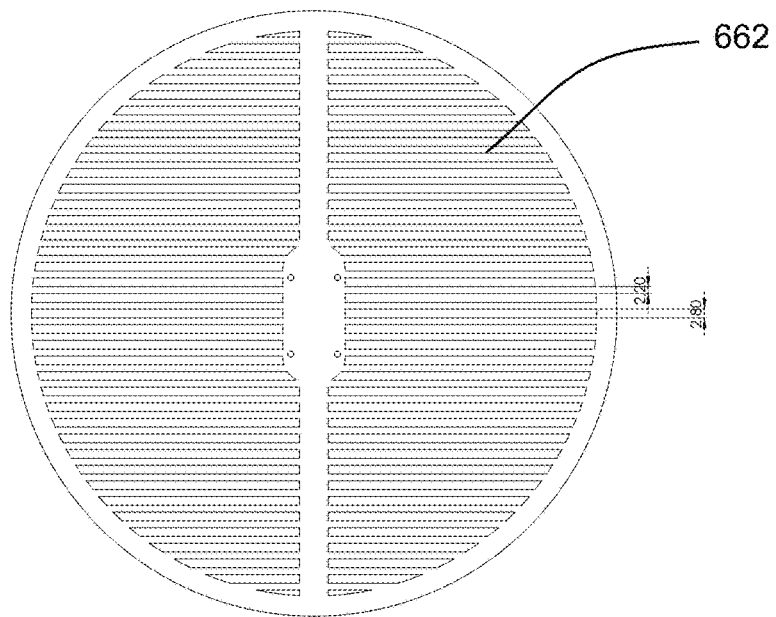
FIGS. 33 and 34 are plan views of a sieve that is usable to help harvest prepupae which can be used as part of the system shown in FIG. 21A.
Figure 34:
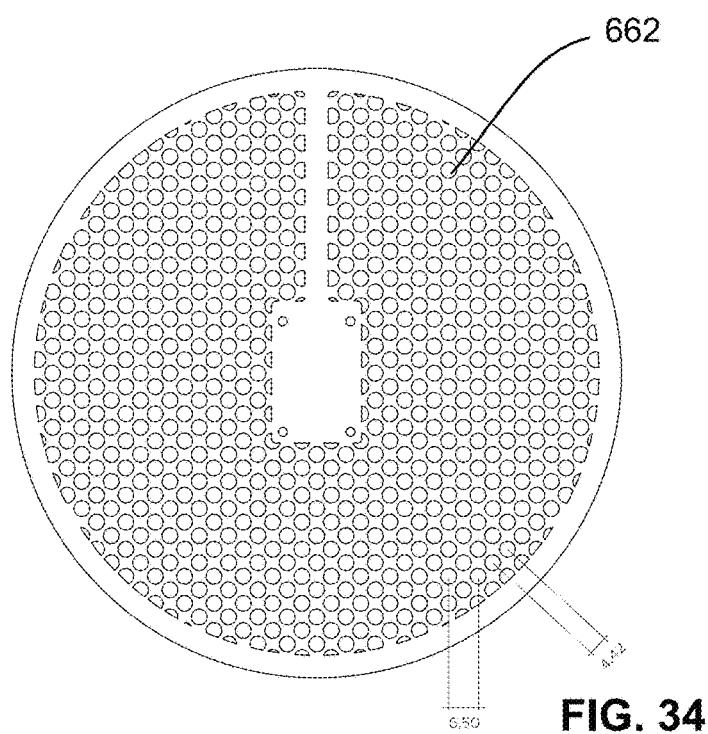
Figure 35:
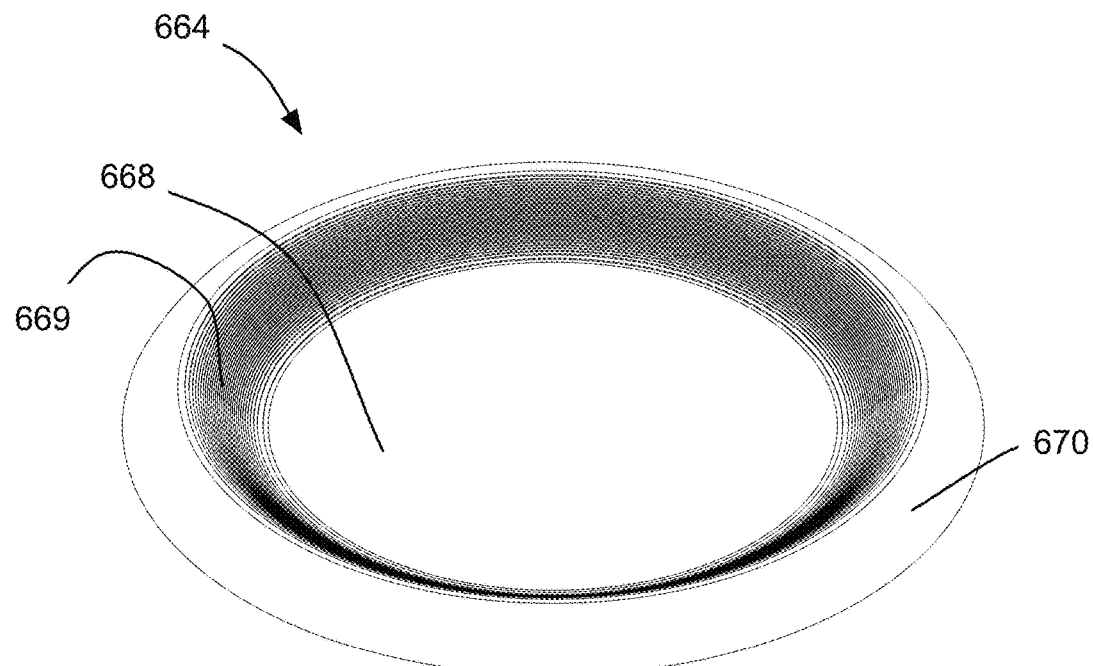
FIG. 35 is a perspective view of a harvest plate that is part of the system shown in FIG. 21A.
Figure 36:
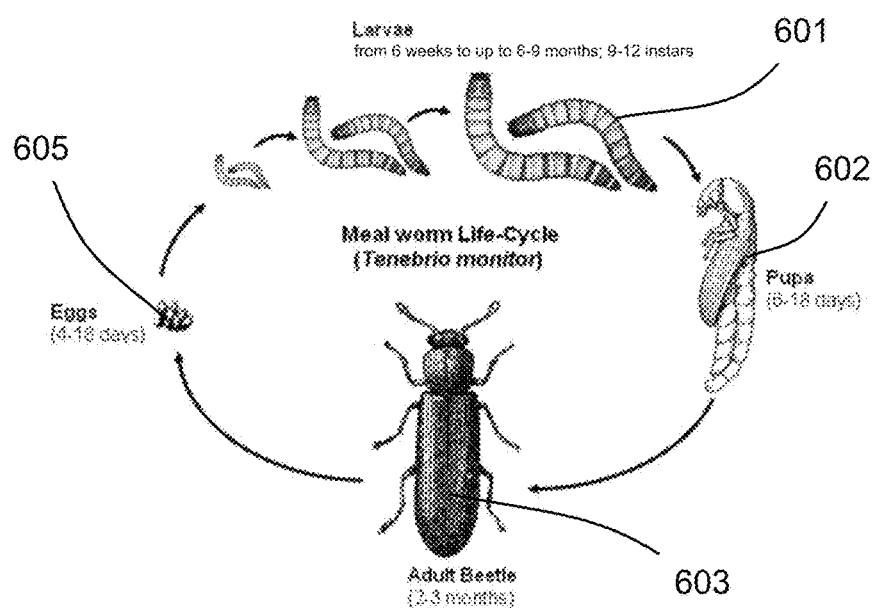
FIG. 36 illustrates the lifecycle of the insect: mealworm (*Tenebrio*)

The harvest cap (661) contains a sieve mesh membrane (662) with a vibrator motor (663) attached to it. Below is a harvest plate (664) that sits removably on a heat source (665). Below the removable harvest area sits the harvest tray (616) that has the function to collect the separated fresh larvae (601). The harvest tray (616) can be taken out fully from the system (600) in order to harvest the larvae (601), for example to serve as a human food or as pet food. In the current embodiment the harvest tray (616) is made from acrylic, however it may alternatively be made out of metal or any other suitable materials. Two embodiments of the sieve mesh 662 are shown in FIGS. 33 and 34.

In an alternative variation of the system (600), there is a dirt bucket located beneath the harvest plate (664). (only beneath the harvest plate) In such an alternative version the harvest plate has fine holes through which fine dirt such as the sandy manure of the larvae (601) can fall through and collect in such dirt bucket.

The harvest mix (6612) contains pupae (602), larvae (601) and dirt such as manure, dust and other detritus (shown at 607). After the harvest mix is poured into the harvest area (shown at 608), the harvest button is activated. The vibrator (663) starts vibration and allows the harvest mix to go through it slowly onto the harvest plate (664). The vibration allows the sieve mesh to vibrate and to accelerate the separation process as well as to time it in a certain way so that there are never too many larvae (601) on the harvest plate. Only the pupae (602) will stay on top of the mesh sieve (662). They can then be collected and put back into the pupation area in order to emerge into adults (603) (e.g. beetles) again and restart the lifecycle. The holes on the sieve (662) have approximate dimensions of 2 mm-4 mm in length (other dimensions in other embodiments possible) and are shaped so that the pupae (602) stay on top of the membrane while all the other worms, the frass, carcasses and other detritus go through the holes into the next area. The sieve mesh is big enough to let the larvae (601) and dirt go through but prevents the pupae (602) from going through. The live larvae (601), together with dead larvae, frass and other detritus enter the harvest plates. A heat source (665) is attached beneath the harvest plate (664) and heats the harvest plate (664) up in a certain rhythm. In an alternative embodiment, the heat source (665) is combined with a vibration element in order to stimulate even quicker escape of the live worms away from the frass, carcasses and other detritus into the harvest tray (616). In an alternative embodiment, the heat source is replaced by a vibration element.

In an alternative embodiment, the heat source is replaced by, or provided in combination with a vibration element in order to stimulate quicker escape of the live worms away from the frass, carcasses and other detritus into the harvest tray (616).

In an alternative embodiment, the heat source is provided in combination with a light source in order to stimulate quicker escape of the live worms away from the frass, carcasses and other detritus into the harvest tray (616) (the larvae (601) are light-sensitive). In alternative embodiments, there may be light, vibration or heat only, or any suitable combination of any of these features in order to stimulate quicker escape of the live worms away from the frass, carcasses and other detritus into the harvest tray (616).

There is provided at least one larvae motivation element selected from the group of larvae motivation elements consisting of: a heat source, a vibration source, a mechanical agitator, and a light source, wherein the at least one larvae motivation element is positioned and activated to act on larvae (601) urging the larvae (601) to leave the harvest plate (664) and travel to the harvest tray (616).

The harvest plate (664) may be shaped similar to a plate, with a base surface (668) and surrounded by an inclined surface (669) that allow frass, carcasses and other detritus to stay on the plate (664) while the live larvae (601) can crawl off without pushing the frass, carcasses and other detritus down into the harvest tray. The harvest plate (664) may be made out of aluminum in the current embodiment but might be out of mild steel, other metals, ceramics or other heat-transmissive materials. The plate (664) is shaped so that the detritus stays in the middle of the plate, while the active and healthy larvae (601) are able to crawl up the rim (i.e. surface 669) of the plate (which may be provided with a rough surface or little steps engraved in the surface in order to facilitate climbing thereon by the larvae (601). The outside rim portion (shown at 670) of the harvest plate has a very smooth surface. In this way, the larvae (601) crawl on the rough rim and slide down the slippery outside rim in order to enter and fall through a passageway (671) into the harvest tray (616) for collection.

Figure 29:
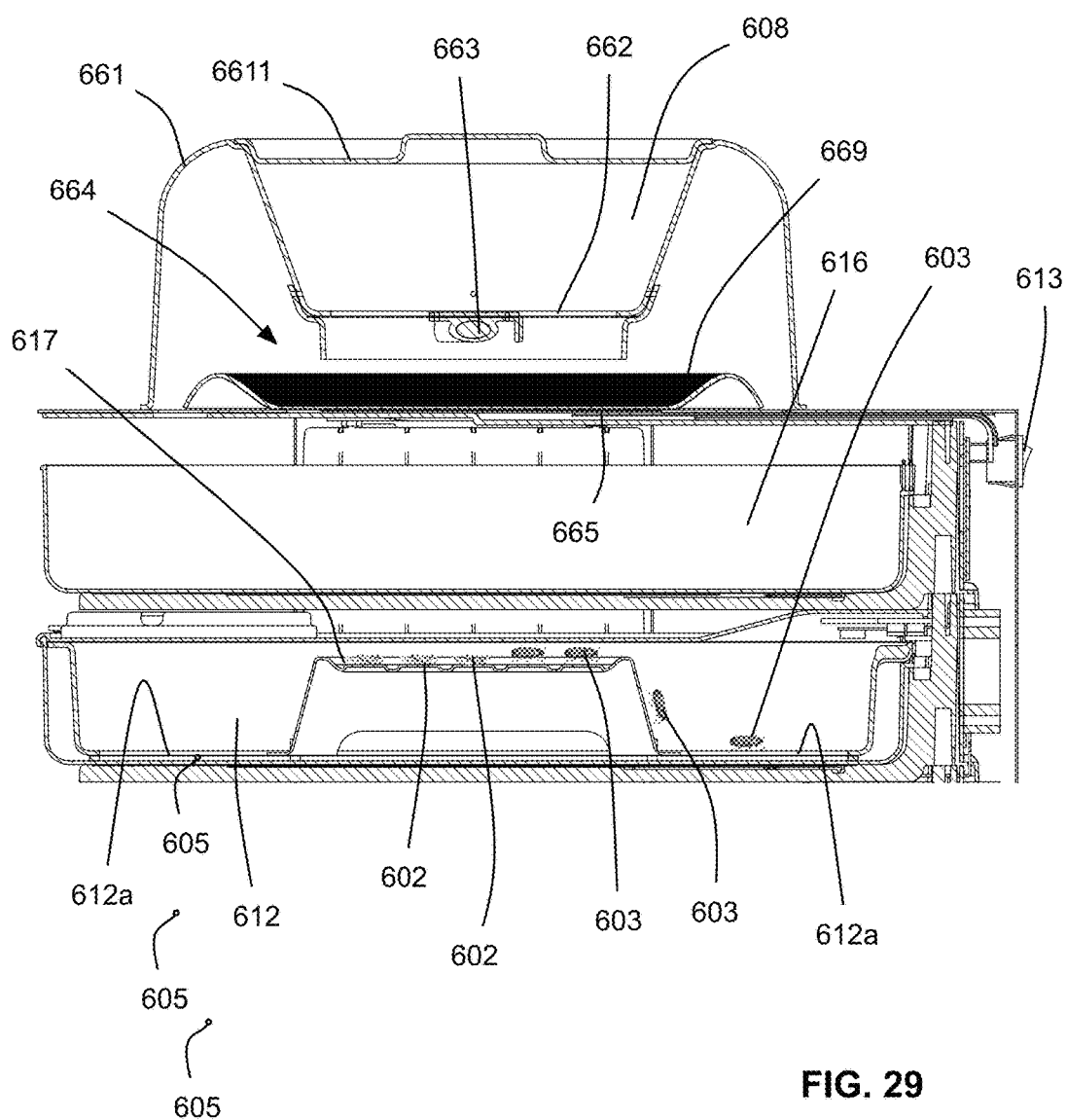
FIG. 29 is a sectional side view of a harvesting structure that is part of the system shown in FIG. 21A.

FIG. 29 illustrates the lifecycle of the mealworm (*Tenebrio molitor*). The adult beetle lives for approximately 2-3 months. It may be preferable to provide darkness and food materials such as vegetable kitchen scraps (e.g. carrots, apples, etc.) and/or oats and grain. The insects raised in the current embodiment of the system (600) may also be fed on alternative materials. They may be fed on pre-processed feed or germ plasm, or on any other suitable food. In embodiments directed to certain types of beetle, it will be noted that each female beetle may lay around 5 eggs/day, with an 80% success rate, which results in 28 larvae/week. At 27° Celsius eggs (605) may only take about 4.4 days to hatch. In cooler temperatures, however, it might take up to 18 days. The larvae (601) hatch after these 4-18 days and can live for up to 9 months. However under optimal conditions, they might only take 6 weeks to reach harvest size. Harvest size in the present disclosure is defined when a worm reaches the weight of 0.1 g. In some embodiments, the system (600) allows the mealworms a minimum of 6 weeks to grow into a suitable size for harvesting. This time period may be different in other embodiments. Accordingly, the number of larvae-growth chamber trays 611 may be different in different embodiments.

After this period of time, the mealworm turns into a pupa. Inside the pupa, the beetle develops and it takes 6-18 days in order to do this. The ideal temperatures for beetles and mealworms are between 25° C.-31° C. air temperature and 55-75% air humidity.

The example setup provides these parameters through control of the microclimate as described.

The frass and other detritus, diluted with water or non-diluted, may be used as a fertilizer for plants.

Figure 27:
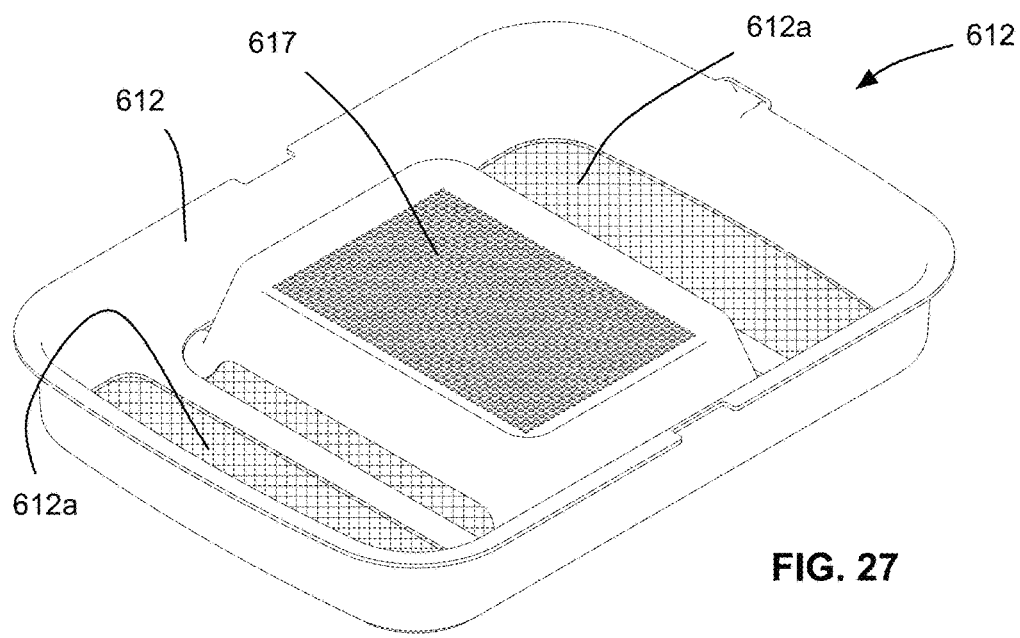
FIG. 27 is a perspective view of a tray including two oviposition regions and a pupation region.
Figure 28:
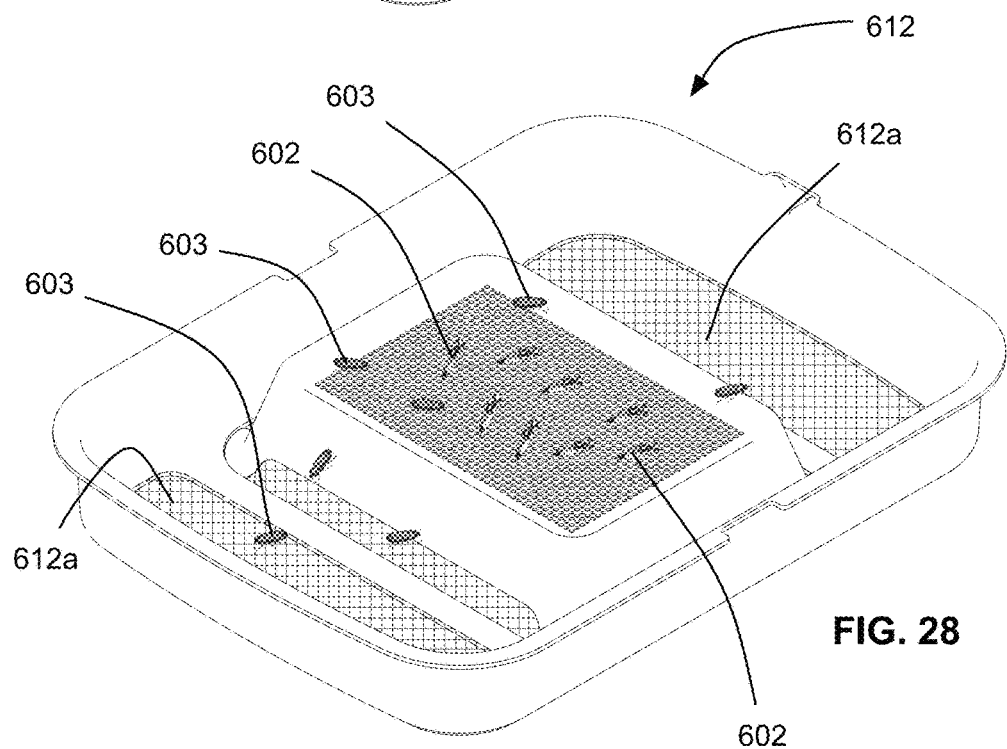
FIG. 28 is a perspective view of an oviposition inlay including two oviposition regions and a pupation region.

FIG. 27 shows two versions of holes in the perforated mesh in the pupa harvest (662). The holes are specifically shaped so that the pupa are kept on the surface, while the rest of the frass, carcasses and other detritus, and worms go through the mesh due to the relatively big openings. These openings currently have a diameter of 3.5 mm. These measurements might vary in alternative embodiments. Also, the shape of the holes might vary in alternative embodiments. 27.1 shows the position of the vibration motor. The material in the present example is flexible PE sheet. In alternative embodiments the materials can be other plastic materials or even fibres or textiles.

Figure 37:
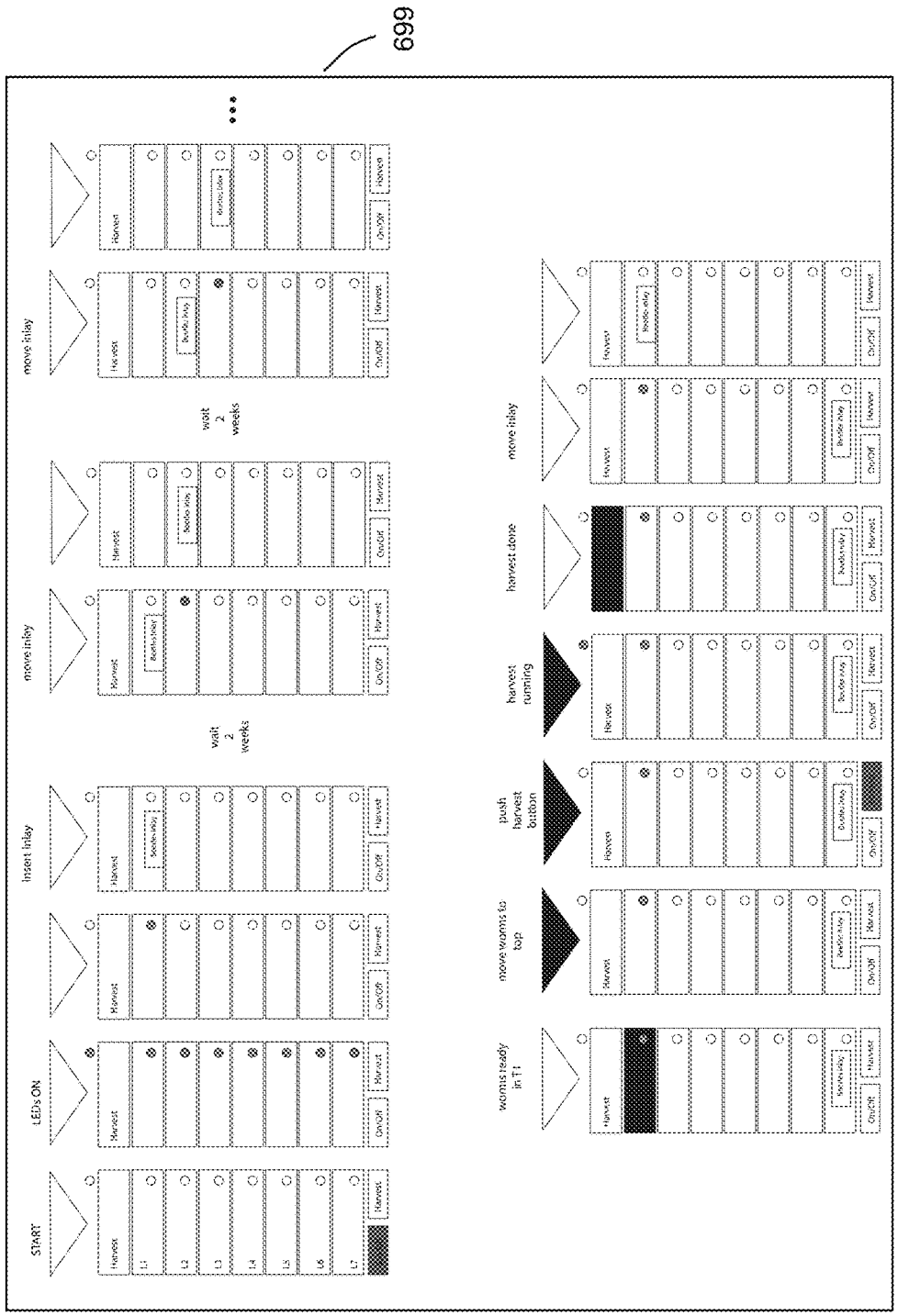
FIG. 37 is an illustration from a user manual for the system shown in FIG. 21A.

FIG. 37 illustrates a diagram 699 from a user manual for the system 600 to show users how to use a particular embodiment of the system 600. It is also understood that the manual may also vary depending on the embodiment of the system 600 being described.

According to some embodiments, the described systems and methods for breeding and harvesting insects provide an enclosed environment for the insects to progress through an entire lifecycle, from pupation to adulthood to death. During at least one stage of the insects' lifecycle, the insects may be harvested. According to some embodiments, the yield may be less or more than 500 grams. According to some embodiments, the described systems are configured to allow a user to observe at least one stage of the insects' lifecycle. For example, features, such as the protective cap 223 (when configured to be at least partially transparent) can be included.

Persons skilled in the art will appreciate that there are yet more alternative embodiments and modifications possible, and that the above examples are only illustrations of one or more embodiments.

What is claimed is:

1. A system for breeding and harvesting insects, comprising:
   an egg-producing chamber structure configured to receive insect pupae for pupation and to permit emerged adult insects to mate and oviposit insect eggs;
   at least one oviposition region in the egg-producing chamber structure configured to receive the insect eggs and apertured to permit at least one of the insect eggs and neonates of the insect eggs to pass therethrough;
   at least one larvae-growth chamber in communication with the at least one oviposition region so as to be configured to receive the at least one of the insect eggs and neonates of the insect eggs, wherein the larvae-growth chamber is further configured to permit the at least one of the insect eggs and neonates of the insect eggs to transition into larvae and to hold feed material for the larvae;
   a harvesting receptacle positioned to hold larvae; and
   an inclined surface positioned to receive larvae from the at least one larvae-growth chamber, and to provide a passageway for the larvae to travel to the harvesting receptacle.

2. The system for breeding and harvesting insects of claim 1, wherein the egg-producing chamber structure includes a pupation chamber having at least one aperture configured to allow the emerged adult insects to exit the pupation chamber.

3. The system for breeding and harvesting insects of claim 2, wherein the egg-producing chamber structure includes a mating and oviposition chamber in communication with the pupation chamber.

4. The system for breeding and harvesting insects of claim 1, further comprising a light source configured to expose the emerged adult insects with light including at least one wavelength of light conducive to mating between the emerged adult insects.

5. The system for breeding and harvesting insects of claim 1, wherein the egg-producing chamber structure includes a compartment for holding a hydrating fluid for the emerged adult insects.

6. The system for breeding and harvesting insects of claim 1, wherein the at least one oviposition region includes at least one egg-receiving aperture sized to allow the at least one of the insect eggs and the neonates of the insect eggs to pass therethrough.

7. The system for breeding and harvesting insects of claim 1, wherein the inclined surface is inclined generally between 25 to 90 degrees to a horizontal datum.

8. The system for breeding and harvesting insects of claim 1, wherein the inclined wall includes at least one helical projection connecting the bottom to the top of the inclined wall to assist the larvae in climbing the inclined surface.

9. The system for breeding and harvesting insects of claim 1, further comprising a frame structure positioned to receive the at least one larvae-growth chamber on support plates of the frame structure.

10. The system for breeding and harvesting insects of claim 9, further comprising a microclimate control system including: a heat source, a fan, a temperature and humidity sensor arrangement which monitors the temperature and humidity in the at least one larvae-growth chamber, and a control sub-system programmed to control a microclimate in the at least one larvae-growth chamber using the heat source, the sensor arrangement, and the fan.

11. The system for breeding and harvesting insect of claim 10, wherein the heat source transmits heat to at least one larvae-growth chamber through the support plate.

12. The system for breeding and harvesting insect of claim 11, wherein the sensor arrangement and a microswitch attached to the frame and automatically insert into at least one larvae-growth chamber through an aperture on the at least one larvae-growth chamber when the at least one larvae-growth chamber enters the frame.

13. The system for breeding and harvesting insect of claim 10, wherein the fan is operable to exchange air between outside and the at least one larvae-growth chamber through a carbon filter.

14. The system for breeding and harvesting insect of claim 1, further comprising at least one larvae motivation element selected from the group of larvae motivation elements consisting of: a heat element, a vibration element, a mechanical agitator, and a light element, wherein the at least one larvae motivation element is positioned and activated to act on larvae to urge the larvae to leave the passageway.

15. A method for breeding and harvesting insects, comprising:
providing an egg-producing chamber structure configured to receive insect pupae for pupation and to permit emerged adult insects to mate and oviposit insect eggs;
receiving the insect eggs in at least one oviposition region of the egg-producing chamber structure;
providing at least one larvae-growth chamber in communication with the at least one oviposition region so as to be configured to receive at least one of the insect eggs and neonates of the insect eggs from the at least one oviposition region, wherein the at least one larvae-growth chamber is configured to permit the at least one of the insect eggs and neonates of the insect eggs to transition into larvae and is configured to hold feed material for the larvae; and
providing an inclined surface positioned to receive larvae from the at least one larvae-growth chamber and provide passageway to permit the larvae to travel to a harvesting receptacle.

16. The method for breeding and harvesting insects of claim 15, further comprising:
providing hydration structures in the egg-producing chamber structure configured to provide a hydrating fluid to the emerged adult insects.

17. The method for breeding and harvesting insects of claim 15, further comprising actuating a microclimate control system including: a heat source, a fan, a temperature and humidity sensor arrangement which monitors the temperature and humidity in the at least one larvae-growth chamber, and a control sub-system programmed to control a microclimate in the at least one larvae-growth chamber using the heat source, the light source, the sensor arrangement, and the fan.

18. The method for breeding and harvesting insects of claim 15, further comprising operating the fan to exchange air between the at least one larvae-growth chamber and outside the at least one larvae-growth chamber through a carbon filter.

19. The method for breeding and harvesting insects of claim 15, further comprising:
providing a separation area positioned to hold larvae and detritus from the at least one larvae-growth chamber, and
operating at least one larvae motivation element selected from the group of larvae motivation elements consisting of: a heat element, a vibration element and a light element, wherein the at least one larvae motivation element is positioned and activated to act on larvae urging the larvae to leave separation area and enter the passageway.

20. A system for breeding and harvesting insects, comprising:
an egg-producing chamber structure configured to receive insect pupae for pupation and to permit emerged adult insects to mate and oviposit insect eggs;
at least one oviposition region in the egg-producing chamber structure configured to receive the insect eggs and apertured to permit at least one of the insect eggs and neonates of the insect eggs to pass therethrough;
at least one larvae-growth chamber in communication with the at least one oviposition region so as to be configured to receive the at least one of the insect eggs and neonates of the insect eggs, wherein the larvae-growth chamber is further configured to permit the at least one of the insect eggs and neonates of the insect eggs to transition into larvae and to hold feed material for the larvae;
a separation area positioned to hold larvae, and detritus from the at least one larvae growth chamber;
a harvesting receptacle positioned to hold larvae;
a passageway for the larvae to travel from the separation area to the harvesting receptacle;
at least one larvae motivation element selected from the group of larvae motivation elements consisting of: a heat element, a vibration element, a mechanical agitator, and a light element, wherein the at least one larvae motivation element is positioned and activated to act on larvae to urge the larvae to leave the separation area and enter the passageway.

* * * * *